US009351940B2

(12) United States Patent
Salman et al.

(10) Patent No.: US 9,351,940 B2
(45) Date of Patent: May 31, 2016

(54) NANOPARTICLES COMPRISING ESTERS OF POLY (METHYL VINYL ETHER-CO-MALEIC ANHYDRIDE) AND USES THEREOF

(75) Inventors: Hesham H. A. Salman, Noáin-Navarra (ES); Izaskun Goñi Azcarate, Pamplona (ES)

(73) Assignee: BIONANOPLUS, S.L., Noain-Navarra (ES)

( * ) Notice: Subject to any disclaimer, the term of this patent is extended or adjusted under 35 U.S.C. 154(b) by 0 days.

(21) Appl. No.: 14/111,855

(22) PCT Filed: Apr. 16, 2012

(86) PCT No.: PCT/EP2012/056900
§ 371 (c)(1),
(2), (4) Date: Dec. 30, 2013

(87) PCT Pub. No.: WO2012/140252
PCT Pub. Date: Oct. 18, 2012

(65) Prior Publication Data
US 2014/0161892 A1 Jun. 12, 2014

(30) Foreign Application Priority Data

Apr. 15, 2011 (EP) ..................................... 11382115

(51) Int. Cl.
| | |
|---|---|
| *A61K 9/16* | (2006.01) |
| *A61K 9/51* | (2006.01) |
| *B82Y 5/00* | (2011.01) |
| *C08J 3/07* | (2006.01) |
| *A61Q 19/00* | (2006.01) |
| *A61K 8/81* | (2006.01) |
| *A61K 9/00* | (2006.01) |
| *A61K 8/11* | (2006.01) |
| *A61K 31/00* | (2006.01) |
| *C08F 265/06* | (2006.01) |
| *C08J 3/12* | (2006.01) |
| *C08J 3/14* | (2006.01) |
| *A23L 1/00* | (2006.01) |
| *C08L 33/06* | (2006.01) |
| *A61Q 5/12* | (2006.01) |

(52) U.S. Cl.
CPC .................. *A61K 9/5138* (2013.01); *A23L 1/00* (2013.01); *A61K 8/11* (2013.01); *A61K 8/8164* (2013.01); *A61K 9/006* (2013.01); *A61K 9/0014* (2013.01); *A61K 9/5146* (2013.01); *A61K 9/5192* (2013.01); *A61K 31/00* (2013.01); *A61Q 19/00* (2013.01); *B82Y 5/00* (2013.01); *C08F 265/06* (2013.01); *C08J 3/07* (2013.01); *C08J 3/126* (2013.01); *C08J 3/14* (2013.01); *C08L 33/064* (2013.01); *A61K 2800/10* (2013.01); *A61K 2800/412* (2013.01); *A61Q 5/12* (2013.01); *C08J 2329/10* (2013.01); *C08J 2335/08* (2013.01); *Y10T 428/2982* (2015.01)

(58) Field of Classification Search
None
See application file for complete search history.

(56) References Cited

U.S. PATENT DOCUMENTS

| | | | |
|---|---|---|---|
| 3,461,461 | A | 8/1969 | Anthony et al. |
| 4,139,619 | A | 2/1979 | Chidsey, III |
| 4,164,562 | A | 8/1979 | Nandagiri et al. |
| 4,596,812 | A | 6/1986 | Chidsey, III et al. |
| 4,761,273 | A | 8/1988 | Grollier et al. |
| 5,981,719 | A | 11/1999 | Woiszwillo et al. |
| 6,090,925 | A | 7/2000 | Woiszwillo et al. |
| 6,197,349 | B1 | 3/2001 | Westesen et al. |
| 7,070,795 | B1 | 7/2006 | Botts et al. |
| 7,442,369 | B1 | 10/2008 | Pena et al. |
| 7,834,210 | B2 * | 11/2010 | Gupta ........................... 562/433 |
| 8,628,801 | B2 | 1/2014 | Garreta et al. |
| 2003/0108500 | A1 | 6/2003 | Imamura et al. |
| 2005/0037374 | A1 * | 2/2005 | Melker et al. ...................... 435/6 |
| 2005/0079222 | A1 | 4/2005 | Arbos Vila et al. |
| 2005/0276842 | A1 | 12/2005 | Zhang et al. |
| 2007/0224225 | A1 * | 9/2007 | Irache Garreta et al. .. 424/280.1 |
| 2009/0053160 | A1 | 2/2009 | Khoshdel et al. |
| 2010/0136129 | A1 | 6/2010 | Agüeros Bazo et al. |
| 2012/0016005 | A1 | 1/2012 | Samarsky et al. |
| 2012/0121693 | A1 | 5/2012 | Cotsarelis et al. |
| 2013/0324502 | A1 | 12/2013 | Lindahl et al. |

FOREIGN PATENT DOCUMENTS

| | | |
|---|---|---|
| DE | 202004012607 U1 | 11/2004 |
| EP | 0451390 A1 | 4/1990 |
| EP | 1369110 A1 | 3/2002 |
| EP | 1269973 A1 | 1/2003 |

(Continued)

OTHER PUBLICATIONS

Heller et al., Controlled drug release by polymer dissolution. I. Partial esters of maleic anhydride copolymers—properties and theory, J. Applied Polym. Sci. 1978, 22(7):1991-2009.*

Finne et al. Timolol Release from Matrices of Monoesters of poly(Vinyl Methyl Ether-Maleic Anhydride): Effects of Polymer Molecular Weight and a Basic Additive. J Pharm Sci. 1991; 80(7):670-673.*

Agüeros, Maite, et al.; "Bioadhesive properties and biodistribution of cyclodextrin-poly(anhydride) nanoparticles." European Journal of Pharmaceutical Sciences, 2009, pp. 231-240, vol. 37.

Agüeros, M., et al.; Combined hydroxypropyl-β-cyclodextrin and poly(anhydride) nanoparticles improve the oral permeability of paclitaxel. European Journal of Pharmaceutical Sciences, 2009, pp. 405-413, vol. 38.

(Continued)

*Primary Examiner* — Robert A Wax
*Assistant Examiner* — Olga V Tcherkasskaya
(74) *Attorney, Agent, or Firm* — Tristan A. Fuierer; Moore & Van Allen, PLLC

(57) ABSTRACT

The present invention relates to nanoparticles for encapsulating compounds, the preparation and uses thereof, said nanoparticles being based on half ($C_1$-$C_4$) alkyl esters of poly (methyl vinyl ether-co-maleic anhydride) (PVM/MA) copolymers. Said nanoparticles can encapsulate or incorporate a product of interest for use in the agricultural, cosmetic, food or pharmaceutical fields.

22 Claims, 10 Drawing Sheets

(56) References Cited

FOREIGN PATENT DOCUMENTS

| | | |
|---|---|---|
| EP | 1752141 A1 | 2/2007 |
| FR | 2732595 A1 | 10/1996 |
| GB | 1222016 | 2/1971 |
| GB | 2098624 A | 11/1982 |
| IN | 1575/MUM/2005 | 12/2005 |
| WO | 9505164 A1 | 2/1995 |
| WO | 9807410 A1 | 2/1998 |
| WO | 9900013 A2 | 1/1999 |
| WO | 0211698 A1 | 2/2002 |
| WO | 02069938 A1 | 9/2002 |
| WO | 2005104648 A2 | 11/2005 |
| WO | 2005105056 A1 | 11/2005 |
| WO | 2005120473 A2 | 12/2005 |
| WO | 2006105109 A2 | 10/2006 |
| WO | 2006119960 A1 | 11/2006 |
| WO | WO 2006119960 A1 * | 11/2006 |
| WO | 2007070643 A2 | 6/2007 |
| WO | 2007138135 A1 | 12/2007 |
| WO | 2008129106 A2 | 10/2008 |
| WO | 2009121997 A2 | 10/2009 |
| WO | 2010008582 A2 | 1/2010 |
| WO | 2012107564 A1 | 8/2012 |
| WO | 2012107573 A1 | 8/2012 |
| WO | 2012107575 A1 | 8/2012 |

OTHER PUBLICATIONS

Arbós, P., et al.; "Gantrez® AN as a new polymer for the preparation of ligand-nanoparticle conjugates." Journal of Controlled Release, 2002, pp. 321-330, vol. 83.

Arbós, P., et al.; "Influence of the surface characteristics of PVM/MA nanoparticles on their bioadhesive properties." Journal of Controlled Release, 2003, pp. 19-30, vol. 89.

Arbós, Pau, et al.; "Nanoparticles with specific bioadhesive properties to circumvent the pre-systemic degradation of fluorinated pyrimidines." Journal of Controlled Release, 2004, pp. 55-65, vol. 96.

Arbós, P., et al.; "Quantification of the bioadhesive properties of protein-coated PVM/MA nanoparticles." International Journal of Pharmaceutics, 2002, pp. 129-136, vol. 242.

Balata, Gehan, et al.; "Improvement of solubility and dissolution properties of ketoconazole by solid dispersions and inclusion complexes." Asian Journal of Pharmaceutical Sciences, 2010, pp. 1-12, vol. 5.

Barakat, Nahla S., et al.; "Diclofena sodium loaded-cellulose acetate butyrate: Effect of processing variables on microparticles properties, drug release kinetics and ulcerogenic activity." Journal of Microencapsulation, 2008, pp. 31-45, vol. 25.

Brigger, Iréne, et al.; "Nanoparticles in cancer therapy and diagnosis." Advanced Drug Delivery Reviews, 2002, pp. 631-651, vol. 54.

Calvo, P., et al.; "Novel Hydrophilic Chitosan-Polyethylene Oxide Nanoparticles as Protein Carriers." Journal of Applied Polymer Science, 1997, pp. 125-132, vol. 63.

Cerchiara, T., et al.; "Chitosan and poly(methyl vinyl ether-co-maleic anhydride) microparticles as nasal sustained delivery systems." European Journal of Pharmaceutics and Biopharmaceutics, 2005, pp. 195-200, vol. 61.

De La Fuente, María, et al.; "Novel Hyaluronan-Based Nanocarriers for Transmucosal Delivery of Macromolecules." Macromolecular Bioscience, 2008, pp. 441-450, vol. 8.

Domínguez-Delgado, Clara Luisa, et al.; "Preparation and characterization of triclosan nanoparticles intended to be used for the treatment of acne." European Journal of Pharmaceutics and Biopharmaceutics, 2011, pp. 102-107, vol. 79.

Enríquez De Salamanca, Amalia, et al.; "Chitosan Nanoparticles as a Potential Drug Delivery System for the Ocular Surface: Toxicity, Uptake Mechanism and In Vivo Tolerance." Investigative Ophthalmology & Visual Science, 2006, pp. 1416-1425, vol. 47.

Estevan, Maite, et al.; "Encapsulation of antigenic extracts of Salmonella enterica serovar Abortusovis into polymeric systems and efficacy as vaccines in mice." Veterinary Microbiology, 2006, pp. 124-132, vol. 118.

Favier, Isabelle, et al.; "Synthesis of New Functionalized Polymers and Their Use as Stabilizers of Pd, Pt, and Rh Nanoparticles. Preliminary Catalytic Studies." Journal of Applied Polymer Science, 2007, pp. 2772-2782, vol. 105.

Finne, U., et al.; "Modification of ocular and systemic absorption of timolol from ocular inserts by a buffering agent and a vasoconstrictor." International Journal of Pharmaceutics, 1990, pp. 19-27, vol. 65.

Finne, Ulla, et al.; "Timolol Release from Matrices of Monoesters of poly(Vinyl Methyl Ether-Maleic Anhydride): Effects of Polymer Molecular Weight and a Basic Additive." Journal of Pharmaceutical Sciences, 1991, pp. 670-673, vol. 80.

Gómez, Sara, et al.; "Allergen immunotherapy with nanoparticles containing lipopolysaccharide from Brucella ovis." European Journal of Pharmaceutics and Biopharmaceutics, 2008, pp. 711-717, vol. 70.

Gómez, Sara, et al.; "Gantrez® AN nanoparticles as an adjuvant for oral immunotherapy with allergens." Vaccine, 2007, pp. 5263-5271, vol. 25.

Gómez, Sara, et al.; "A novel nanoparticulate adjuvant for immunotherapy with Lolium perenne." Journal of Immunological Methods, 2009, pp. 1-8, vol. 348.

Guha, Suparna, et al.; "Dispersion polymerization of acrylamide III. Partial isopropyl ester of poly(vinyl methyl etheralt-maleic anhydride) as a stabilizer." Journal of Colloid and Interface Science, 2004, pp. 55-59, vol. 271.

Illum, L., et al.; "Chitosan as a novel nasal delivery system for vaccines." Advanced Drug Delivery Reviews, 2001, pp. 81-96, vol. 51.

Irache, Juan M., et al.; "Bioadhesive Properties of Gantrez Nanoparticles." Molecules, 2005, pp. 126-145, vol. 10.

Kannan, R.M., et al.; "Viscoelastic Properties of Highly Entangled Poly(vinyl methyl ether)." Macromolecules, 1997, pp. 3694-3695, vol. 30.

Kedor-Hackmann, Erika Rosa Maria, et al.; "First-derivative ultraviolet spectrophotometric and high performance liquid chromatographic determination of ketoconazole in pharmaceutical emulsions." Brazilian Journal of Pharmaceutical Sciences, 2006, pp. 91-98, vol. 42.

Kim, Jin-Chul, et al.; "After-Rinsing Hair Growth Promotion of Minoxidil-containing Amino α-Cyclodextrins." Journal of Microbiology and Biotechnology, 2007, pp. 1965-1969, vol. 17.

Kockisch, Sandra, et al.; "Mucoadhesive, triclosan-loaded polymer microspheres for application to the oral cavity: preparation and controlled release characteristics." European Journal of Pharmaceutics and Biopharmaceutics, 2005, pp. 207-216, vol. 59.

Kockisch, Sandra, et al.; "Polymeric Microspheres for Drug Delivery to the Oral Cavity: An In Vitro Evaluation of Mucoadhesive Potential." Journal of Pharmaceutical Sciences, 2003, pp. 1614-1623, vol. 92.

Kwon, Teak Kwan, et al.; "In vitro skin permeation of monoolein nanoparticles containing hydroxypropyl β-cyclodextrin/minoxidil complex." International Journal of Pharmaceutics, 2010, pp. 268-273, vol. 392.

Luzardo-Alvarez, A., et al.; "Effect of Formulation Variables on the Prediction of Release from Microparticles with Experimental Design." Journal of Applied Polymer Science, 2006, pp. 4546-4553, vol. 102.

Marchais, H., et al.; "Entrapment Efficiency and Initial Release of Phenylbutazone from Nanocapsules Prepared from Different Polyesters." Drug Development and Industrial Pharmacy, 1998, pp. 883-888, vol. 24.

Martins, Raquel Da Costa, et al.; "Design and influence of γ-irradiation on the biopharmaceutical properties of nanoparticles containing an antigenic complex from Brucella ovis." European Journal of Pharmaceutical Sciences, 2009, pp. 563-572, vol. 37.

Mills, Kingston H.G., et al.; "Protective Levels of Diphtheria-Neutralizing Antibody Induced in Healthy Volunteers by Unilateral Priming-Boosting Intranasal Immunization Associated with Restricted Ipsilateral Mucosal Secretory Immunoglobulin A." Infection and Immunity, 2003, pp. 726-732, vol. 71.

Nakache, Evelyne, et al.; "Biopolymer and Polymer Nanoparticles and Their Biomedical Applications." Handbook of Nanostructured Materials and Nanotechnology, 2000, pp. 577-635, vol. 5.

(56) References Cited

OTHER PUBLICATIONS

Ochoa, Javier, et al.; "Protective immunity of biodegradable nanoparticle-based vaccine against an experimental challenge with *Salmonella* Enteritidis in mice." Vaccine, 2007, pp. 4410-4419, vol. 25.

Peh, Kok Khiang, et al.; "Polymeric Films as Vehicle for Buccal Delivery: Swelling, Mechanical, and Bioadhesive Properties." Journal of Pharmacy and Pharmaceutical Sciences, 1999, pp. 53-61, vol. 2.

Perioli, Luana, et al.; "Novel mucoadhesive buccal formulation containing metronidazole for the treatment of periodontal disease." Journal of Controlled Release, 2004, pp. 521-533, vol. 95.

Read, Robert C., et al.; "Effective nasal influenza vaccine delivery using chitosan." Vaccine, 2005, pp. 4367-4374, vol. 23.

Salman, Hesham H., et al.; "Bioadhesive Mannosylated Nanoparticles for Oral Drug Delivery." Journal of Nanoscience and Nanotechnology, 2006, pp. 1-7, vol. 6.

Salman, Hesham H., et al.; "Bioadhesive capacity and immunoadjuvant properties of thiamine-coated nanoparticles." Vaccine, 2007, pp. 8123-8132, vol. 25.

Salman, Hesham H., et al.; "Evaluation of Bioadhesive Capacity and Immunoadjuvant Properties of Vitamin B12-Gantrez Nanoparticles." Pharmaceutical Research, 2008, pp. 2859-2868, vol. 25.

Salman, Hesham H., et al.; "Salmonella-like bioadhesive nanoparticles." Journal of Controlled Release, 2005, pp. 1-13, vol. 106.

Takeuchi, Hirofumi, et al.; "Mucoadhesive nanoparticulate systems for peptide drug delivery." Advanced Drug Delivery Reviews, 2001, pp. 39-54, vol. 47.

Veyret, Raphael, et al.; "Magnetic colloids for the generic capture of viruses." Analytical Biochemistry, 2005, pp. 59-68, vol. 346.

Yoncheva, Krassimira, et al.; "Development of bioadhesive amino-pegylated poly(anhydride) nanoparticles designed for oral DNA delivery." Journal of Microencapsulation, 2008, pp. 82-89, vol. 25.

Yoncheva, K., et al.; "Evaluation of bioadhesive potential and intestinal transport of pegylated poly(anhydride) nanoparticles." International Journal of Pharmaceutics, 2007, pp. 156-165, vol. 334.

Yoncheva, Krassimira, et al.; "Pegylated nanoparticles based on poly(methyl vinyl ether-co-maleic anhydride): preparation and evaluation of their bioadhesive properties." European Journal of Pharmaceutical Sciences, 2005, pp. 411-419, vol. 24.

\* cited by examiner

NANOPARTICLES COMPRISING ESTERS OF POLY (METHYL VINYL ETHER-CO-MALEIC ANHYDRIDE) AND USES THEREOF

CROSS-REFERENCE TO RELATED APPLICATIONS

This application is filed under the provisions of 35 U.S.C. §371 and claims the priority of International Patent Application No. PCT/EP2012/056900 filed on 16 Apr. 2012 entitled "NANOPARTICLES COMPRISING ESTERS OF POLY (METHYL VINYL ETHER-CO-MALEIC ANHYDRIDE) AND USES THEREOF" in the name of Hesham H. A. SALMAN, et al., which claims priority to European Patent Application No. EP11382115.1, filed on 15 Apr. 2011, both of which are hereby incorporated by reference herein in their entirety.

FIELD OF THE INVENTION

The invention relates to a biocompatible nanoparticulate delivery system comprising nanoparticles based on half esters of poly (methyl vinyl ether-co-maleic anhydride) (PVM/MA) copolymers having high mucosal bioadhesion ability and high long-term stability in aqueous media. The nanoparticles are capable of efficiently incorporating products of interest in Agriculture, Cosmetics, Food and Pharmacy. The invention also relates to a process for the production of said nanoparticles and to the uses and applications thereof.

BACKGROUND OF THE INVENTION

Bioadhesive polymeric nanoparticles or microparticles have been considered as promising particulate systems for the delivery of many compounds, including therapeutic molecules. The bioadhesive properties of these systems offer the possibility of creating a strong interaction and prolonged contact with the mucosal surfaces resulting in a significant increase drug absorption and improvement of patient compliance. Different studies and reviews describe the beneficial applications for buccal, nasal, ocular, oral, rectal and vaginal routes and provide examples of what can be achieved in vivo when using bioadhesive formulations.

Buccal bioadhesive microparticles and nanoparticles allow achieving local drug release in the mucosa. Within the oral cavity, it has been described the treatment of toothache, bacterial and fungal infections, aphthous ulcers, lichen planus, inflammation and dental stomatitis. A great number of studies have reported the use of buccal delivery systems for controlled release of drugs, such as fentanyl, denbufylline, zinc sulfate, chlorhexidine and theophylline. Intranasal mucoadhesive microspheres based on bioadhesive polymers such as chitosan, hyaluronic acid, and other polymers, enhance drug bioavailability [1-3] including desmopressin. Similarly, these systems enhance the oral bioavailability of biologically active molecules such as calcitonin. Further, bioadhesive microcarriers and nanocarriers were applied for the local application of many drugs in ophthalmology where they could prolong the drug release and did not produce the sensation of a foreign body or visual blurring. Mucoadhesive nanoparticles or microparticles have been also applied for local delivery strategies including skin delivery purposes, or to hair follicle. A new approach for the preparation of mucoadhesive microparticles has been considered as an innovative vaginal delivery system for econazole nitrate in the treatment of *Candida albicans*. One of the most interesting areas of research within the field of bioadhesive microparticles and nanoparticles has been focused on the mucosal vaccination and immunotherapy to enhance the induction of antibody responses in serum, as well as local and distal mucosal secretions. Significant advantages in using such an approach include ease of administration and the generation of both systemic and mucosal immunities.

Many bioadhesive polymers have been described to be applied to obtain bioadhesive particulate systems include polyacrylic acid (PAA), polyvinyl alcohol (PVA), cellulose derivatives and sodium alginate. Various copolymers of acrylic acid, such as acrylic acid/polyethylene glycol monomethyl ether copolymer and acrylic acid-2 ethylhexyl acrylate copolymer have also been studied. PAA, chitosan and its derivatives, hydroxypropylcellulose (HPC), PVA, gelatine, carrageenan, sodium carboxymethylcellulose (NaCMC), and hyaluronic acid, have been proved to interact with buccal mucosa.

Other promising bioadhesive polymers are those commercialized by International Specialty Products (ISP) under trademark GANTREZ®, i.e., poly methyl vinyl ether-co-maleic anhydride (PVM/MA) copolymers, that have been applied as adhesives, binder, fixatives, mucoadhesive for oral delivery strategies, buccal adhesive strategies, transdermal delivery systems and other cosmetic applications such as hair styling products. GANTREZ® copolymers include:

GANTREZ® AN copolymers, the anhydride form, which are supplied as a water-insoluble white powder that can be easily hydrolyzed to produce a transparent solution of the water-soluble free acid (GANTREZ® S);

GANTREZ® S copolymers, the free acid form, which are supplied in solution or in powder form;

GANTREZ® MS copolymers, a mixed salt of sodium/calcium PVM/MA copolymers, which are supplied as a powder, which can be slowly hydrolyzed in water, and GANTREZ® ES copolymers, the half ester form of different alkyl chain lengths and molecular weights of PVM/MA copolymer, namely GANTREZ® ES 225 (monoethyl ester), GANTREZ® ES 425 (monobutyl ester) and GANTREZ® ES335I (isopropyl ester); these copolymers are water-insoluble but they are water-soluble when neutralized by bases in aqueous solution, and they are supplied as alcoholic solutions.

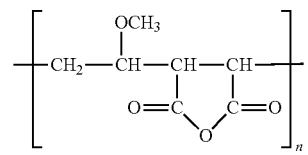

Gantrez AN

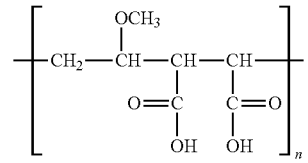

Gantrez S

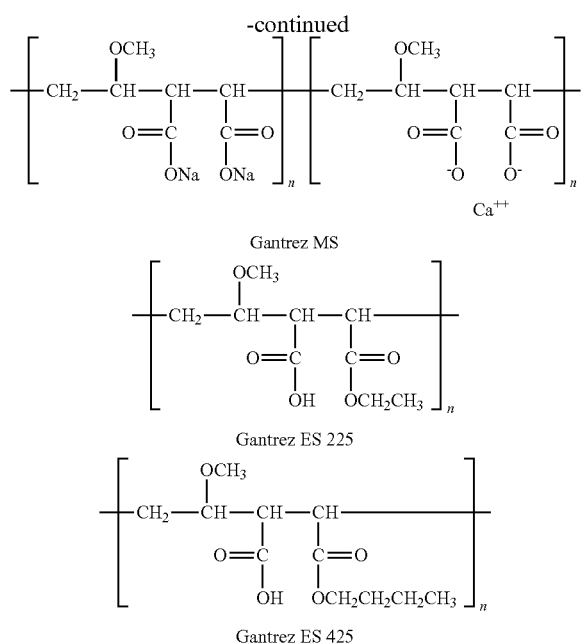

Synthetic PVM/MA copolymers have very different applications. By illustrative, GANTREZ® AN copolymers are widely used as a thickener and flocculant, dental adhesive, excipient in oral tablets, excipient in transdermal patches, etc. In addition, the use of these copolymers for the controlled release of drugs and, in matrix forms, for the topical release of drugs in the eye as well as in the fabrication of bioadhesive microparticles or nanoparticles for drug delivery purposes or mucosal vaccination [4-5] has been reported. GANTREZ® S copolymers are used in toothpastes and mouthwashes, mainly as adhesive polymer for buccal hygiene products for the prolonged delivery of antimicrobial agents. GANTREZ® MS copolymer is used in denture adhesives, ostomy adhesives and in topical carriers for mucosal applications; micro- and nanoparticles based on GANTREZ® MS copolymer for local buccal cavity delivery purposes have been reported. GANTREZ® ES copolymers are used in enteric film coating agents and in ostomy adhesives; microparticles based on n-hexyl half ester of PVM/MA copolymer containing ketorolac tromethamine having an average diameter of 100-150 µm have been reported [6] although the eventual application of said microparticles is limited because they are normally degrade in vitro over a period of 4-5 days.

Many investigations have used PVM/MA copolymers to obtain micro- or nanoparticulate systems.

Nanosystems based on GANTREZ® AN copolymers are mainly obtained by the solvent displacement method. In this context, it has been reported the desolvatation of the PVM/MA copolymer in acetone with a hydroalcoholic phase followed by cross-linking of the nanoparticles formed with cross-linkers (e.g., polyamines or proteins). The stability in aqueous media of these nanosystems is quite short due to the hydrolysis of the GANTREZ® AN copolymer to GANTREZ® S copolymer which is water soluble. In an aqueous medium, said nanoparticles can be dissolved quite rapid. The stabilization of GANTREZ® AN nanosystems in aqueous medium needs a chemical modification and functionalization of the PVM/MA copolymer with a cross-linking agent (cross-linker), for example, a polyamine compound such as spermidine or spermine (although this coupling reaction needs at least 20 h under certain conditions), a diamine compound such as the toxic 1,3-diaminopropane (DP), or an immunogenic molecule such as bovine serum albumin (BSA). The addition of DP only weakly enhances the stability of GANTREZ® AN nanoparticles in phosphate buffered saline (PBS) [7]. Other disadvantages of cross-linking PVM/MA nanoparticles include the significant increase in the nanoparticles size and the dramatic decrease of the bioadhesive capacity of the nanosystems. In order to enhance the bioadhesive capacity of the GANTREZ® AN nanoparticles, said nanoparticles can be modified by hydrosoluble polymers such as poly ethylene glycols (PEG). However, this approach is accomplished with some drawbacks such as, for example, the modification of maleic anhydride copolymers with a hydroxyl containing compound to form ester derivatives need a high temperature and aggressive acidic conditions, and the use of hydrophilic PEG (low OH content) may transform the GANTREZ® AN copolymer into a more hydrosoluble derivative and thus decrease the stability in aqueous media of the resulting nanoparticles.

Further, some difficulties have been reported in relation with the ability of GANTREZ® AN nanoparticles for incorporating hydrosoluble drugs in the organic phase of the polymer (a solution of GANTREZ® AN in acetone). As it is known, hydrosoluble drugs are not soluble in acetone and may form big size crystals that can interfere with the formation of nanoparticles once a hydroalcoholic solution is added to precipitate GANTREZ® AN in the form of nanosystems. For that reason, a hydrosoluble drug, 5-fluorouridine (FURD), was loaded in GANTREZ® AN nanoparticles only by incubating the drug with the previously formed nanoparticles and, consequently, a very low encapsulation efficiency was obtained (about 13%) [8].

With respect to the capacity of GANTREZ® AN nanoparticles to incorporate water-insoluble or poorly water-soluble molecules, it has been necessary to use complexing agents such as cyclodextrins (CDs) or solubilizers including PEG and amino acids (e.g., glycin) in order to enhance the incorporation of said type of molecules in GANTREZ® AN nanoparticles. In fact, if complexing agents or solubilizers are not used, the free drug, which is not incorporated into GANTREZ® AN nanoparticles, will precipitate as big crystals in the final aqueous suspension of the nanoparticles obtained post organic solvents evaporation under reduced pressure. Thus, the poorly water-soluble molecules encapsulation efficiency is extremely low if co-solvents are not used. Although the use of co-solvents PEG and amino acids increases the encapsulation efficacy of poorly water-soluble compounds (e.g., paclitaxel), it dramatically reduces the yield of the nanoparticles manufacture process.

GANTREZ® MS microspheres, prepared by double emulsion techniques, showed a low encapsulation efficiency of water-insoluble molecules (around 30% in case of triclosan). In addition, a rapid release of triclosan was achieved (about 100% within the first hour in PBS) which indicated the low stability of the GANTREZ® MS microsystems and the rapid drug release and/or microsystems degradation [9]. Further, GANTREZ® MS based particulate systems showed a rapid swelling in isotonic phosphate buffer (pH 7.0) (swilling half time around 10 min) and short retention times on porcine esophageal mucosa [10].

On the other hand, a very important aspect for nanoparticles production is the complexity of industrial production and scale up processes. Many techniques have been developed to prepare nanoparticles for the delivery of drugs such as emulsification or solvent evaporation techniques which involve the use of organic toxic solvents (e.g., dichloromethane, ethyl acetate, chloroform, acetone, etc.), and special complex devices such as homogenizers. The implementation of said techniques at large-scale production is still a challenge, as it requires defined steps which include process feasibility, formulation optimization, process optimization, scale-up and validation in order to develop quality products and provide a rational approach for production steps including drug concentration and polymer concentration, processing operations, particle size, drug stability or entrapment efficiency.

Although a great number of nanoparticulate systems for the delivery of products of interest based on the use of PVM/MA copolymers are known, there are some drawbacks which are still unsolved and limit their applications.

It is therefore necessary to develop further nanoparticulate systems for the delivery of products of interest which are capable of solving all or some of the above mentioned drawbacks related to the nanoparticulate systems based on PVM/MA copolymers, for example, low long-term stability in an aqueous medium, the use of cross-linkers to improve stability in aqueous media, low encapsulation efficacy for hydrophilic compounds, the use of co-solvents or complexing agents to improve the efficacy for encapsulating hydrophobic compounds, a cost and complex production process which requires the use of toxic organic solvents or complex techniques. Advantageously, said further nanoparticulate systems for the delivery of products of interest should have, in addition to high mucosal bioadhesion ability, high long-term stability in aqueous media and high encapsulation efficiency of products of interest, including oils as well as small or large, hydrophilic or hydrophobic, compounds, and/or they should be produced by more simple, environmental friendly processes. These objectives can be achieved by means of the nanoparticles provided by the present invention.

SUMMARY OF THE INVENTION

It has been now surprisingly found that mixing a pharmaceutically or cosmetically accepted solvent such as ethanol or a polyol (e.g., propylene glycol) containing a half ($C_1$-$C_4$) alkyl ester of a poly (methyl vinyl ether-co-maleic anhydride) (PVM/MA) copolymer with an aqueous medium, optionally in the presence of an excipient, allows the spontaneous formation of nanoparticles with a very homogeneous small size (about 130 nm) and high nanoparticles yield (about 98%). This method allows obtaining nanoparticles with high encapsulation efficiency of both large and small hydrophilic molecules (BSA and Rhodamine B) as well as hydrophobic molecules (Ketoconazole, Minoxidil and Triclosan) without the need of further organic solvents (e.g., acetone, dichloromethane or ethyl acetate), co-solvents (e.g., CDs or PEGs) or surfactants which are usually applied to obtain nanosystems. In addition, this nanoparticles manufacture method also allows forming in situ self-assembled nanoparticles (SANP) in a body fluid once a copolymer solution containing a product of interest (POI) is mixed with said fluid; consequently, POI-loaded nanoparticles can be in situ spontaneously formed in contact with the body fluid (an aqueous medium).

The simplicity of the process for the manufacture of nanoparticles based on half ($C_1$-$C_4$) alkyl esters of PVM/MA copolymers reduces the industrial scale cost due to the simplicity to obtain these nanosystems without the use of any special apparatus. Further, the avoidance of acetone as solvent, chemical cross-linking and drying processes is an advantageous critical step in the manufacture of these systems in comparison with other PVM/MA nanoparticles (e.g., GANTREZ® AN-based nanoparticles).

The resulting nanoparticles based on half ($C_1$-$C_4$) alkyl esters of PVM/MA copolymers have shown a long-term stability (low degradation rate) higher than that of the GANTREZ® AN-based nanoparticles, in 3 months, without any change in the average size, at different conditions in an aqueous medium. This may allow the direct commercialization of aqueous suspensions of nanoparticles based on half ($C_1$-$C_4$) alkyl esters of PVM/MA copolymers without the need of using toxic cross-linkers, lyophilization or other drying techniques. In addition, they can be easily incorporated in many dosage forms such as solutions, suspensions, gels and semi-solids or solid ones which are widely used in cosmetic and pharmaceutical industry.

Further, nanoparticles based on half ($C_1$-$C_4$) alkyl esters of PVM/MA copolymers displayed an adhesive affinity to porcine buccal and tongue mucosa model surfaces higher than that observed for other GANTREZ® AN copolymers-based nanoparticles which guarantees an effective enhancement of the controlled release of a product of interest.

Surprisingly, half ($C_1$-$C_4$) alkyl esters of PVM/MA copolymers as well as nanoparticles based on half ($C_1$-$C_4$) alkyl esters of PVM/MA copolymers have a co-solvent effect of poorly water-soluble compounds leading to an enhancement of the encapsulation efficiency of the hydrophobic drugs (Ketoconazole, Minoxidil or Triclosan) used in these studies. Thus, said nanoparticles based on half ($C_1$-$C_4$) alkyl esters of PVM/MA copolymers guarantee a high efficacy to encapsulate both hydrophilic and, especially, hydrophobic molecules without the need of using co-solvents or complexing agents.

Summing up, the nanoparticles based on half ($C_1$-$C_4$) alkyl esters of PVM/MA copolymers show, among others, the following properties: (i) high adhesive affinity to the mucosal surfaces; (ii) high long-term stability (degradation rate) in both aqueous and hydro-alcoholic media; (iii) high efficacy to encapsulate hydrophilic and especially hydrophobic molecules without the need of co-solvents or complexing agents, and (iv) high facility to be incorporated in many dosage forms, for example, liquid, solids or semi-solids, such as suspensions, gels, etc. In addition, advantageously, said nanoparticles can be easily produced at small and large scale levels without the use of toxic organic solvents or complex techniques. All of the above mentioned properties favour the use of said nanoparticles in different fields, such as in the agricultural, food, etc., fields, specially, in the cosmetic and pharmaceutical fields, as controlled release delivery systems to different surfaces including, among other, hair, skin, etc., or their administration by buccal, nasal, oral, rectal, vaginal, among others, routes.

Therefore, it is an objective of this invention, the production and uses of nanoparticles based on half ($C_1$-$C_4$) alkyl esters of PVM/MA copolymers.

Thus, in an aspect, the invention relates to a nanoparticle selected from the group consisting of:
  a) a matrix nanosphere, wherein said matrix nanosphere comprises a matrix, said matrix comprising a half ($C_1$-$C_4$) alkyl ester of a poly (methyl vinyl ether-co-maleic anhydride) (PVM/MA) copolymer; and
  b) a core-shell vesicular nanocapsule, wherein said core-shell vesicular nanocapsule comprises a core and a shell, said shell comprising a half ($C_1$-$C_4$) alkyl ester of a PVM/MA copolymer.

In a particular embodiment, said nanoparticle provided by the present invention, further comprises a product of interest, e.g., a product of interest in the agriculture, cosmetics, food, or pharmacy industries.

In another aspect, the invention relates to a composition comprising at least one nanoparticle provided by the present invention and a carrier. In a particular embodiment, the composition is a cosmetic composition or a pharmaceutical composition suitable for its administration by the buccal, dental, nasal, ocular, oral, parenteral, rectal, topical, or vaginal route.

In another aspect, the invention relates to a composition comprising:
a) a component selected from the group consisting of:
   i. at least one nanoparticle according to the invention; and
   ii. a solution or suspension containing a half ($C_1$-$C_4$) alkyl ester of a poly (methyl vinyl ether-co-maleic anhydride) (PVM/MA) copolymer and a product of interest in a medium, said medium comprising a volatile water miscible alcohol and an aqueous medium, wherein the amount of aqueous medium is lower than the necessary amount of aqueous medium to form nanoparticles; and
b) a carrier,
wherein said product of interest is selected from the group consisting of acetylsalicylic acid, alpha-atrial natriuretic peptide, arginine vasopressin, atropine, augmerosen, atorvastatin, AVASTIN® (bevacizumab), calcitonins, chorionic gonadotropins, corticotropin, desmopressin, epibatidine, ERBITUX® (cetuximab), exenatide, HERCEPTIN® (trastuzumab), HUMIRA® (adalimumab), HUMULIN®, ketoconazole, lanreotide, lutropin alpha, metoprolol, minoxidil, nesiritide, octreotide, paclitaxel, paracetamol, pegaptanib, recombinant follicle stimulating hormone, recombinant growth factors, REMICADE® (infliximab), RITUXAN® (rituximab), sermorelin, somatotropin, a taxane derivative, taxol, teriparatide acetate, thyrotropin, triclosan, urofollitropin, XOLAIR® (omalizumab), actinomycin D, albendazole, aldosterone, alprazolam, amiodarone, amitriptyline, amprenavir, asimadoline, atorvastatin, bunitrolol, buspirone, camptothecin, carbamazepine, carvedilol, celiprolol, cyclosporine A, cimetidine, clotrimazole, colchicine, cortisone, daunorubicin, debrisoquine, dexamethasone, diazepam, digitoxin, digoxin, diltiazem, docetaxel, domperidone, doxorubicin, efavirenz, epirubicin, erythromycin, ergotamine, estradiol, estradiol glucuronide, erlotinib, etoposide, phenytoin, fentanyl, felodipine, phenothiazines, fexofenadine, fluoroquinolones, fluorouracil, FK-506, gentamicin, griseofulvin, hydrocortisone, imatinib, indinavir, itraconazole, ivermectin, ketoconazole, kaempferol, levofloxacin, lidocaine, loperamide, losartan, lovastatin, mebendazole, methylprednisolone, methotrexate, mibefradil, midazolam, nisoldipine, morphine, nelfinavir, nicardipine, nitrendipine, nifedipine, ondansetron, paclitaxel, pentazocine, praziquantel, prednisolone, prednisone, quercetin, quinidine, ranitidine, rapamycin, rifabutin, rifampicin, ritonavir, saquinavir, sirolimus, sulfamethizole, tacrolimus, tamoxifen, talinolol, teniposide, terfenadine, tetracycline, topotecan, triamcinolone, valspodar, verapamil, vinblastine, vincristine, vindesine, zopiclone, and mixtures thereof.

In another aspect, the invention relates to a foodstuff comprising a nanoparticle provided by this invention.

In another aspect, the invention relates to a nanoparticle provided by the present invention wherein the product of interest is Minoxidil, for use in treating hair loss, or wherein the product of interest is Triclosan or Ketoconazole for use in the treatment of a buccal infection.

In further aspects, the invention relates to the use of a nanoparticle provided by the present invention wherein the product of interest is minoxidil in the manufacture of a medicament for the treatment of hair loss, or wherein the product of interest is triclosan or ketoconazole in the manufacture of a medicament for the treatment of a buccal infection.

In further aspects, the invention relates to a method of treatment of hair loss in a subject comprising the administration to said subject of a nanoparticle provided by the present invention loaded with minoxidil, or a method of treatment of a buccal infection in a subject comprising the administration to said subject of a nanoparticle provided by the present invention loaded with triclosan or ketoconazole.

In another aspect, the invention relates to a process for producing a matrix nanosphere which comprises a matrix, said matrix comprising a half ($C_1$-$C_4$) alkyl ester of a poly (methyl vinyl ether-co-maleic anhydride) (PVM/MA) copolymer, said process comprising contacting an organic solution or suspension containing a half ($C_1$-$C_4$) alkyl ester of a PVM/MA copolymer with an aqueous medium in order to form said matrix nanosphere.

In another aspect, the invention relates to a process for producing a matrix nanosphere which comprises a product of interest, wherein said matrix nanosphere comprises a matrix, said matrix comprising a half ($C_1$-$C_4$) alkyl ester of a poly (methyl vinyl ether-co-maleic anhydride) (PVM/MA) copolymer, said process comprising:
a) contacting an alcoholic or hydroalcoholic solution or suspension comprising said product of interest and said half ($C_1$-$C_4$) alkyl ester of the PVM/MA copolymer with an aqueous medium; or, alternatively,
b) contacting an alcoholic solution or suspension comprising said product of interest and said half ($C_1$-$C_4$) alkyl ester of the PVM/MA copolymer with an aqueous medium; or, alternatively,
c) contacting an organic solution or suspension comprising said product of interest and said half ($C_1$-$C_4$) alkyl ester of the PVM/MA copolymer with an aqueous medium, wherein said organic solution or suspension comprises a non-volatile water miscible solvent.

In another aspect, the invention relates to a process for producing a core-shell vesicular nanocapsule which comprises a product of interest, wherein said core-shell vesicular nanocapsule comprises a core and a shell, said shell comprising a half ($C_1$-$C_4$) alkyl ester of a PVM/MA copolymer, said process comprising contacting a solution or suspension comprising said product of interest and said half ($C_1$-$C_4$) alkyl ester of a PVM/MA copolymer with an aqueous medium.

DETAILED DESCRIPTION OF THE INVENTION

Figure 1:
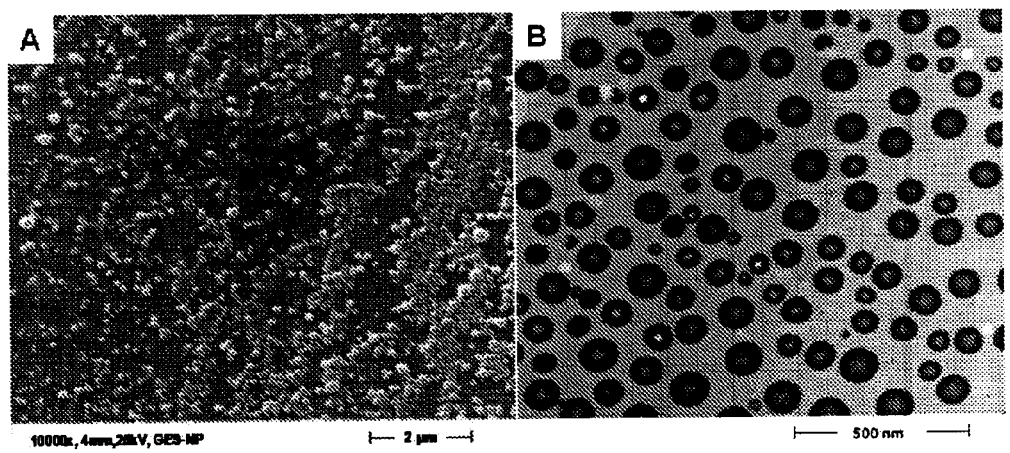
FIG. 1. Photography of GANTREZ® ES 225 nanoparticles obtained by (A) Scanning Electron Microscopy (SEM) and by (B) Transmission Electron Microscopy (TEM).

The present invention provides nanoparticles based on half ($C_1$-$C_4$) alkyl esters of PVM/MA copolymers, methods for producing said nanoparticles, and applications of said nanoparticles.

DEFINITIONS

For the purpose of facilitating the comprehension of the present invention, the meaning of some terms and expressions as used in the context of the invention are set forth below.

As used herein, the term "$C_1$-$C_4$ alkyl" relates to a radical derived from a linear or branched alkane of 1 to 4 carbon atoms, for example, methyl, ethyl, propyl, isopropyl, butyl, isobutyl, etc.

"Average size" or "mean size", as used herein, relates to the average diameter of a population of nanoparticles moving together in an aqueous medium. The average size of these systems can be measured by standard processes known by persons skilled in the art and which are described, by way of illustration, in the experimental part attached to the examples described below. The average size of the particles can be mainly affected by the amount and molecular weight of the copolymer, and by the nature and amount of the product of interest (if any), present in the nanoparticles of the invention (generally, the larger the amount or molecular weight of said components, the larger the average size of the nanoparticle), and by some parameters of the process for the production of said nanoparticles, such as the stirring speed, etc.

A product is said to be "food-grade" when its use in human or animal food is safe according to the Codex Alimentarius of a country or of an organization, for example, the Food and Agriculture Organization (FAO) of the United Nations or the World Health Organization (WHO); consequently, a "food-grade" product is a non-toxic product "suitable for use thereof in food" and therefore both expressions are synonyms and are indistinctly used in this description.

The term "half ($C_1$-$C_4$) alkyl of a poly (methyl vinyl ether-co-maleic anhydride) (PVM/MA) copolymer", as used herein, relates to a structure of formula

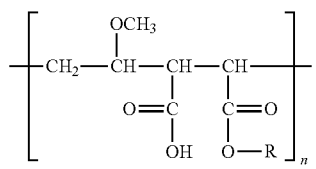

wherein R is a $C_1$-$C_4$ alkyl, in which only one of the two carboxyl groups is esterified.

As used herein, the term "nanoparticle" refers to a colloidal system of a solid polymeric particle with an average size less than 1 micrometer (μm), typically between 10 and 900 nanometers (nm), preferably between 50 and 500 nm, more preferably between 100 and 400 nm, still more preferably between 120 and 160 nm, still more preferably between 120 and 160 nm approximately, formed by natural or synthetic polymers (in this case, formed by polymerization of a half ($C_1$-$C_4$) alkyl ester of a PVM/MA copolymer). Depending, among other facts, on their manufacture method, nanoparticles can be subdivided into matrix nanospheres and core-shell vesicular nanocapsules [11]. "Matrix nanospheres" are matrix forms formed by a polymeric three-dimensional network; when a nanosphere is loaded with a product of interest, e.g., a drug, said product of interest can be physically and uniformly dispersed in said three-dimensional network. The matrix or three-dimensional network of the matrix nanosphere of the invention contains a half ($C_1$-$C_4$) alkyl ester of a PVM/MA copolymer. "Core-shell vesicular nanocapsules" are vesicular systems formed by an inner cavity (known as "core") which optionally contain the product of interest and surrounded by a polymeric wall or membrane (known as "shell"), i.e., they are nano-vesicular systems that exhibit a typical core-shell structure in which the product of interest is confined to a reservoir or within a cavity ("core") surrounded by a polymer wall or membrane ("shell"). The person skilled in the art knows that the core of the core-shell vesicular nanocapsule may contain only excipients, may contain any product of interest as defined hereinafter, or may contain both excipients and said product of interest as defined hereinafter. In both cases, due to the large specific surface of these systems, the molecules of the product of interest may be trapped or adsorbed in the surface of the nanoparticles.

As it is used herein, a "product of interest" or "POI" refers to any compound susceptible of being used in any type of industry, for example, in the agricultural, cosmetic, food, or pharmaceutical industries. Practically any compound susceptible of being used in any type of industry can be considered a POI in accordance with the present invention. Illustrative, non-limiting examples of POI according to the present invention include small or large, water-soluble or lipid-soluble, hydrophilic, hydrophobic or amphiphilic, organic or inorganic, compounds, such as lipids, nucleosides, nucleotides, oils, oligonucleotides, peptides, polynucleotides, proteins, small organic chemical compounds, etc. The POI may be in any form or state, for example, in liquid, semisolid or solid state, i.e., the POI may be dissolved or dispersed in aqueous or organic mediums, thus forming an aqueous or organic solution or suspension, including oily solutions or suspensions, or, alternatively, the POI may be undissolved or undispersed, as a solid product.

In a particular embodiment, the POI is a compound having agricultural activity, i.e., susceptible of being used in the agricultural industry, for example, a phytosanitary product for controlling pests and pathogens, a plant growth promoting agent, for example, herbicides (e.g., glyphosate, etc.), insecticides (e.g., lambda-cyhalothrin, etc.), fungicides (e.g., Mancozeb), etc.

In another particular embodiment, the POI is a compound having cosmetic activity, i.e., a substance used to enhance the appearance or odor of the human or animal body. Cosmetics include skin-care creams, lotions, powders, perfumes, lipsticks, fingernail and toe nail polish, eye and facial makeup, towelettes, permanent waves, colored contact lenses, hair colors, hair sprays and gels, deodorants, hand sanitizer, baby products, bath oils, bubble baths, bath salts, butters and many other types of products. Illustrative, non-limiting, examples of POI used in the cosmetic industry include anti-aging products (e.g., retinoids), anti-acne products (e.g., erythromycin, benzoyl peroxide, etc.), facial care products (e.g., GHK copper in facial cleansers, etc.), pigmented cosmetics (e.g., color pigments used in rouges, foundations, cover-up, powder, etc.), cosmeticals (e.g., Co-Q10, etc.), personal care products (e.g., moisture-controlled release of fragrance in deodorants, etc.), products for sunscreen/suncare (e.g., UV-blockers), products for tooth-cleaners, toothpastes, or rinses (e.g., sustained release of triclosan/bactericides, flavors, scents, anti-dry mouth actives in mouth, etc.), products for shampoo (e.g., anti-dandruff/moisturizing actives, etc.), perfumes (e.g., scent particles, etc.), hair products (e.g., fixatives, volumetric hair styling products, etc.).

In another particular embodiment, the POI is a compound having nutritional activity, i.e., susceptible of being used in the food industry, for example, folic acid, 4-aminobenzoic acid, niacin or vitamin B3, pantothenic acid or vitamin B5, thiamine monophosphate, thiamine pyrophosphate, thiamine triphosphate, ascorbic acid, pteroylpolyglutamic acids, folinic acid, nicotinic acid, hyaluronic acid, thioctic acid, p-coumaric acid, caffeic acid, vitamins of the A, D, E, K families and derivatives thereof, phospholipids, carotenoids (e.g., carotenes, lycopene, lutein, capsanthin, zeaxanthin, etc.), fatty acids, omega-3 fatty acids (e.g., DHA, EPA, etc.), amino acids (e.g., iso-leucine, leucine, methionine, phenylalanine, tryptophan, and valine), phytostanols or phytosterols (e.g., sitosterol, campesterol, stigmasterol, etc.), polyphenols (quercetin, rutin, resveratrol, kaempferol, myricetin, isorhamnetin, etc.), etc.

In another particular embodiment, the POI is a compound having therapeutical activity (i.e., a substance which, when administered to a subject, interacts with its receptor in the action site and exerts a certain effect); this kind of products are susceptible of being used in the pharmaceutical industry. Illustrative, non-limiting, examples of POI having therapeutical activity include antibodies or fragments, thereof, bacterial, fungal or viral proteins or antigens, cell receptors, coagulation factors, cytokines, enzymes, erythropoietins, growth factors, hormones, insulins, interleukins, interferons, ligands, nucleic acids (e.g., nucleotides, oligonucleotides, polynucleotides, DNA, RNA, etc.), signal transducing agents, small organic chemical compounds, toxins, etc. In a particular embodiment, the POI includes analgesic (narcotic) agents (e.g., codeine, morphine, etc.), analgesic (non-narcotic) agents (e.g., acetylsalicylic acid, flufenamic acid, etc.), antialopecia agents (e.g., finasteride, minoxidil, etc.), antianginal agents (e.g., atenolol, nicardipine, etc.), antibacterial agents (e.g., amoxicillin, ampicillin, azythromycin, cefaclor, ciprofloxacin, neomycin, tetracycline, etc.), antidepressant agents (e.g., fluoxetine, paroxetine, etc.), antifungal agents (e.g., isoconazole, ketoconazole, etc.), antihypertensive agents (e.g., benazepril, captopril, carvedilol, enalapril, losartan, minoxidil, etc.), antiinflammatory agents (e.g., niflumic acid, celecoxib, ibuprofen, etc.), antineoplastic agents (e.g., alemtuzumab, cisplatin, docetaxel, trastuzumab, etc.), antipyretic agents (e.g., acetaminophen, indomethacin, etc.), antipsychotic agents (e.g., risperidone, etc.), anxiolytic agents (e.g., alprazolam, lorazepam, etc.), bronchodilator agents (e.g., carbuterol, epinephrine, etc.), glucocorticoids (e.g., budesonide, prednisolone, etc.), immunosuppressant agents (e.g., alemtuzumab, tacrolimus, etc.), etc. In a further particular embodiment, said POI is selected from the group consisting of acetylsalicylic acid, alpha-atrial natriuretic peptide, arginine vasopressin, atropine, augmerosen, atorvastatin, AVASTIN® (bevacizumab), calcitonins, chorionic gonadotropins, corticotropin, desmopressin, epibatidine, ERBITUX® (cetuximab), exenatide, HERCEPTIN® (trastuzumab), HUMIRA® (adalimumab), HUMULIN®, ketoconazole, lanreotide, lutropin alpha, metoprolol, minoxidil, nesiritide, octreotide, paclitaxel, paracetamol, pegaptanib, recombinant follicle stimulating hormone, recombinant growth factors, REMICADE® (infliximab), RITUXAN® (rituximab), sermorelin, somatotropin, a taxane derivative, taxol, teriparatide acetate, thyrotropin, triclosan, urofollitropin, XOLAIR® (omalizumab), etc. In another embodiment, the POI is selected from the group consisting of actinomycin D, albendazole, aldosterone, alprazolam, amiodarone, amitriptyline, amprenavir, asimadoline, atorvastatin, bunitrolol, buspirone, camptothecin, carbamazepine, carvedilol, celiprolol, cyclosporine A, cimetidine, clotrimazole, colchicine, cortisone, daunorubicin, debrisoquine, dexamethasone, diazepam, digitoxin, digoxin, diltiazem, docetaxel, domperidone, doxorubicin, efavirenz, epirubicin, erythromycin, ergotamine, estradiol, estradiol glucuronide, erlotinib, etoposide, phenytoin, fentanyl, felodipine, phenothiazines, fexofenadine, fluoroquinolones, fluorouracil, FK-506, gentamicin, griseofulvin, hydrocortisone, imatinib, indinavir, itraconazole, ivermectin, ketoconazole, kaempferol, levofloxacin, lidocaine, loperamide, losartan, lovastatin, mebendazole, methylprednisolone, methotrexate, mibefradil, midazolam, nisoldipine, morphine, nelfinavir, nicardipine, nitrendipine, nifedipine, ondansetron, paclitaxel, pentazocine, praziquantel, prednisolone, prednisone, quercetin, quinidine, ranitidine, rapamycin, rifabutin, rifampicin, ritonavir, saquinavir, sirolimus, sulfamethizole, tacrolimus, tamoxifen, talinolol, teniposide, terfenadine, tetracycline, topotecan, triamcinolone, valspodar, verapamil, vinblastine, vincristine, vindesine, zopiclone, and mixtures thereof.

In another particular embodiment, the POI is an excipient, i.e. an inactive substance that can be liquid, solid or semisolid, used as a medium or carrier for the active ingredients of a composition. Illustrative, non-limitative examples of POI acting as an excipient are liquid paraffin or melted lipids such as wax, cotton oil, corn oil, hydrogenated vegetable oil, canola oil, coconut oil, etc. Said POIs are particularly useful in the production of core-shell vesicular nanocapsules and they may be found in the core of said nanocapsules.

A "volatile solvent", as used herein, is a liquid that vaporizes/evaporates easily at room temperature; a volatile solvent usually has high vapor pressure and a lower boiling point compared to water. Similarly, a "non-volatile solvent", as used herein refers to a liquid that does not evaporate easily or evaporates very slowly at room temperature (e.g., PG, PEG400, glycerol); a non-volatile solvent usually has low vapor pressure and higher boiling point than water.

A "water miscible" solvent or liquid, is a solvent or liquid that dissolves completely in water and is difficult to separate from water, e.g., alcohols, etc.

Nanoparticles of the Invention

In an aspect, the invention relates to a nanoparticle, hereinafter referred to as the "nanoparticle of the invention", selected from the group consisting of:

a) a matrix nanosphere which comprises a matrix, said matrix comprising a half ($C_1$-$C_4$) alkyl ester of a poly (methyl vinyl ether-co-maleic anhydride) (PVM/MA) copolymer; and b) a core-shell vesicular nanocapsule which comprises a core and a shell, said shell comprising a half ($C_1$-$C_4$) alkyl ester of a PVM/MA copolymer.

The term "nanoparticle" has been previously defined and refers to a colloidal system of a solid polymeric particle with an average size less than 1 μm, typically between 10 and 900 nm, preferably between 100 and 400 nm, more preferably between 120 and 160 nm, still more preferably around 130-140 nm, formed, in this particular case by polymerization of a half ($C_1$-$C_4$) alkyl ester of a PVM/MA copolymer. The term "nanoparticle", except otherwise indicated, includes matrix nanospheres and core-shell vesicular nanocapsules. In both cases, due to the large specific surface of these systems, the molecules of the POI, if present, may be trapped or adsorbed in the surface of the nanoparticles.

In a particular embodiment, the nanoparticle of the invention is a matrix nanosphere which comprises a matrix, said matrix comprising a half ($C_1$-$C_4$) alkyl ester of a PVM/MA copolymer. In this embodiment, the product of interest can be trapped or encapsulated within the nanosphere or, alternatively, the product of interest can be adsorbed on the surface of the nanosphere.

In another particular embodiment, the nanoparticle of the invention is a core-shell nano-vesicular structure (nanocapsule) which comprises a core and a shell, said shell comprising a half ($C_1$-$C_4$) alkyl ester of a PVM/MA copolymer. The cavity (core or reservoir) can contain the POI in liquid, semisolid or solid form or as a molecular dispersion; this reservoir can be lipophilic or hydrophobic according to the preparation method and raw materials used. This is particularly useful for carrying POIs in the form of a liquid, semisolid or solid state, for example, oils, water-immiscible liquids, organic solutions or suspensions, including oily solutions or suspensions, comprising a POI, aqueous solutions or suspensions comprising the POI, etc. According to this embodiment, the POI can be within the nanocapsule or, alternatively, it can be adsorbed on the surface of the nanocapsule.

In another particular embodiment, the invention provides a combination of at least a matrix nanosphere which comprises a matrix, said matrix comprising a half ($C_1$-$C_4$) alkyl ester of a PVM/MA copolymer, and, at least a core-shell vesicular nanocapsule which comprises a core and a shell, said shell comprising a half ($C_1$-$C_4$) alkyl ester of a PVM/MA copolymer.

Half ($C_1$-$C_4$) alkyl esters of PVM/MA copolymers are known products or can be produced by opening up the anhydride of a PVM/MA copolymer in a suitable alcohol, such as an alcohol containing 1 to 4 carbon atoms. Illustrative, non-limitative, examples of half ($C_1$-$C_4$) alkyl esters of PVM/MA copolymers include those commercialized by ISP under the common trademarks GANTREZ® ES, for example, GANTREZ® ES 225 (monoethyl ester of PVM/MA copolymer), GANTREZ® ES 335I (isopropyl ester of PVM/MA copolymer), and GANTREZ® ES 425 (monobutyl ester of PVM/MA copolymer). Half ($C_1$-$C_4$) alkyl esters of PVM/MA copolymers are water insoluble and can be supplied in alcoholic solutions, for example, in ethanolic solutions [50% (w/v)].

Half ($C_1$-$C_4$) alkyl esters of PVM/MA copolymers have the capacity to adhere to mucosal surfaces for a long time, which offers high residence time in the site of application and a prolonged drug release.

Half ($C_1$-$C_4$) alkyl esters of PVM/MA copolymers are considered as non-toxic compounds in view of the results of some short-term oral toxicity studies ($LD_{50}$>25.6 g/kg for the monoethyl or monobutyl ester of PVM/MA copolymer) as well as in subchronic inhalation studies and are not ocular or dermal irritants. Neither are skin irritants, sensitizers, or photosensitizers when assayed in human volunteers. Monobutyl ester of PVM/MA copolymer was negative for genotoxicity. Monoethyl ester and monobutyl ester of PVM/MA copolymer are safe in a neutralized form as cosmetic ingredients in the present practices of use. In fact, half ($C_1$-$C_4$) alkyl esters of PVM/MA copolymers are considered as GRAS listed material copolymer, function as film formers and hair fixatives (Cosmetic Ingredient Review), and may be used in cosmetics and personal care products marketed in Europe according to the general provisions of the Cosmetics Directive of the European Union. Monobutyl ester of PVM/MA copolymer is used in aerosol and pump hairsprays, styling mousses and setting lotions, eye, face and skin make-up, creams and lotions.

In a particular embodiment, said half ($C_1$-$C_4$) alkyl ester of a PVM/MA copolymer is the monoethyl ester of PVM/MA copolymer or the monobutyl ester of PVM/MA copolymer.

The molecular weight of the half ($C_1$-$C_4$) alkyl esters of PVM/MA can vary within a broad range; in a particular embodiment, the molecular weigth of the half ($C_1$-$C_4$) alkyl esters of PVM/MA is comprised between 10 and 300 kDa, preferably between 50 and 250 kDa, more preferably between 90 and 150 kDa. In a specific embodiment, said half ($C_1$-$C_4$) alkyl ester of a PVM/MA copolymer is the monoethyl ester of PVM/MA copolymer and has a molecular weight comprised between 100 and 150 kDa. In another specific embodiment, said half ($C_1$-$C_4$) alkyl ester of a PVM/MA copolymer is the monobutyl ester of PVM/MA copolymer and has a molecular weight comprised between 90 and 150 kDa.

Due to the large specific surface of the nanoparticles of the invention, the molecules of a product of interest may be trapped or adsorbed in the surface of the nanoparticles. Thus, the nanoparticles of the invention can efficiently incorporate products of interest, such as large or small, hydrophobic or hydrophilic, compounds, having different uses and application, and, thus, they can be potentially applied in different applications (e.g., in pharmaceutical, cosmetic or agricultural compositions, in food products, etc.).

Thus, in a particular embodiment, the nanoparticle of the invention further comprises a product of interest (POI); in this case, the nanoparticle of the invention is occasionally identified in this description as "loaded nanoparticle of the invention". Information related to said POI may be found in the above section ("Definition"). The skilled person in the art will understand that a loaded nanoparticle of the invention can incorporate one or more products of interest (POIs) in the same nanoparticle provided that said POIs are not incompatible each other.

In a particular embodiment, said POI is Ketoconazole, Minoxidil or Triclosan, and the nanoparticle of the invention is a matrix nanosphere wherein the POI is trapped or encapsulated within the nanosphere or, alternatively, it is adsorbed on the surface of the nanosphere.

In another particular embodiment, said POI is an essential oil, such as lemon essential oil, and the nanoparticle of the invention is a core-shell vesicular nanocapsule wherein the POI is trapped or encapsulated within the nanosphere or, alternatively, it is adsorbed on the surface of the nanosphere.

The "copolymer":POI weight ratio, wherein "copolymer" means the copolymer formed by polymerization of the ($C_1$-$C_4$) alkyl ester of a PVM/MA copolymer, in the loaded nanoparticle of the invention may vary within a broad range; nevertheless, in a particular embodiment, the copolymer:POI weight ratio in the loaded nanoparticle of the invention may be comprised between $1:10^{-6}$ and $1:10^6$, preferably between $1:10^{-3}$ and $1:10^3$, and more preferably between 1:0.03 and 1:0.5.

Process for Producing Nanoparticles

In another aspect, the invention relates to a process for producing a matrix nanosphere which comprises a matrix, said matrix comprising a half ($C_1$-$C_4$) alkyl ester of a poly (methyl vinyl ether-co-maleic anhydride) (PVM/MA) copolymer (i.e., a particular embodiment of the nanoparticles of the invention), hereinafter referred to as "process [1] of the invention", which comprises contacting an organic solution or suspension containing a half ($C_1$-$C_4$) alkyl ester of a PVM/MA copolymer with an aqueous medium in order to form said matrix nanospheres. This process [1] of the invention renders "empty" nanoparticles of the invention, i.e., nanoparticles without product of interest (POI), particularly matrix nanospheres wherein the matrix comprises a half ($C_1$-$C_4$) alkyl ester of a PVM/MA copolymer.

The half ($C_1$-$C_4$) alkyl ester of a PVM/MA copolymer is a known product or can be produced by opening up the anhydride of the PVM/MA copolymer (e.g., GANTREZ® AN) in an alcohol. In a particular embodiment, the half ($C_1$-$C_4$) alkyl ester of the PVM/MA copolymer is the monoethyl ester, or the monoisopropyl ester, or the butyl ester of the PVM/MA copolymer.

The organic solvent can be any suitable organic solvent in which the half ($C_1$-$C_4$) alkyl ester of the PVM/MA copolymer can be totally or partially solubilized, preferably a pharmaceutically or cosmetically acceptable organic solvent. Illustrative, non-limitative, examples of organic solvents which can be used within the context of the process [1] of the invention, include alcohols and non-volatile water miscible solvents other than alcohols, and mixtures thereof.

The term "alcohol", as used herein, refers to any organic compound in which a hydroxyl functional group (—OH) is bound to a carbon atom, usually connected to other carbon or hydrogen atoms, and includes alcohols having only one hydroxyl group, e.g., methanol, ethanol, isopropanol, etc., and alcohols containing two or more (multiple) hydroxyl groups), e.g., propylene glycol (PG), poly ethylene glycol (PEG), etc. Methanol, ethanol and isopropanol are volatile alcohols, whereas PG and PEG are non-volatile alcohols which may be present as a liquid (PG) or as a solid depending on the molecular weight (Mw) of the PEG (e.g., PEG6000, PEG10000). Solid solvents (e.g., PEG6000, PEG10000, etc.) can be used, for example, to produce solid pharmaceutical forms for the administration of drugs, such as suppositories, for example, rectal suppositories comprising, e.g., antipyretic drugs, or vaginal suppositories (ovules) comprising, e.g., antifungal agents, among others, and nanoparticles will be formed when the solution or suspension comprising the polymer contacts with a body fluid, e.g., the vaginal fluid.

In a particular embodiment, the organic solvent is a volatile alcohol, such as ethanol. In another particular embodiment, the organic solvent is a non-volatile alcohol, such as PG. In another particular embodiment, the organic solvent comprises a mixture of two or more volatile alcohols. In another particular embodiment, the organic solvent comprises a mixture of two or more non-volatile alcohols. In another particular embodiment, the organic solvent comprises a mixture of at least one volatile alcohol and at least non-volatile alcohol, e.g., a mixture of ethanol and PG.

Alternatively, the organic solvent may be a non-volatile water miscible solvent other than an alcohol. Illustrative, non-limitative, examples of non-volatile water miscible solvents other than alcohols include polyoxyglycerides, e.g., caprylocaproyl polyoxyglycerides, fatty acid derivatives, e.g., their PG or PEG derivatives, etc. The term "caprylocaproyl polyoxyglycerides" refers to a lipid-based surface-active agent. One exemplary caprylocaproyl polyoxyglyceride is PEG-8 caprylic/capric glycerides, marketed as Labrasol® by Gattefosse. Caprylocaproyl polyoxyglycerides are also known as "caprylocaproyl macrogolglycerides".

The concentration of said half ($C_1$-$C_4$) alkyl ester of the PVM/MA copolymer in the copolymer organic solution or suspension can vary within a broad range; nevertheless, in a particular embodiment, the concentration of the half ($C_1$-$C_4$) alkyl ester of the PVM/MA copolymer in said copolymer organic solution or suspension is comprised between 0.01% and 50% (w/v), preferably between 0.1% and 30% (w/v), more preferably between 1% and 15% (w/v), still more preferably between 2% and 10% (w/v); in a specific embodiment, the concentration of the half ($C_1$-$C_4$) alkyl ester of the PVM/MA copolymer in the copolymer organic solution or suspension is about 5% (w/v).

The organic solution or suspension containing a half ($C_1$-$C_4$) alkyl ester of a PVM/MA copolymer can be prepared by dissolving or dispersing said product in the organic solvent. In a particular embodiment, the organic solvent is an alcohol, such as a simple alcohol, for example a volatile simple alcohol, e.g., ethanol, etc., or a polyol, for example a non-volatile polyol, e.g., PG. In another particular embodiment, the organic solvent is a non-volatile water miscible solvent other than an alcohol such as a polyoxyglyceride, for example, a caprylocaproyl macrogol-glyceride, or a fatty acid derivative.

In a specific embodiment, the solvent is an alcohol; thus, if the half ($C_1$-$C_4$) alkyl ester of the PVM/MA copolymer is already in the form of a concentrated alcoholic solution, a diluted alcoholic solution containing the half ($C_1$-$C_4$) alkyl ester of the PVM/MA copolymer at the desired concentration can be prepared simply by adding the necessary amount of alcohol to the concentrated solution in order to achieve the desired concentration. This is the case, for example, of commercial products GANTREZ® ES 225 (monoethyl ester of PVM/MA copolymer), GANTREZ® ES 335I (isopropyl ester of PVM/MA copolymer) and GANTREZ® ES 425 (monobutyl ester of PVM/MA copolymer) which are usually supplied as ethanolic solutions of said esters at a concentration of 50% (w/v); thus, consequently, in order to achieve the desired concentration (e.g., 5% (w/v)), the commercial solution can be diluted by the addition of the necessary amount of absolute ethanol.

According to process [1] of the invention, an organic solution or suspension containing a half ($C_1$-$C_4$) alkyl ester of a PVM/MA copolymer is contacted with an aqueous medium, which acts as a water miscible polymer non-solvent, in order to form the nanoparticles. In a particular embodiment, the aqueous medium comprises water, preferably, distilled or bidistilled water. This step is performed at a suitable temperature, typically comprised between 1° C. and 100° C., preferably between 10° C. and 40° C., more preferably between 15° C. and 25° C. Subsequently, if desired, the suspension of nanoparticles obtained is subjected to a suitable treatment to eliminate the organic solvent. Elimination of the organic solvent can be performed by any conventional method, depending on the nature of the solvent to be removed, known by the skilled person in the art including, for example, evaporation, etc. In a particular embodiment, when the organic solvent is ethanol, the nanoparticles suspension is evaporated, preferably under reduced pressure using a rotavapor, in order to eliminate said alcohol.

Alternatively, nanoparticles, particularly matrix nanospheres, can be produced by removal of the solvent in an hydroalcoholic solution or suspension containing a half ($C_1$-$C_4$) alkyl ester of a PVM/MA copolymer and a water miscible alcohol, preferably a volatile water miscible alcohol, wherein the amount of water is lower than the necessary amount of water to form the nanoparticles; in this embodiment, once a portion of the alcohol is removed, formation of nanoparticles occurs. Assays performed by the inventors have shown that the topical application of an hydroalcoholic solution containing a half ($C_1$-$C_4$) alkyl ester of a PVM/MA copolymer and ethanol, wherein the amount of water was lower than the necessary amount of water to form the nanoparticles, to human skin (about 37° C.), resulted in the formation of nanoparticles on the surface after a portion of ethanol was removed by evaporation as shown by the transformation of the initially transparent solution into an opaque suspension which was indicative of the formation of nanoparticles on the surface of the skin.

Thus, in a particular embodiment, process [1] of the invention, comprises (i) contacting an organic solution or suspension containing a half ($C_1$-$C_4$) alkyl ester of a PVM/MA copolymer, wherein said organic solution or suspension comprises a volatile water miscible solvent, preferably a volatile water miscible alcohol, with an aqueous medium, to render an hydro-organic solution or suspension containing a half ($C_1$-$C_4$) alkyl ester of a PVM/MA copolymer wherein the amount of aqueous medium is lower than the necessary amount of aqueous medium to form the nanoparticles, and (ii) removing at least a portion of said solvent in order to form matrix nanospheres comprising a matrix, wherein the matrix comprises a half ($C_1$-$C_4$) alkyl ester of a PVM/MA copolymer.

The amount of aqueous medium which is necessary to form the nanoparticles depend, among other things, on the concentration of said half ($C_1$-$C_4$) alkyl ester of the PVM/MA copolymer in the hydro-organic solution or suspension containing said copolymer; nevertheless, in a particular embodiment, the ratio aqueous medium (water):alcohol (ethanol) is comprised between 0.01:1 (v/v) and 1000:1 (v/v), preferably between 0.5:1 (v/v) and 10:1 (v/v), more preferably about 2:1 (v/v). In a specific embodiment, nanoparticles are formed after addition of 10 mL water to an alcoholic solution comprising a half ($C_1$-$C_4$) alkyl ester of the PVM/MA copolymer in ethanol at 5% (w/v) [on the contrary, if 5 mL of water were added to 10 mL of the same alcoholic copolymer solution then no nanoparticles would be formed].

The hydro-organic solution or suspension containing a half ($C_1$-$C_4$) alkyl ester of a PVM/MA copolymer in a medium, said medium comprising a volatile water miscible solvent, preferably a volatile water miscible alcohol, and an aqueous medium, wherein the amount of aqueous medium is lower than the necessary amount of aqueous medium to form nanoparticles, constitutes an additional aspect of the present invention. Said hydro-organic solution or suspension can be used to produce nanoparticles, mainly matrix nanospheres wherein said matrix comprises a half ($C_1$-$C_4$) alkyl ester of a PVM/MA copolymer, after removal of the solvent. In a particular embodiment, the solvent is a volatile water miscible alcohol, e.g., ethanol, and the aqueous medium comprises water; in this embodiment, the resulting hydro-organic solution or suspension is particularly useful for its topical application to the skin or hair of a subject wherein nanoparticles are formed on the surface of the skin or hair after a portion of ethanol is evaporated.

Alternatively, said nanoparticles can be produced in situ without the need of subjecting the resulting suspension of nanoparticles to a treatment for removing the organic solvent. For that purpose, the copolymer organic solution or suspension, preferably an organic solution or suspension wherein the copolymer solvent is a non-volatile water miscible solvent (such as a non-volatile water miscible alcohol, e.g., PG, or a non-volatile water miscible solvent other than an alcohol), containing the half ($C_1$-$C_4$) alkyl ester of a PVM/MA copolymer is prepared by mixing said half ($C_1$-$C_4$) alkyl ester of a PVM/MA copolymer with said organic solvent, and then mixing said organic solution or suspension containing the copolymer with an aqueous medium, such as a medium comprising water, for example water, preferably bidistilled water, or a body fluid, for example, gastrointestinal fluid, etc., and, consequently, in situ self-assembled nanoparticles (SANP) are directly formed. In this embodiment, it is not necessary to remove the solvent due to the minimum residual amount of non-volatile water miscible solvent in the SANP compared to the solvent evaporation method. By illustrative, a solution of a half ($C_1$-$C_4$) alkyl ester of a PVM/MA copolymer, such as GANTREZ® ES (wherein GANTREZ® ES means GANTREZ® ES 225, GANTREZ® ES 335I or GANTREZ® ES 425), in PG at 5% (w/v) can be prepared by dissolving 10 g of the ethanolic solution of commercial GANTREZ® ES (50% w/v) in 100 ml of PG; this means that the 5% GANTREZ® ES in PG solution contains 5% (v/v) ethanol. At the time the nanoparticles are formed, 1 ml of the 5% GANTREZ® ES in PG solution is mixed with 10 ml of water, thus the concentration of ethanol is 0.225% (v/v), i.e., a minimal final concentration of ethanol compared to the concentration of ethanol in the nanoparticles suspension obtained according to the solvent removal method previously disclosed before removing ethanol (e.g, by evaporation), wherein the concentration of ethanol may be about 66.66% (v/v). The low ethanol content in the formulation avoids using high ethanol quantities in order to obtain the copolymer solution or suspension and thus can be administered by oral route with acceptable concentration ranges of ethanol (enhance oral bioavailability of drugs) or buccal mucosal routes.

According to this embodiment, if the organic solution or suspension containing the copolymer is a solution or suspension wherein the solvent is a non-volatile water miscible polyol, e.g., PG, and said non-volatile polyol solution or suspension containing the half ($C_1$-$C_4$) alkyl ester of a PVM/MA copolymer is administered as such by a suitable route which allows the contact of said solution or suspension with a body fluid, e.g., via oral, parenteral, rectal, vaginal, or the like, to a subject (e.g., an animal including a human being), then nanoparticles are formed in situ by self-assembly of the half ($C_1$-$C_4$) alkyl ester of a PVM/MA copolymer chains in contact with said suitable body fluid comprising an aqueous medium.

The concentration of the half ($C_1$-$C_4$) alkyl ester of a PVM/MA copolymer in the organic (non-volatile water miscible solvent) solution or suspension containing said copolymer can vary within a broad range; nevertheless, in a particular embodiment, the concentration of the copolymer formed by copolymerization of the half ($C_1$-$C_4$) alkyl ester of the PVM/MA copolymer in said copolymer organic solution or suspension is comprised between 0.01% and 50% (w/v), preferably between 0.1% and 30% (w/v), more preferably between 1% and 15% (w/v), still more preferably between 2% and 10% (w/v); in a specific embodiment, the concentration of the half ($C_1$-$C_4$) alkyl ester of the PVM/MA copolymer in the copolymer organic solution is about 5% (w/v).

In another aspect, the invention relates to a process for producing a matrix nanosphere which comprises a product of interest (POI), wherein said matrix nanosphere comprises a matrix, said matrix comprising a half ($C_1$-$C_4$) alkyl ester of a poly (methyl vinyl ether-co-maleic anhydride) (PVM/MA) copolymer (i.e., a particular embodiment of the nanoparticles of the invention), hereinafter referred to as "process [2] of the invention", which comprises:

[A] contacting an alcoholic or hydroalcoholic solution or suspension comprising said POI and said half ($C_1$-$C_4$) alkyl ester of the PVM/MA copolymer with an aqueous medium; or, alternatively,

[B] contacting an alcoholic solution or suspension comprising said POI and said half ($C_1$-$C_4$) alkyl ester of the PVM/MA copolymer with an aqueous medium.

Process [2] of the invention renders "loaded" nanoparticles of the invention, namely, matrix nanospheres loaded with at least a product of interest (POI).

According to option [A] of the process [2] of the invention, an alcoholic or hydroalcoholic solution or suspension comprising a POI and a half ($C_1$-$C_4$) alkyl ester of the PVM/MA copolymer is contacted with an aqueous medium. This option [A] is particularly useful when the POI is a hydrophilic compound or an amphiphilic compound (in this case, the percentage of water should be adjusted). Briefly, an alcoholic or hydroalcoholic solution or suspension comprising a POI and a half ($C_1$-$C_4$) alkyl ester of the PVM/MA copolymer may be obtained by conventional means known by the skilled person in the art, for example, by mixing an alcoholic solution or suspension of said POI (obtainable by dissolving or suspending the POI in a suitable alcohol), or alternatively, an aqueous solution or suspension of said POI (obtainable by dissolving or suspending the POI in an aqueous medium, for example, a medium comprising water, preferably, water), with an alcoholic solution of said half ($C_1$-$C_4$) alkyl ester of the PVM/MA copolymer under suitable conditions to obtain said alcoholic or hydroalcoholic solution or suspension comprising a POI and a half ($C_1$-$C_4$) alkyl ester of the PVM/MA copolymer. Illustrative, non-limitative, examples of said operation conditions include stirring, at room temperature, for a suitable period of time, for example, from 1 to 30 minutes, typically, less than 15 minutes, preferably around 5 minutes.

The particulars of the POI have been previously mentioned in the "Definitions" section. The particulars of the half ($C_1$-$C_4$) alkyl ester of a PVM/MA copolymer have been previously mentioned in connection with the process [1] of the invention as well as the particulars of the alcoholic solution of a half ($C_1$-$C_4$) alkyl ester of a PVM/MA copolymer, e.g., alcohols, concentration, etc. In a particular embodiment, the alcohol present in the alcoholic solution is ethanol or a polyol such as PG.

According to option [A] of the process [2] of the invention, an alcoholic or hydroalcoholic solution or suspension comprising a POI and a half ($C_1$-$C_4$) alkyl ester of the PVM/MA copolymer is contacted with an aqueous medium, i.e., a medium comprising water, which acts as a water miscible polymer non-solvent, in order to form the nanoparticles loaded with said POI ("POI-loaded nanoparticles"). The volume ratio between the copolymer solvent (alcohol, e.g., ethanol) and the non-solvent (e.g., water) [solvent:non-solvent] can vary within a broad range, typically between 1:0.001 (v/v) and 1:5000 (v/v), preferably between 1:0.5 (v/v) and 1:1 (v/v). However, if the alcoholic or hydroalcoholic solution or suspension comprising a POI and a half ($C_1$-$C_4$) alkyl ester of the PVM/MA copolymer is contacted with an aqueous medium "in defect", i.e., wherein the amount of water is lower than the necessary amount of water to form the nanoparticles, it is also possible to form the POI-loaded nanoparticles by removing at least a portion of the alcohol, such as it was mentioned previously in connection with a particular embodiment of process [1] of the invention; in this case, the alcohol should be, preferably, a volatile water miscible alcohol, such as, for example, ethanol. This embodiment could be useful for preparing compositions, e.g., cosmetic or pharmaceutical compositions, to deliver POI via topical application thereof.

Thus, in a particular embodiment, process [2] of the invention, comprises (i) contacting an alcoholic or hydroalcoholic solution or suspension comprising a POI and a half ($C_1$-$C_4$) alkyl ester of the PVM/MA copolymer, wherein said solution or suspension comprises a volatile water miscible alcohol, with an aqueous medium, to render an hydro-alcoholic solution or suspension containing a half ($C_1$-$C_4$) alkyl ester of a PVM/MA copolymer wherein the amount of aqueous medium is lower than the necessary amount of aqueous medium to form the nanoparticles, and (ii) removing at least a portion of said alcohol in order to form matrix nanospheres comprising a matrix, wherein the matrix comprises a half ($C_1$-$C_4$) alkyl ester of a PVM/MA copolymer.

The hydroalcoholic solution or suspension containing a half ($C_1$-$C_4$) alkyl ester of a PVM/MA copolymer and a POI in a medium, said medium comprising a volatile water miscible alcohol and an aqueous medium, wherein the amount of aqueous medium is lower than the necessary amount of aqueous medium to form nanoparticles, constitutes an additional aspect of the present invention. Said hydro-organic solution or suspension can be used to produce POI-loaded nanoparticles, mainly matrix nanospheres wherein said matrix comprises a half ($C_1$-$C_4$) alkyl ester of a PVM/MA copolymer, after removal of the alcohol. In a particular embodiment, the alcohol is ethanol, and the aqueous medium comprises water; in this embodiment, the resulting hydroalcoholic solution or suspension is particularly useful for its topical application to the skin or hair of a subject wherein nanoparticles are formed on the surface of the skin or hair after a portion of ethanol is evaporated.

The step of contacting said alcoholic or hydroalcoholic solution or suspension comprising said POI and said half ($C_1$-$C_4$) alkyl ester of a PVM/MA copolymer with the aqueous medium is performed at a suitable temperature, typically comprised between 1° C. and 100° C., preferably, between 10° C. and 40° C., and more preferably between 15° C. and 25° C. Subsequently, if necessary, the suspension of POI-loaded nanoparticles so obtained is subjected to a suitable treatment to eliminate the alcohol in order to obtain an aqueous suspension of POI-loaded nanoparticles. Elimination of the alcohol can be performed by conventional methods known by the skilled person in the art including, for example, evaporation, etc.; in a particular embodiment, the POI-loaded nanoparticles suspension is evaporated, preferably under reduced pressure using a rotavapor, to eliminate ethanol.

According to option [B] of the process [2] of the invention, an alcoholic solution or suspension comprising a POI and a half ($C_1$-$C_4$) alkyl ester of the PVM/MA copolymer is contacted with an aqueous medium. This option [B] is particularly useful when the POI is a hydrophobic or an amphiphilic compound. Briefly, an alcoholic suspension comprising a POI and a half ($C_1$-$C_4$) alkyl ester of the PVM/MA copolymer is obtained by mixing said POI with an alcoholic solution of said half ($C_1$-$C_4$) alkyl ester of the PVM/MA copolymer under suitable conditions to obtain said alcoholic suspension comprising a POI and a half ($C_1$-$C_4$) alkyl ester of the PVM/MA copolymer, Illustrative, non-limitative, examples of said operation conditions include stirring, at room temperature, for a suitable period of time, for example, from 1 to 30 minutes.

The particulars of the POI have been previously mentioned in the "Definitions" section. The particulars of the half ($C_1$-$C_4$) alkyl ester of a PVM/MA copolymer have been previously mentioned in connection with the process [1] of the invention as well as the particulars of the alcoholic solution of a half ($C_1$-$C_4$) alkyl ester of a PVM/MA copolymer, e.g., alcohols, concentration, etc. In a particular embodiment, the alcohol present in the alcoholic solution is ethanol or a polyol such as propylene glycol (PG).

According to option [B] of the process [2] of the invention, an alcoholic suspension comprising a POI and a half ($C_1$-$C_4$) alkyl ester of the PVM/MA copolymer is contacted with an aqueous medium, i.e., a medium comprising water, which acts as a water miscible polymer non-solvent, in order to form the nanoparticles loaded with said POI ("POI-loaded nanoparticles"). In a particular embodiment, the aqueous medium comprises water, preferably, distilled or bidistilled water. The volume ratio between the copolymer solvent (alcohol, e.g., ethanol or PG) and the non-solvent (e.g., water) [solvent:non-solvent] can vary within a broad range, typically between 1:0.001 (v/v) and 1:5000 (v/v), preferably between 1:0.5 (v/v) and 1:1 (v/v). This step of contacting said alcoholic solution or suspension comprising said POI and said half ($C_1$-$C_4$) alkyl ester of a PVM/MA copolymer with the aqueous medium is performed at a suitable temperature, typically comprised between 1° C. and 100° C., preferably, between 10° C. and 40° C., and more preferably between 15° C. and 25° C. Subsequently, if desired, the suspension of POI-loaded nanoparticles so obtained is subjected to a suitable treatment to eliminate the alcohol in order to obtain an aqueous suspension of POI-loaded nanoparticles as previously mentioned in connection with option [A] of the process [2] of the invention. When the solvent is PG it is not necessary to remove it since it can be used in human by oral route.

Alternatively, due to the possibility of the half ($C_1$-$C_4$) alkyl ester of the PVM/MA copolymer to form in situ self-assembled nanoparticles (SANP), the invention provides an additional process for producing a matrix nanosphere which comprises a product of interest (POI), wherein said matrix nanosphere comprises a matrix, said matrix comprising a half ($C_1$-$C_4$) alkyl ester of a poly (methyl vinyl ether-co-maleic anhydride) (PVM/MA) copolymer (i.e., a particular embodiment of the nanoparticles of the invention), hereinafter referred to as "process [3] of the invention", which comprises contacting an organic solution or suspension comprising said POI and said half ($C_1$-$C_4$) alkyl ester of the PVM/MA copolymer, with an aqueous medium, wherein said organic solution or suspension comprises a non-volatile water miscible solvent.

Process [3] of the invention renders "loaded" nanoparticles of the invention, namely, in situ self-assembled matrix nanospheres loaded with at least a POI.

According to the process [3] of the invention, an organic solution or suspension comprising a POI and a half ($C_1$-$C_4$) alkyl ester of the PVM/MA copolymer in a non-volatile water miscible solvent is contacted with an aqueous medium. This process is particularly useful when the POI is a hydrophobic, hydrophilic or amphiphilic compound. Briefly, an organic solution or suspension comprising a POI and a half ($C_1$-$C_4$) alkyl ester of the PVM/MA copolymer in a non-volatile water miscible solvent is obtained by mixing a solution or suspension of said POI (obtainable by dissolving or dispersing the POI in a non-volatile water miscible solvent) with a solution or suspension of said half ($C_1$-$C_4$) alkyl ester of the PVM/MA copolymer in a non-volatile water miscible solvent, under suitable conditions to obtain said solution or suspension comprising a POI and a half ($C_1$-$C_4$) alkyl ester of the PVM/MA copolymer in a non-volatile water miscible. Illustrative, non-limitative, examples of said operation conditions include stirring, at room temperature, for a suitable period of time, for example, from 1 to 30 minutes, typically, less than 15 minutes, preferably around 5 minutes. Although the solvents of said solutions or suspensions, the solution or suspension of the POI and the solution or suspension of the half ($C_1$-$C_4$) alkyl ester of the PVM/MA copolymer, may be different, in practice, it is preferred that the solvent of both solutions or suspensions is the same; in a particular embodiment, said solvent is a polyol such as PG.

The particulars of the POI have been previously mentioned in the "Definitions" section. The particulars of the half ($C_1$-$C_4$) alkyl ester of a PVM/MA copolymer have been previously mentioned in connection with the process [1] of the invention.

As mentioned above, the solvent may be any suitable solvent, such as a non-volatile water miscible solvent, in which the half ($C_1$-$C_4$) alkyl ester of the PVM/MA copolymer can be totally or partially solubilized, preferably a pharmaceutically or cosmetically acceptable non-volatile water miscible solvent. Illustrative, non-limitative, examples of non-volatile water miscible solvents which can be used within the context of the process [3] of the invention, include non-volatile water miscible alcohols, for example, PG, PEG, etc., non-volatile water miscible solvents other than alcohols, such as polyoxyglycerides, e.g., caprylocaproyl polyoxy-glycerides (Labrasol®), fatty acid derivatives, e.g., their PG or PEG derivatives, etc., and any mixture thereof, for example, a mixture of two or more non-volatile water miscible alcohols, a mixture of two or more non-volatile water miscible solvents other than alcohols, or a mixture of at least one non-volatile water miscible alcohol and at least one non-volatile water miscible solvent other than an alcohol.

The concentration of said half ($C_1$-$C_4$) alkyl ester of the PVM/MA copolymer in the solution or suspension comprising said POI and said non-volatile water miscible solvent can vary within a broad range; nevertheless, in a particular embodiment, the concentration of the half ($C_1$-$C_4$) alkyl ester of the PVM/MA copolymer in said solution or suspension is comprised between 0.01% and 50% (w/v), preferably between 0.1% and 30% (w/v), more preferably between 1% and 15% (w/v), still more preferably between 2% and 10% (w/v); in a specific embodiment, the concentration of the half ($C_1$-$C_4$) alkyl ester of the PVM/MA copolymer in the copolymer organic solution or suspension is about 5% (w/v).

According to process [3] of the invention, an solution or suspension comprising a POI and a half ($C_1$-$C_4$) alkyl ester of the PVM/MA copolymer in a non-volatile water miscible solvent is contacted with an aqueous medium, i.e., a medium comprising water, to form the nanoparticles loaded with said POI ("POI-loaded nanoparticles") by in situ self-assembly of the copolymer chains. In a particular embodiment, the aqueous medium comprises water, preferably, distilled or bidistilled water. This step is performed at a suitable temperature, typically comprised between 1° C. and 100° C., preferably, between 10° C. and 40° C., and more preferably between 15° C. and 25° C.

In another aspect, the invention relates to a process for producing a core-shell vesicular nanocapsule which comprises a product of interest (POI), wherein said core-shell vesicular nanocapsule comprises a core and a shell, wherein said shell comprises a half ($C_1$-$C_4$) alkyl ester of a PVM/MA copolymer (i.e., a particular embodiment of the nanoparticles of the invention), hereinafter referred to as "process [4] of the invention", which comprises contacting a solution or suspension comprising said POI and said half ($C_1$-$C_4$) alkyl ester of a PVM/MA copolymer with an aqueous medium. In a particular embodiment, the solution or suspension comprising a POI and a half ($C_1$-$C_4$) alkyl ester of a PVM/MA copolymer is contacted with the aqueous medium in the presence of a surfactant.

Process [4] of the invention renders "loaded" nanoparticles of the invention, namely, core-shell vesicular nanocapsules loaded with at least a POI. The POI can be within the nanocapsule or adsorbed on the surface of the shell nanocapsule. The POI may be in a liquid, semi-solid or solid state. In a particular embodiment, said POI is an oil. In another particular embodiment, said POI is dissolved or dispersed in a water immiscible solvent. In another particular embodiment, said POI is a drug or a cosmetical product in the form of an oily solution or suspension or in the form of a solution or dispersion in a water immiscible solvent.

According to process [4] of the invention, a solution or suspension comprising a POI and a half ($C_1$-$C_4$) alkyl ester of a PVM/MA copolymer is contacted with an aqueous medium in the presence of a surfactant. This process is particularly useful when the POI is a hydrophobic, hydrophilic or amphiphilic compound.

Briefly, a solution or suspension comprising a POI and a half ($C_1$-$C_4$) alkyl ester of the PVM/MA copolymer is obtained by mixing (i) a POI, (ii) an alcohol, and (iii) an alcoholic solution of said half ($C_1$-$C_4$) alkyl ester of the PVM/MA copolymer under suitable conditions to obtain said solution or suspension comprising a POI and a half ($C_1$-$C_4$) alkyl ester of the PVM/MA copolymer.

The alcohol to be mixed with both the POI and the alcoholic solution of said half ($C_1$-$C_4$) alkyl ester of the PVM/MA copolymer, in a particular embodiment, may be the same or, preferably, different from the alcohol which forms the alcoholic solution of said half ($C_1$-$C_4$) alkyl ester of the PVM/MA copolymer. Illustrative, non-limitative, examples of said alcohol include virtually any alcohol, preferably a pharmaceutically or cosmetically acceptable alcohol, e.g., a simple alcohol such as ethanol, etc., or a polyol, e.g., PG, PEG, etc., or any mixture of simple alcohols, polyols, or both at least one simple alcohol and at least one polyol. The use of mixtures of alcohols may be convenient depending, among other features, of the solubility of the half ($C_1$-$C_4$) alkyl ester of the PVM/MA copolymer in the mixtures of the liquid phase comprising the POI (e.g., an oil, a solution or suspension of the POI in a water immiscible solvent, etc.) and the alcohol (or mixture thereof). In a particular embodiment, the alcohol to be mixed with both the POI and the alcoholic solution of said half ($C_1$-$C_4$) alkyl ester of the PVM/MA copolymer is ethanol, PG, etc., preferably PG (when the liquid phase comprising the POI is highly soluble in PG), or a mixture of ethanol and PG, and the alcohol which forms the alcoholic solution of said half ($C_1$-$C_4$) alkyl ester of the PVM/MA copolymer is a simple alcohol, such as ethanol, etc.

Illustrative, non-limitative, examples of the operation conditions to obtain the solution or suspension comprising a POI and a half ($C_1$-$C_4$) alkyl ester of the PVM/MA copolymer include stirring, at room temperature, for a suitable period of time, for example, from 1 to 30 minutes, typically, less than 15 minutes, preferably around 5 minutes.

The POI:copolymer weight ratio, wherein "copolymer" refers to the alcoholic solution or suspension of the copolymer, can vary within a broad range; nevertheless, in a particular embodiment, said POI:copolymer ratio, by weight, is comprised between 0.001:1 and 100:1, preferably between 0.01:1 and 1:1, more preferably between 0.02:1 and 0.05:1.

The particulars of the POI have been previously mentioned in the "Definitions" section; nevertheless, in this case, the POI should be in the form of a solution or suspension in a water immiscible liquid. Thus, in a particular embodiment, the POI is an oil, for example, an essential oil. In another particular embodiment, the POI is dissolved or dispersed in a water immiscible solvent, for example, in an oil thus forming an oily solution or suspension, etc. Thus, virtually any POI capable of being dissolved or dispersed in a water immiscible liquid can be used within the context of process [4] of the invention. In a specific embodiment, said POI is a drug or a cosmetical product in the form of an oily solution or suspension or in the form of a solution or dispersion in a water immiscible solvent.

The particulars of the half ($C_1$-$C_4$) alkyl ester of a PVM/MA copolymer have been previously mentioned in connection with the process [1] of the invention as well as the particulars of the alcoholic solution of a half ($C_1$-$C_4$) alkyl ester of a PVM/MA copolymer, e.g., alcohols, concentration, etc. In a particular embodiment, the alcohol present in the alcoholic solution of said half ($C_1$-$C_4$) alkyl ester of the PVM/MA copolymer is ethanol and the alcohol to be mixed with the POI and with said ethanolic solution of the half ($C_1$-$C_4$) alkyl ester of the PVM/MA copolymer is a polyol, preferably PG.

According to process [4] of the invention, a water immiscible solution or suspension comprising a POI and a half ($C_1$-$C_4$) alkyl ester of the PVM/MA copolymer, e.g., an oily solution or suspension, is contacted with an aqueous medium, i.e., a medium comprising water, non-solvent, optionally in the presence of a surfactant, in order to form the core-shell vesicular nanocapsules loaded with said POI ("POI-loaded shell core-shell vesicular nanocapsules"). In a particular embodiment, the aqueous medium comprises water, preferably, distilled or bidistilled water. The volume ratio of the (alcoholic solution or suspension comprising the POI and the copolymer):aqueous phase can vary within a broad range, for example, between 1:500: and 1:1000 (v/v), preferably between 1:5: and 1:10.

Although it is not necessary to use surfactants for producing the core shell nanocapsules provided by the instant invention, in practice it may be of interest to use a surfactant, e.g., a hydrophilic, hydrophobic or mixtures thereof, in order to obtain the suitable HLB. Illustrative, non-limitative, examples of surfactants which can be used within the context of the present invention include non-ionic surfactants, for example, polysorbates (i.e., oily liquids derived from pegylated sorbitan esterified with fatty acids, e.g., lauric acid, palmitic acid, stearic acid, oleic acid, etc.; esters of plain (non-PEG-ylated) sorbitan with fatty acids are usually referred to by the name "Span"), polyoxyethylene derivative of sorbitan monolaurate (TWEEN® 20), polyoxyethylene derivative of sorbitan oleate (TWEEN® 80), etc., anionic surfactants, e.g., sodium dodecyl sulfate (SDS), etc., block copolymers based on ethylene oxide and propylene oxide commercialized as PLURONICS® by BASF, polyvinylic alcohol (PVA), etc. In a particular embodiment, the surfactant is TPGS (alpha-tocopheryl succinate esterified to PEG1000). The amount of the surfactant can vary within a broad range; nevertheless, in a particular embodiment, the concentration of surfactant is comprised between 0.001% and 50% (w/v), preferably between 0.01% and 10% (w/v), more preferably between 0.05% and 5% (w/v).

Further, the volume ratio of the (alcoholic solution or suspension comprising the POI and the copolymer): aqueous phase can vary within a broad range, for example, between 1:500 and 1:1000 (v/v), preferably between 1:5 and 1:10.

This step is performed at a suitable temperature, typically comprised between 1° C. and 100° C., preferably, between 15° C. and 50° C.

If desired, the nanoparticles of the invention, both those that are loaded with a POI (POI-loaded nanoparticles) and those that are not loaded ("empty" nanoparticles), may incorporate an antioxidant, e.g., ascorbic acid (vitamin C), etc., in their formulation for the purpose of increasing their stability with regard to temperature and oxidation. In this case, said antioxidant could be co-encapsulated with the POI (where appropriate) or in the coating of the nanoparticles of the invention; to that end, said processes [1] to [4] of the invention will be suitably adapted to incorporate the antioxidant in the formulation of the nanoparticles, for example, by adding the antioxidant to the aqueous medium used for producing the nanoparticles.

Additionally, if desired, said process [1], [2], [3] and [4] of the invention may include a drying step for drying the suspension containing the nanoparticles so formed, in order to obtain the nanoparticles of the invention, i.e., both the POI-loaded nanoparticles and the "empty" nanoparticles, in the form of a powder. This form of presentation of said nanoparticles contributes to their stability and is further particularly useful for their eventual application in solid foods, such as flour, bread, pastry products, cereals, milk powder, etc., as well as in cosmetic and/or pharmaceutical compositions and products.

Virtually any conventional technique or method suitable for drying suspensions containing nanoparticles can be used to perform this drying step; however, in a particular embodiment, the drying of the suspension containing nanoparticles is carried out by means of spray drying or by means of lyophilization. This treatment is generally carried out by adding a suitable protective agent of said nanoparticles, such as a saccharide, for example, lactose, trehalose, mannitol, sucrose, maltodextrine, glucose, sorbitol, maltose, etc., and mixtures thereof to the suspension of the nanoparticles. Said protective agent protects the nanoparticles of the invention against heat degradation as well as oxidation during the drying process.

The "half ($C_1$-$C_4$) alkyl ester of the PVM/MA copolymer: saccharide" ratio by weight may vary within a broad range; however, in a particular embodiment, the "half ($C_1$-$C_4$) alkyl ester of the PVM/MA copolymer:saccharide" by weight is comprised between 1 and 1000, preferably about 1:1-5.

Likewise, in a particular embodiment, the solution containing the saccharide could further contain an antioxidant agent, such as ascorbic acid (vitamin C), etc.; in this case, the "half ($C_1$-$C_4$) alkyl ester of the PVM/MA copolymer:saccharide: antioxidant agent", ratio by weight could be from 1:0.01-1000:0.001-100, preferably about 1:5:0.2.

As mentioned above, the skilled person in the art will understand that a loaded nanoparticle of the invention can incorporate one or more POI in the same nanoparticle provided that said POIs are not incompatible each other. To that end, process [1], [2], [3] and [4] will be properly modified to incorporate the POIs in the same alcoholic (or oily) solution comprising the half ($C_1$-$C_4$) alkyl ester of the PVM/MA copolymer or in the same hydroalcoholic solution or suspension comprising the half ($C_1$-$C_4$) alkyl ester of the PVM/MA copolymer, or, alternatively, in different preparations.

The nanoparticles of the invention obtained according to process [1], [2], [3] or [4] of the invention constitute an additional aspect of the present invention.

Applications

The nanoparticles of the invention have a lot of properties which make them potentially useful in a lot of industries, for example, in the pharmaceutical, cosmetic, agricultural or food industries, as a system for the delivery of products of interest to different surfaces, e.g., buccal, gastrointestinal tract, hair, nasal, oral, rectal, skin, vaginal, etc.

Illustrative, non-limitative, examples of said properties of the nanoparticles of the invention include high mucosal bioadhesion, high long-term stability in an aqueous medium, high encapsulation efficiency of products of interest, such as small or large, hydrophilic, hydrophobic or amphiphilic, compounds, high encapsulation efficiency of oils, and/or enhancer of the solubility in water of hydrophobic compounds.

In a particular embodiment, the nanoparticles of the invention allow the incorporation of a POI, in agricultural, cosmetic, food or pharmaceutical composition.

The nanoparticles of the invention can be presented in the form of a suspension, preferably in an aqueous medium, or, alternatively, they can be presented in the form of a dry powder, maintaining the POI in a stable condition and enabling its storage for long periods of time (particularly, for its incorporation in solid food preparations).

Therefore, in another aspect, the invention relates to a composition, hereinafter "composition of the invention", comprising at least one nanoparticle of the invention and an agricultural, cosmetically or pharmaceutically acceptable carrier or a carrier suitable for food.

In a particular embodiment, the nanoparticle of the invention is an "empty" nanoparticle of the invention, i.e., a nanoparticle of the invention without a POI, such as (i) a matrix nanosphere which comprises a matrix, said matrix comprising a half ($C_1$-$C_4$) alkyl ester of a PVM/MA copolymer, (ii) a core-shell vesicular nanocapsule which comprises a core and a shell, said shell comprising a half ($C_1$-$C_4$) alkyl ester of a PVM/MA copolymer, or (iii) a combination of (i) and (ii).

In another particular embodiment, the nanoparticle of the invention is a "loaded" nanoparticle of the invention, i.e., a nanoparticle of the invention loaded with a POI, such (i) a matrix nanosphere which comprises a POI and a matrix, said matrix comprising a half ($C_1$-$C_4$) alkyl ester of a PVM/MA copolymer, (ii) a core-shell vesicular nanocapsule which comprises a POI in the core and a shell, said shell comprising a half ($C_1$-$C_4$) alkyl ester of a PVM/MA copolymer, or (iii) a combination of (i) and (ii). In a particular embodiment, said POI is a POI having agricultural, cosmetic, nutritional, and/or therapeutic activity. The particulars of said POI have been mentioned in the "Definitions" section.

In another particular embodiment, the composition of the invention is an agricultural composition; to that end, said composition comprises a "loaded" nanoparticle of the invention comprising a POI susceptible of being used in the agricultural field, in the broadest sense, for example, a phytosanitary product for controlling pests and pathogens, a plant growth promoting agent, etc., for example, herbicides (glyphosate, etc.), insecticides (e.g., lambda-cyhalothrin, etc.), fungicides (e.g., Mancozeb), etc, and an agriculturally acceptable carrier comprising one or more excipients suitable for its application; the agricultural composition can be formulated in the form of a gel, suspension, etc., by using the carriers known by the skilled person in the art.

In another particular embodiment, the composition of the invention is a cosmetic composition; to that end, said composition comprises "empty" nanoparticles of the invention, e.g., empty nanoparticles for use in hair styling products such as hair fixatives, styling, etc., or "loaded" nanoparticles of the invention comprising a POI having cosmetic activity or susceptible of being used with cosmetic purposes, or mixtures thereof, and a cosmetically acceptable carrier comprising one or more excipients suitable for its administration by a suitable route, such as, for example, by the topical route; the cosmetic composition can be formulated in the form of skin-care creams, lotions, powders, perfumes, lipsticks, fingernail and toe nail polish, eye and facial makeup, towelettes, permanent waves, colored contact lenses, hair colors, hair sprays and gels, deodorants, hand sanitizer, baby products, bath oils, bubble baths, bath salts, suspensions, butters and many other types of products. Information about excipients suitable for the formulation of cosmetic compositions as well as about the production of said cosmetic compositions can be found in the book "Manual de Cosmetologia", by Octavio Diez Sales, $1^{st}$ Edition, 1998, Editorial Videocinco, S.A. Illustrative, non-limitative, examples of POI used in the cosmetic industry include the products already mentioned in the "Definitions" section.

In another particular embodiment, the composition of the invention is a food composition, such as a solid, liquid or semi-solid food preparation; to that end, said composition comprises a "loaded" nanoparticle of the invention comprising a POI having nutritional activity and a carrier for use in food. Alternatively, the composition of the invention can be incorporated into a foodstuff; therefore, in another aspect, the invention relates to a foodstuff comprising a composition of the invention, namely, a composition which comprises a "loaded" nanoparticle of the invention, said nanoparticle comprising a POI having nutritional activity and a carrier for use in food. The foodstuff can be found in liquid, semi-solid or solid form. Illustrative examples of foodstuffs that can be enriched or fortified with the composition of the invention include milk and derivatives thereof (yoghurts, cheeses, curds, etc.), juices, jams, bakery and pastry products, fermented meat, sauces, etc. Similarly, the composition of the invention can be incorporated into an animal food product, for example, in feeds.

In another particular embodiment, the composition of the invention is a pharmaceutical composition; to that end, said composition comprises a "loaded" nanoparticle of the invention comprising a POI having therapeutic activity or susceptible of being used with therapeutic purposes, and a pharmaceutically acceptable carrier which comprises one or more excipients or vehicles.

The POI which is present in the "loaded" nanoparticle of the invention can be trapped or encapsulated within the nanoparticle (i.e., nanosphere or nanocapsule) or, alternatively, the product of interest can be adsorbed on the surface of the nanoparticle.

Examples of pharmaceutical compositions include liquid, solid or semi-solid compositions.

The pharmaceutical compositions will comprise suitable excipients for each formulation and will be conventionally prepared by methods known by the persons skilled in the art. The excipients will be chosen according to the selected pharmaceutical dosage form. A review of the different pharmaceutical dosage forms of drugs and of their preparation can be found in the book "Tratado de Farmacia Galénica", by C. Faulí i Trillo, 10 Edition, 1993, Luzán 5, S.A. de Ediciones.

The proportion of the POI incorporated in the "loaded" nanoparticle of the invention can vary within a broad range; nevertheless, in a particular embodiment, the weight/weight ratio copolymer:POI is comprised between $1:10^{-6}$ and $1:10^{6}$, preferably between $1:10^{-3}$ and $1:10^{3}$, more preferably between 1:0.03 and 1:0.5. Nevertheless, the suitable proportion will depend on each case of the POI incorporated.

The dose of "loaded" nanoparticles of the invention to be administered to a subject in need of treatment with the POI can vary within a broad range and will depend, among other features, on the nature of the POI, its activity or potency, the amount of POI per nanoparticles, etc.; only by illustrative purposes, the dose of "loaded" nanoparticles to be administered to a subject may be comprised, for example, between approximately 0.01 and approximately 10 mg per kg of body weight, preferably, between 0.1 and 2 mg per kg of body weight.

In a particular embodiment, said pharmaceutical composition is formulated as a pharmaceutical dosage form suitable for its administration by any suitable route, for example, by the buccal, dental, nasal, ocular, oral, parenteral, rectal, topical, or vaginal router Illustrative, non-limitative, examples of said pharmaceutical dosage forms include solid (e.g., soft or hard gelatin and non-gelatin capsules, adhesive films, dental adhesives parches, suppositories, tablets, granules, microparticles, etc.), semisolids (e.g., creams, gels, lotions, ointments, etc.), liquids (e.g., solutions suspensions, etc.). In a preferred embodiment, due to the bioadhesive properties of the nanoparticles of the invention, the pharmaceutical composition is formulated in the form of a composition for its administration through a route of access to mucosae.

In a specific embodiment, the pharmaceutical composition is formulated as a pharmaceutical form suitable for its administration by the rectal route (suppositories) or by the vaginal route (ovules); if desired, in this embodiment, the nanoparticles can be formed when the solution or suspension comprising the polymer contacts with a body fluid, e.g., the vaginal fluid.

In another particular embodiment, the pharmaceutical composition is prepared in the form of a dry powder, for example as a lyophilizate, together with a cryoprotecting agent, to be reconstituted before use by mixing with the reconstitution agent.

In a specific embodiment, the invention provides a pharmaceutical composition comprising:

| Component | % by weight with respect to total |
|---|---|
| Half ($C_1$-$C_4$) alkyl ester of a PVM/MA copolymer | 0.01-99.98 |
| POI | 0.01-99.98 |
| Excipients | 0.01-15.00 |

The "loaded" nanoparticles of the invention, in particular, those nanoparticles loaded with a POI wherein said POI is a drug, can be used in the treatment of diseases. The drug will be elected in function of the disease to be treated. Therefore, in another aspect, the invention relates to the use of a nanoparticle of the invention loaded with a POI, wherein said POI is a drug, in the manufacture of a medicament for the treatment of a disease, or, alternatively, the invention relates to a nanoparticle of the invention loaded with a POI, wherein said POI is a drug, for use as a medicament or in the treatment of a disease.

In a particular embodiment, the drug is Minoxidil, and, thus, the invention relates to the use of a nanoparticle of the invention loaded with Minoxidil in the manufacture of a medicament for the treatment of hair loss (alopecia), or, alternatively, in other words, a nanoparticle of the invention loaded with Minoxidil for use in the treatment of hair loss (alopecia).

In a particular embodiment, the drug is Triclosan or Ketoconazole, and, thus, the invention relates to the use of a nanoparticle of the invention loaded with Triclosan or Ketoconazole in the manufacture of a medicament for the treatment of buccal infection, or, alternatively, in other words, a nanoparticle of the invention loaded with Triclosan or Ketoconazole for use in the treatment of buccal infection.

Since the nanoparticles of the invention may be formed in situ, another aspect of the invention is a composition comprising:

i. a solution or suspension containing a half ($C_1$-$C_4$) alkyl ester of a poly (methyl vinyl ether-co-maleic anhydride) (PVM/MA) copolymer and a product of interest in a medium, said medium comprising a volatile water miscible alcohol and an aqueous medium, wherein the amount of aqueous medium is lower than the necessary amount of aqueous medium to form nanoparticles; and ii. a carrier.

The invention is described below by means of several examples which do not limit, but rather illustrate the invention.

EXAMPLES

The following examples describe the production of nanoparticles (matrix nanospheres and shell nanocapsules), based on a half ($C_1$-$C_4$) alkyl ester of a PVM/MA copolymer, that may incorporate a product of interest, for example, an oil (e.g., lemon essential oil), a protein (e.g., bovine seroalbumina), or a drug (e.g., Ketoconazole, Minoxidil or Triclosan). Said examples show that said nanoparticles have high mucosal bioadhesion, high long-term stability in an aqueous medium, high encapsulation efficiency of products of interest, such as small or large, hydrophilic, hydrophobic or amphiphilic, compounds, high encapsulation efficiency of oils, and that the nanoparticles enhance the solubility in water of hydrophobic compounds.

The materials used for the production of said nanoparticles are described below.

Materials

As half ($C_1$-$C_4$) alkyl esters of PVM/MA copolymers, commercial GANTREZ® ES ethanolic solutions were used; namely, GANTREZ® ES ethanolic solutions (50% w/v) of monoethyl ester (GANTREZ® ES 225) and monobutyl ester (GANTREZ ES® 425) of poly methyl ether-co-maleic anhydride copolymer (PVM/MA) and GANTREZ® AN 119 [Molecular Weight (Mw): 200,000 (g/mol)] were supplied from International Specialty Products (ISP, Spain).

Ultra pure water soluble chitosan (PROTASAN UP CL 113, Mw: 50,000-150,000 g/mol) was supplied by Novamatrix (Norway).

Fluorescein isothiocyanate labelled bovine serum albumin (FITC-BSA), lipophilic fluorescent probe 1,1'-dioctadecyl-3,3,3',3'-tetramethylindocarbocyanine perchlorate and TPGS (alpha-tocopheryl succinate esterified to polyethylene glycol 1000 [PEG 1000]) were supplied by Sigma (Spain).

European Pharmacopeia grade Triclosan, Minoxidil, Ketoconazol and Lemon essential oil were supplied by Fagron (Spain).

Sodium hyaluronate and medium chain triglycerides (Miglyol® 812) was supplied by Fagron (Spain).

All the other chemical reagents including excipients were of analytical grade and supplied by Sigma (Spain).

Example 1

Preparation and Characterization of GANTREZ® ES Nanoparticles

1.1 Preparation of GANTREZ® ES Nanoparticles by Nanoprecipitation-Solvent Displacement Method To obtain GANTREZ® ES nanoparticles, the polymer ethanolic solution (50% w/v) of monoethyl ester (GANTREZ® ES 225) and monobutyl ester (GANTREZ® ES 425) of poly methyl ether-co-maleic anhydride copolymer (PVM/MA) was diluted with absolute ethanol to a concentration of 5% (w/v). Then, the nanoparticles were formed by mixing 5 mL of the polymer solution with 10 mL of bidistilled water as polymer miscible non-solvent. The resulting nanoparticles suspension was evaporated under reduced pressure using a rotavapor (Büchi R-144, Switzerland) to eliminate ethanol.

On the other hand, in situ self-assembled GANTREZ® ES nanoparticles (SANP) with low final content of ethanol without the need of evaporation were obtained. For this purpose, a non-volatile polyol (propylene glycol) polymer solution containing GANTREZ® ES 425 5% (w/v) was prepared by dissolving 10 g of GANTREZ® ES 425 alcoholic solution (50% w/v ethanol solution) in 100 mL propylene glycol, and then 1 mL of propylene glycol-GANTREZ® ES 425 (5% w/v) solution was mixed with 10 mL of bidistilled water. to obtain the nanoparticles. Finally, The aqueous suspension of empty anionic GANTREZ® ES nanoparticles was collected for further characterization.

In order to obtain cationic GANTREZ® ES nanoparticles, 15 mL of the hydroalcoholic suspension of GANTREZ® ES nanoparticles (mixture of 5 mL of GANTREZ® ES 225 (or GANTREZ® ES 425) alcoholic solution (5% w/v) and 10 mL of bidistilled water) or 10 mL of GANTREZ® ES 425 nanoparticles obtained by the in situ technique were incubated with 15 mL of aqueous solution containing ultra pure water soluble chitosan (PROTASAN UP CL 113) at different chitosan concentrations (1.25, 2.5 and 5 mg/mL). Then, the mixture was left under magnetic agitation for 5 min at room temperature. The resulting nanoparticles suspension was evaporated under reduced pressure and chitosan-coated GANTREZ® ES nanoparticles were collected for further characterization.

1.2 Characterization of Empty GANTREZ® ES Nanoparticles

1.2.1 Size, Zeta Potential, Yield and Morphology of the Nanoparticles

The size and zeta potential of the nanoparticles were determined by photon correlation spectroscopy and electrophoretic laser Doppler anemometry, respectively, using a Zetamaster analyser system (Malvern Instruments, UK). Samples were diluted with bidistilled water and measured at 25° C. with a scattering angle of 90°.

The yield of the nanoparticles preparation process, which is the percent of polymer transformed into nanoparticles, was determined by gravimetry from freeze-dried samples as described previously [12]. For this purpose, the nanoparticles aqueous suspensions were centrifuged twice at 27,000×g for 20 min (Sigma lab centrifuge, Rotor 3336, Biofuge Heraeus, Germany), recollected and lyophilized in a Genesis 12EL apparatus (Virtis, USA). The percentage yield of the nanoparticles (the amount of polymer transformed into nanoparticles) was calculated as the ratio between the dry lyophilized nanoparticles samples and the initial amount of the polymer used to prepare the formulations.

The morphological characteristics of the nanoparticles were visualized by scanning electron microscopy (SEM) in a Zeiss DSM 940 digital scanning electron microscope (Oberkochen, Germany) and transmission electron microscopy (TEM) in an electron microscope Zeiss Libra® 120 (Oberkochen, Germany).

1.2.2 Results

Table 1 shows the main physico-chemical characteristics of GANTREZ® ES nanoparticles. Generally, empty anionic GANTREZ® ES nanoparticles prepared from GANTREZ® ES 225 (GES-NP1) and GANTREZ® ES 425 (GES-NP2) displayed a homogenous size which was about 140 nm (GES-NP1, GES-NP2 and self-assembled GES-NP) and negative surface charge of approximately −60 mV. The percentage yield of the nanoparticles was very high for all formulations (about 98%). On the other hand, coating of GANTREZ® ES nanoparticles with chitosan significantly increased the particles size to be around 200 nm compared to non coated ones ($P<0.05$). Chitosan coated nanoparticles (GES-NP-Q 1.25, GES-NP-Q 2.5 and GES-NP-Q 5) have homogenous sizes with a positive surface charge. It has been noted that by increasing the amount of chitosan attached to the surface of the nanoparticles, both particles size and positive surface charge were significantly increased ($P<0.05$).

TABLE 1

Physico-chemical characteristics of Gantrez ® ES nanoparticles. Data expressed as mean ± SD (n = 6)

| | [a] Size (nm), (±SD) | [b] PDI | [c] Zeta potential (mV), (±SD) | [d] % yield, (±SD) |
|---|---|---|---|---|
| GES-NP1 | 137.08 (1.37) | 0.115 | −62.6 (0.92) | 98.32 (1.21) |
| GES-NP2 | 145.03 (1.88) | 0.213 | −66.21 (1.03) | 97.11 (3.3) |
| Self-assembled GES-NP | 131.91 (2.54) | 0.100 | −55.11 (2.11) | 97.13 (1.27) |
| GES-NP-Q 1.25 | 187.43 (4.22)* | 0.118 | +20.48 (1.81)* | 97.11 (1.98) |
| GES-NP-Q 2.5 | 198.97 (5.32)* | 0.121 | +24.08 (1.81)* | 99.80 (3.30) |
| GES-NP-Q 5 | 220.30 (8.15)* | 0.143 | +42.82 (0.62)* | 97.99 (2.02) |

GES-NP1: Gantrez ® ES nanoparticles obtained from the polymer Gantrez ® ES 225
GES-NP2: Gantrez ® ES nanoparticles obtained from the polymer Gantrez ® ES 425
GES-NP-Q: Gantrez ® ES 225 nanoparticles coated with different amounts of chitosan
[a] Determination of the nanoparticles size (nm) by photon correlation spectroscopy.
[b] Polydispersity Index.
[c] Determination of the zeta potential by electrophoretic laser Doppler anemometry.
[d] Percentage of the nanoparticles formed from the initial amount of the polymer used.
*$P < 0.05$; Chitosan-coated nanoparticles vs. control nanoparticles (GES-NP) (Student t-Test).

GANTREZ® ES nanoparticles were found to be spherical and homogeneous when examined by SEM and TEM [FIGS. 1A and 1B (GES-NP1)].

1.3 Nanoparticles Stability Study

1.3.1 Short and Long Period Stability Studies

In order to study the degradation rate of GANTREZ® ES nanoparticles at different conditions, the stability was monitored by turbidmetric assay at 405 nm according to previously published study [13]. For this purpose, a comparative short period stability study was performed between different concentrations of GANTREZ® ES 225 nanoparticles aqueous suspensions (10 and 20 mg nanoparticles/mL) and GANTREZ® AN 119 ones at room temperature. Non cross-linked GANTREZ® AN 119 nanoparticles [8] were used as reference in this study because GANTREZ® AN 119 (ISP, Spain) has been considered as a water insoluble polymer.

On the other hand, long period stability study (approximately for 3 months) of aqueous suspension of GANTREZ® ES 225 and GANTREZ® AN nanoparticles (10 mg/mL) was performed at different temperatures (4° C., room temperature (18-22° C.) and 37° C.)

All samples were assayed by triplicate and data were represented by mean and SD. The size of the nanoparticles was monitored during the study, and, finally, scanning electron microscopy (SEM) was performed to investigate the morphology changes in nanoparticles formulation in the short period stability study.

1.3.2 Results

Figure 2:
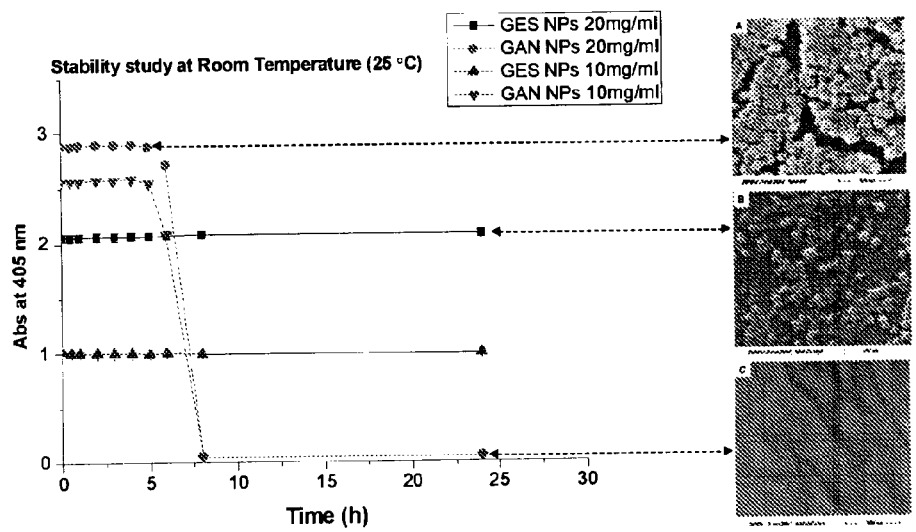
FIG. 2. Stability study in correlation with nanoparticles concentration at room temperature (25° C.) and the corresponding Scanning Electron Microscopy (SEM). (A) and (C) show the photographies for GANTREZ® AN nanoparticles by SEM obtained before hydrolysis and after hydrolysis, respectively; (B) photography for GANTREZ® ES 225 nanoparticles by SEM at 24 h.
Figure 3:
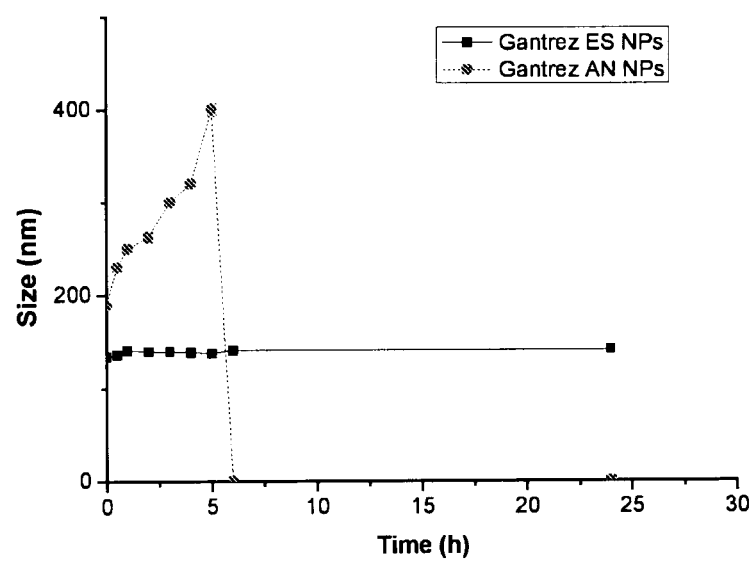
FIG. 3. Monitoring of the size for both GANTREZ® ES 225 and GANTREZ® AN nanoparticles during the stability study at room temperature (25° C.).

FIG. 2 shows the degradation rate of GANTREZ® ES 225 and GANTREZ® AN nanoparticles within 24 hours at room temperature (25° C.) at two different concentrations (10 and 20 mg/mL) and the corresponding scanning electron microscopy (SEM) to investigate the morphology changes in nanoparticles. Generally, GANTREZ® ES 225 nanoparticles demonstrated a higher stability and a lower degradation rate in aqueous medium in comparison to GANTREZ® AN nanoparticles independent on the polymer concentration. Within the first 5 hours, both type of nanoparticles demonstrated a similar stability. However, GANTREZ® AN nanoparticles started to show dramatic degradation rate profile after 5 h and they were totally degraded within 6 to 8 h post incubation. The lag time (i.e., the time at which the turbidity starts to decrease) of GANTREZ® AN nanoparticles was calculated to be about 5 hours. SEM image in FIG. 2 indicated that GANTREZ® AN nanoparticles were totally degraded and only a polymeric film was observed in image C. On the other hand, the size of GANTREZ® AN nanoparticles was significantly increased from 200 to 400 nm within the first 5 hours of incubation (FIG. 3). After that, the size of the nanoparticles was not detected due to the hydrolysis of GANTREZ® AN nanoparticles to form a free polymeric solution of GANTREZ® S (water soluble from of GANTREZ® AN).

Figure 4:
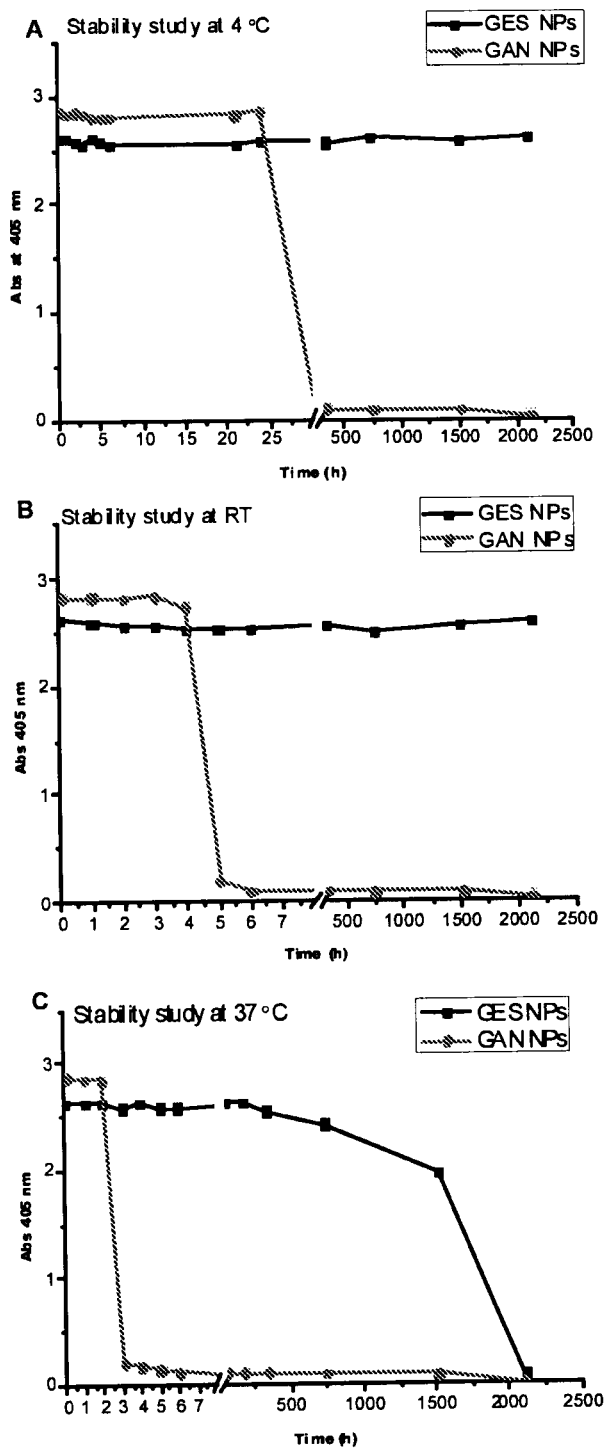
FIG. 4. Comparative stability study between GANTREZ® ES 225 (GES NPs) and GANTREZ® AN (GAN NPs) nanoparticles at different temperatures, namely, at (A) 4° C., (B) room temperature (25° C.), and (C) 37° C., using bidistilled water as dispersing medium. The concentration of the nanoparticles used in this test was 10 mg/mL.

In case of the long period stability study (FIG. 4), it has been observed that GANTREZ® ES nanoparticles displayed a higher stability at different temperatures when compared to GANTREZ® AN nanoparticles. The degradation rate of GANTREZ® AN nanoparticles increases by increasing the temperature and the degradation lag time was ranged from 2 to 24 hours post incubation. In case of GANTREZ® ES nanoparticles, no degradation was observed at 4° C. or room temperature. However, at 37° C. the stability represented by degradation lag time for GANTREZ® ES nanoparticles was approximately 350-400 folds longer than for GANTREZ® AN nanoparticles.

Example 2

Preparation and Characterization of GANTREZ® ES Nanocapsules Containing Oils

2.1 Preparation of GANTREZ® ES Nanocapsules Containing Oils

In order to prepare GANTREZ® ES nanocapsules loaded with a liquid oil, lemon essential oil was incorporated into GANTREZ® ES polymeric shell by the solvent displacement method. For this purpose, 0.5 mL of lemon essential oil (fluorescently labelled with lipophilic fluorescent probe 1,1'-dioctadecyl-3,3,3',3'-tetramethylindocarbocyanine perchlorate), and 0.5 mL of propylene glycol were mixed with 10 mL of a GANTREZ® ES 425 ethanolic solution having a polymer concentration of 25 mg/mL. After that, the oily polymer solution was poured into 30 mL of an aqueous phase (medium) containing a surfactant, namely TPGS (d-alpha tocopheryl polyethylene glycol 1000 succinate) at 1% (w/v). Control formulations were prepared by the addition of an lemon essential oil ethanolic solution without GANTREZ® ES 425 polymer. Then, the resulting nanocapsules suspension was evaporated under reduced pressure using a rotavapor (Büchi R-144, Switzerland) to eliminate ethanol. The final aqueous suspension of lemon essential oil-loaded GANTREZ® ES 425 nanocapsules was collected for further characterization.

2.2 Characterization of GANTREZ® ES Nanocapsules

The size, zeta potential and yield of the nanocapsules preparation process were determined as described in Example 1. In order to calculate the encapsulation efficiency of fluorescently labelled lemon essential oil, 2 mL of water immiscible oil (Mygliol® 812) were added to 0.5 mL of GANTREZ® ES 425 nanocapsules to extract the free oil by shaking at room temperature for 10 min. The amount of free oil was assayed by spectrofluorimetry at an excitation wavelength of 540 nm and an emission wavelength of 580 nm (GENios, TECAN, Groedig, Austria). For that purpose, calibration curves were done with lemon essential oil loaded with lipophilic fluorescent probe 1,1'-dioctadecyl-3,3,3',3'-tetramethylindocarbocyanine perchlorate standard solutions at a concentration range from 0.05 to 2.5 µg/mL (r=0.996). Finally, formulations were visualized by fluorescence microscopy (Olympus CH40 Model, Olympus, Spain).

2.3 Results

Figure 5:
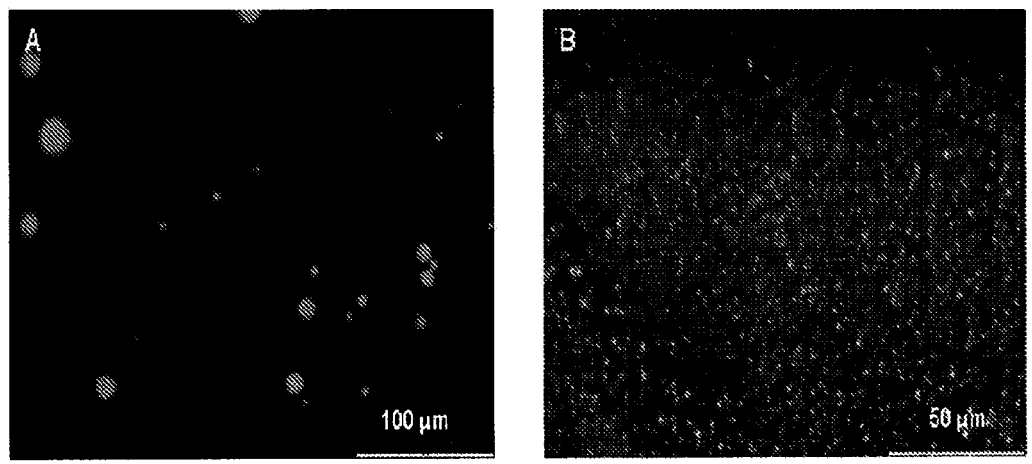
FIG. 5. Fluorescence microscopy for (A) a lemon essential oil control formulation, and (B) a lemon essential oil-loaded GANTREZ® ES 425 nanocapsules.

Table 2 describes the main physico-chemical characteristics of GANTREZ® ES 425 nanocapsules loaded with a liquid oil (lemon oil). It was observed that volatile lemon essential oil was efficiently encapsulated in GANTREZ® ES 425 nanocapsules and the percentage of encapsulated oil was approximately 82%. The size of GANTREZ® ES nanocapsules was homogenous (about 212 nm) with negatively charge zeta potential. On the other hand, control formulations prepared without GANTREZ® ES polymer shown low stability and thus oil phase separation, and the size of oil droplets in this control formulation was heterogonous ranging from 5 to 15 µm. This feature was observed by fluorescence microscopy of both formulations (FIG. 5).

TABLE 2

Physico-chemical characteristics of lemon essential oil loaded Gantrez ® ES 425 nanocapsules and control formulation. Data expressed as mean ± SD (n = 6)

|  | [a] Size (nm), (±SD) | [b] PDI | [c] Zeta potential (mV), (±SD) | [d] % yield, (±SD) | [e] % Encapsulation efficiency of lemon oil |
|---|---|---|---|---|---|
| GES-NC | 212.31 (3.11) | 0.206 | −65.11 (1.05) | 93.12 (1.45) | 82.7 (3.77) |
| Oil emulsion | 1352.30 (100.47)* | 0.667 | −23.61 (1.72) | — | 1.11 (0.19) |

GES-NC: Fluorescently labelled Gantrez ® ES 425 nanocapsules loaded with lemon essential oil.
Oil emulsion: Formulation without the use of Gantrez ® ES 425 polymer (negative control).
[a] Determination of the nanoparticles size (nm) by photon correlation spectroscopy.
[b] Polydispersity Index.
[c] Determination of the zeta potential by electrophoretic laser Doppler anemometry.
[d] The percentage of the nanoparticles formed from the initial amount of the polymer used.
[e] % Encapsulation efficiency: Percentage of the amount of encapsulated lemon oil in Gantrez ® ES 425 nanoparticles in relation with the initial amount of lemon oil used.
*P < 0.05; Gantrez ® ES loaded nanoparticles versus control formulation (oil emulsion) (Student t-Test).

Example 3

Preparation and Characterization of GANTREZ® ES Nanoparticles by Spray Drying For this purpose, 50 mL of GANTREZ® ES 425 ethanolic solution (50 mg/mL) were mixed with 100 mL of distilled water to form GANTREZ® ES nanoparticles. Different surfactants were added to the nanoparticles hydroalcoholic suspension such as sodium dodecyl sulfate (SDS) (100 mg), PLURONIC® F68 [ethylene oxide/propylene oxide block copolymer] (100 mg) or TWEEN® 80 [polyoxyethylene (20) sorbitan monooleate] (7.5 mg). Finally, 7.5 g of mannitol were added as excipient. To obtain a dry powder of the GANTREZ® ES nanoparticles, the suspension was dried in a Mini Spray-dryer Büchi B191 (Büchi Labortechnik AG, Switzerland) under the following conditions:
  inlet temperature: 90° C.,
  outlet temperature: 60° C.,
  spray-flow: 600 L/h, and
  aspirator at 90% of the maximum capacity.

During the process the nanoparticles suspension was maintained under moderate agitation. The recovered powder was stored in closed glass vials at room temperature for further characterization as in Example 1.

Table 3 describes the main physico-chemical properties of GANTREZ® ES 425 nanoparticles obtained after spray drying of the GANTREZ® ES 425 nanoparticles suspension with different excipients. The yield of the spray drying process was calculated as the difference between the weight of dry powder obtained from the spray dryer and the initial theoretical weight of the components added. The dry powder of the nanoparticles obtained from the spray dryer was easily dispersed in water and the sizes obtained were homogenous with acceptable polydispersity indexes (0.2-0.3). The size of the nanoparticles obtained after the suspension of the sample in bidistilled water was around 230 nm with surface negative charge. The yield of the spray drying process was about 80% of the initial theoretical dry solid used.

TABLE 3

Physicochemical characteristics of Gantrez ® ES 425 nanoparticles obtained by spray drying. Data expressed as mean ± SD (n = 6)

|  | [a] Size (nm), (±SD) | [b] PDI | [c] Zeta potential (mV), (±SD) | [d] % Process yield, (±SD) |
|---|---|---|---|---|
| GES-NP | 231.27 (3.11) | 0.263 | −62.71 (0.64) | 76.36 (3.45) |
| GES-NP-SDS | 216.03 (1.56) | 0.213 | −74.01 (0.60) | 77.93 (5.55) |
| GES-NP-T | 235.23 (2.20)* | 0.311 | −78.02 (0.72)* | 81.05 (2.89) |
| GES-NP-P | 230.06 (4.82)* | 0.338 | −64.31 (0.59) | 88.12 (4.11) |

GES-NP: Gantrez ® ES nanoparticles obtained from Gantrez ® ES 425.
GES-NP-SDS: Gantrez ® ES 425 nanoparticles containing SDS.
GES-NP-T: Gantrez ® ES 425 nanoparticles containing Tween ® 80.
GES-NP-P: Gantrez ® ES 425 nanoparticles containing Pluronic ® F68.
[a] Determination of the nanoparticles size (nm) by photon correlation spectroscopy.
[b] Polydispersity Index.
[c] Determination of the zeta potential by electrophoretic laser Doppler anemometry.
[d] The percentage of the nanoparticles formed from the initial amount of the polymer used.
*P < 0.05; spray dried nanoparticles with excipients (GES-NP-SDS, GES-NP-T and GES-NP-P) versus control nanoparticles (GES-NP) (Student t-Test).

Example 4

Encapsulation of Bovine Serum Albumin as Large Molecule Model in GANTREZ® ES Nanoparticles

4.1 Encapsulation of BSA in GANTREZ® ES Nanoparticles

A fluorescently labelled protein was used as a large molecules drug model to be incorporated into GANTREZ® ES nanoparticles. For that purpose, different amounts of fluorescein isothiocyanate labelled bovine serum albumin (FITC-BSA) were used (0.5, 1 and 2.5 mg/250 mg of GANTREZ® ES 425). The protein was dissolved in 1 mL of distilled water and then added to 5 mL of a GANTREZ® ES 425 ethanolic solution (50 mg/mL). The solution was left under magnetic stirring for 5 min at room temperature, and then 9 mL of distilled water were added to form the nanoparticles. The resulting nanoparticles suspension was evaporated under reduced pressure using a rotavapor (Büchi R-144, Switzerland) to eliminate ethanol. The final aqueous suspension of FITC-BSA loaded GANTREZ® ES nanoparticles was collected for further characterization.

4.2 Characterization of FITC-BSA Loaded GANTREZ® ES Nanoparticles

The size, zeta potential and yield of the nanoparticles preparation process were determined as described in Example 1. In order to calculate the encapsulation efficiency of FITC-BSA in GANTREZ® ES nanoparticles, the nanoparticles suspensions were centrifuged at 27,000×g for 20 min. Then, the amount of free FITC-BSA was assayed in the supernatants and the amount of encapsulated protein was estimated from the initial amount of protein used. For that purpose, calibration curves were prepared with FITC-BSA standard solutions at a concentration range from 1 to 50 µg/mL (r=0.996). The assay was performed by spectrofluorimetry at 485 nm (excitation wavelength) and 535 nm (emission wavelength) (GENios, TECAN, Austria). The freshly prepared nanoparticles containing FITC-BSA were deposited on poly-L-lysine precoated slides (Sigma, Spain) and visualized by fluorescence microscopy (Olympus CH40 Model, Olympus, Spain).

4.3 Results

Figure 6:
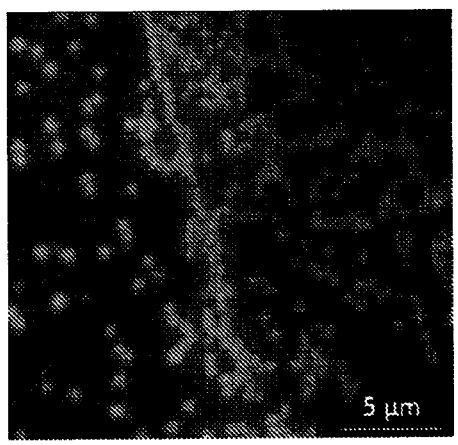
FIG. 6. Fluorescence microscopy for FITC-BSA loaded GANTREZ® ES 425 nanoparticles.

Table 4 describes the main physico-chemical characteristics of FITC-BSA-loaded GANTREZ® ES nanoparticles. It was observed that the encapsulation of FITC-BSA in GANTREZ® ES nanoparticles caused a significant increase in the nanoparticles size but did not affect the surface charge of the nanoparticles. The encapsulation efficiency was approximately 96%, which indicated the high capacity of GANTREZ® ES nanoparticles to incorporate large molecules such as proteins. Fluorescence microscopy of FITC-BSA GANTREZ® ES nanoparticles corroborated the high incorporation of FITC-BSA inside the nanoparticles polymer matrix (FIG. 6).

This example shows that a high encapsulation efficiency of a large hydrophilic compound (BSA) was achieved (about 97%).

Example 5

Encapsulation of Rhodamine B as Small Hydrophilic Drug Model in GANTREZ® ES Nanoparticles Rhodamine B-loaded GANTREZ® ES nanoparticles were prepared by the addition of the fluorescent hydrophilic molecule (1 mg) pre-dissolved in 1 mL of bidistilled water to 5 mL of a GANTREZ® ES 425 ethanolic solution (50 mg/mL). The solution was left under magnetic stirring for 5 min at room temperature, and then 9 mL of distilled water were added to form the nanoparticles. The resulting nanoparticles suspension was evaporated under reduced pressure using a rotavapor (Büchi R-144, Switzerland) to eliminate ethanol. The amount of the RBITC [Rhodamine B isothiocyanate] loaded into the nanoparticles was determined by colorimetry at 540 nm (Labsystems iEMS Reader MF, Finland). The quantity of loaded RBITC was estimated as the difference between its initial concentration added and the concentration measured in the supernatants after the centrifugation step. In vitro release of RBITC from the nanoparticles was studied according to a modified protocol described elsewhere [18]. For that purpose, 1 mL of the nanoparticles suspension was mixed with 3 mL of phosphate buffered saline (PBS) pH 7.4 and left under agitation at 37±1° C. At different time intervals, the nanoparticles were collected by using dialysis tubes Vivaspin® 100,000 MWCO (VIVASPIN, Germany). The dialysates were assayed to quantify the amount of Rhodamine B released by colorimetry at 540 nm.

GANTREZ® ES nanoparticles shown a high capacity to associate small hydrophilic molecules such as Rhodamine B (Table 5). The encapsulation efficiency was 99% of the initial amount of Rhodamine B added. On the other hand, the encapsulation of Rhodamine B significantly increased the nanoparticles size (Table 5) without any influence on the surface charge of the nanoparticles.

TABLE 4

Physico-chemical characteristics of FITC-BSA-loaded Gantrez ® ES 425 nanoparticles. Data expressed as mean ± SD (n = 6)

|  | [a] Size (nm), (±SD) | [b] PDI | [c] Zeta potential (mV), (±SD) | [d] % yield, (±SD) | [e] % Encapsulation efficiency of FITC-BSA, (±SD) |
|---|---|---|---|---|---|
| GES-NP | 122.31 (3.73) | 0.109 | −59.93 (3.45) | 97.61 (1.21) | — |
| NP-BSA-0.5 | 133.30 (1.47)* | 0.130 | −60.51 (1.43) | 98.52 (1.71) | 96.11 (3.12) |
| NP-BSA-1 | 143.47 (1.59)* | 0.132 | −61.10 (0.86) | 96.31 (2.13) | 97.34 (1.69) |
| NP-BSA-2.5 | 176.67 (0.74)* | 0.109 | −62.21 (0.02) | 97.79 (2.82) | 95.88 (3.45) |

GES-NP: Gantrez ® ES nanoparticles obtained from Gantrez ® ES 425.

NP-BSA-0.5, NP-BSA-1 and NP-BSA-2.5: FITC-BSA loaded Gantrez ® ES 425 nanoparticles with different amounts of FITC-BSA

[a] Determination of the nanoparticles size (nm) by photon correlation spectroscopy.

[b] Polydispersity Index.

[c] Determination of the zeta potential by electrophoretic laser Doppler anemometry.

[d] The percentage of the nanoparticles formed from the initial amount of the polymer used.

[e] % Encapsulation efficiency: Percentage of the amount of encapsulated protein in Gantrez ® ES 425 nanoparticles in relation with the initial amount used.

*$P < 0.05$

FITC-BSA loaded nanoparticles versus control nanoparticles (GES-NP) (Student t-Test).

TABLE 5

Physico-chemical characteristics of Rhodamine B-loaded Gantrez ® ES 425 nanoparticles.
Data expressed as mean ± SD (n = 6).

| | [a] Size (nm), (±SD) | [b] PDI | [c] Zeta potential (mV), (±SD) | [d] % yield, (±SD) | [e] % Encapsulation efficiency of Rhodamine B (±SD) |
|---|---|---|---|---|---|
| GES-NP | 129.11 (5.03) | 0.119 | −60.03 (1.33) | 96.69 (2.91) | — |
| GESNP-RB | 143.50 (1.81)* | 0.145 | −60.51 (3.43) | 98.52 (1.71) | 99.11 (1.18) |

GES-NP: Gantrez ® ES 425 nanoparticles obtained from Gantrez ® ES 425.
GESNP-RB: Rhodamine B-loaded Gantrez ® ES 425 nanoparticles.
[a] Determination of the nanoparticles size (nm) by photon correlation spectroscopy.
[b] Polydispersity Index.
[c] Determination of the zeta potential by electrophoretic laser Doppler anemometry.
[d] The percentage of the nanoparticles formed from the initial amount of the polymer used.
[e] % Encapsulation efficiency: Percentage of the amount of encapsulated Rhodamine B in Gantrez ® ES 425 nanoparticles in relation with the initial amount used.
*P < 0.05; Rhodamine B-loaded nanoparticles versus control nanoparticles (GES-NP) (Student t-Test).

Example 6

Encapsulation of Ketoconazole as Hydrophobic Antifungal Drug Model in GANTREZ® ES Nanoparticles for Mucosal and Topical Delivery Applications 6.1 Production of Ketoconazole (KTZ) Loaded GANTREZ® ES Nanoparticles In order to investigate the capacity of GANTREZ® ES nanoparticles to entrap hydrophobic molecules, Ketoconazole was selected as water insoluble hydrophobic molecule. Ketoconazole is an imidazole antifungal agent, with very poor solubility characteristics in common solvents such as water and alcohols. The selection of the appropriate Ketoconazole:polymer ratio (w/w) which is needed to dissolve drug crystals and to obtain homogeneous nanoparticles free from drug crystals was firstly optimized. For that purpose, 200 mg of KTZ were resuspended in different volumes of both absolute ethanol (10, 15 and 20 mL) as control solution or in the same volumes of GANTREZ® ES 425 ethanolic solution (50 mg/mL). GANTREZ® ES nanoparticles were produced by the addition of the corresponding volume of bidistilled water (2:1 (v/v) water/polymer solution) to GANTREZ® ES alcoholic solutions containing KTZ. In parallel, similar volumes of bidistilled water were added to KTZ ethanolic solution (negative control without the polymer to investigate the solubilizing effect of GANTREZ® ES). The resulting nanoparticles suspension or hydroalcoholic solutions containing KTZ were evaporated under reduced pressure using a rotavapor (Büchi R-144, Switzerland) to eliminate ethanol. Finally, the aqueous suspensions of KTZ-loaded GANTREZ® ES nanoparticles and KTZ aqueous suspension without the polymer were collected for further characterization and drug content quantification.

6.2 Characterization of KTZ Nanoparticles

The size, zeta potential and yield of the nanoparticles preparation process were determined as described in Example 1. Fluorescence and optical microscopy was used to investigate the presence of crystals in the resulting KTZ-loaded GANTREZ® ES nanoparticles suspension. For this purpose, the KTZ-loaded nanoparticles and free drug treated by the same way were visualized by scanning electron microscopy (SEM). In addition, KTZ-loaded GANTREZ® ES nanoparticles were left at room temperature for 2 months, and, then, the nanoparticles morphology was investigated by SEM. The amount of encapsulated drug in the nanoparticles was assayed by UV spectrophotometry at 257 nm (Shimadzu 1203 UV-VIS). In order to quantify the amount of KTZ in the nanoparticles suspension or free KTZ suspension without the polymer GANTREZ® ES), all samples of fleshly prepared formulations were evaporated under reduced pressure to eliminate ethanol, and then 1 mL of triplicate samples were centrifuged at 20,000 rpm for 25 min. After that, 0.5 mL of the supernatants were diluted with methanol and assayed by spectrophotometry at 257 nm [14]. In parallel, the nanoparticles precipitates were left at 37 C.° for 2 days to evaporate the residual water and then the formulations containing KTZ was dissolved in 1 mL methanol assayed at 257 nm. The calibration curves were done by dissolving 25 mg of KTZ in 100 mL of methanol. The calibration curve points (5-30 µg/mL) were prepared from this standard solution.

6.3 Results

From the results shown in Table 6, it can be concluded that GANTREZ® ES nanoparticles show a high capacity to encapsulate water insoluble drug molecules such as Ketoconazole. The encapsulation efficiency was approximately 97% of the initial amount of KTZ added. The quantification results obtained for the aqueous suspension containing the crystalline precipitate obtained after the precipitation of KTZ from the alcoholic solution indicated that the water solubility of KTZ was around 11 µg/mL which was similar to previously published data [15]. The aspect of the precipitate in this negative control sample was totally crystalline.

Figure 7:
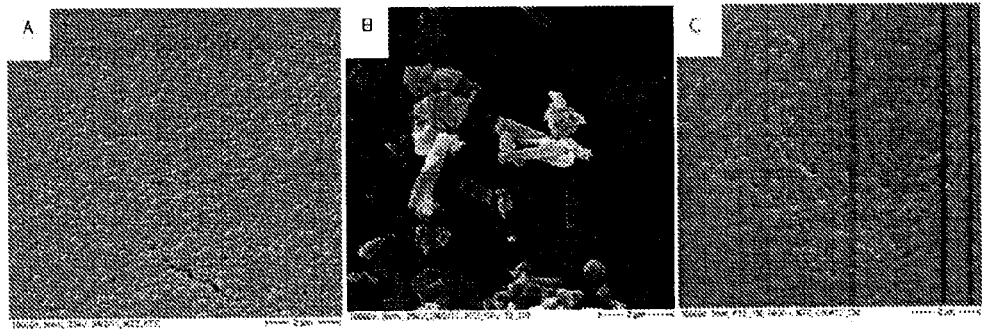
FIG. 7A. Scanning electron microscopy (SEM) for Ketoconazole-loaded GANTREZ® ES 425 nanoparticles (KTZ-GANTREZ® ES 425 nanoparticles).
FIG. 7B. Scanning electron microscopy (SEM) for KTZ crystals treated by the same method applied for nanoparticles formation.
FIG. 7C. Scanning electron microscopy (SEM) for nanoparticles left at room temperature for at least 2 months where no crystal growth or formation was observed.

On the other hand, the association of KTZ to GANTREZ® ES nanoparticles (NPGES-KTZ1, NPGES-KTZ2 and NPGES-KTZ3) decreased the surface negative charge compared to control ones (GES-NP). The sizes of the nanoparticles containing KTZ at different polymer concentrations were homogeneous (about 200 nm) which indicated the absence of dug crystals which were of around 2-10 µm. These drug crystals were observed only after the treatment of KTZ alcoholic solutions by the same way as GANTREZ® ES alcoholic solutions containing KTZ used to form the nanoparticles. This fact was observed after the visualization of both KTZ crystals and KTZ-loaded GANTREZ® ES nanoparticles by SEM) (FIGS. 7B and 7A, respectively). Similar results from SEM were obtained for nanoparticles left at room temperature for at least 2 months where no crystal growth or formation was observed (FIG. 7C). These results indicate that GANTREZ® ES nanoparticles enhance the aqueous solubility of hydrophobic drugs such as KTZ.

TABLE 6

Physico-chemical characteristics of Ketoconazole-loaded Gantrez ® ES 425 nanoparticles.
Data expressed as mean ± SD (n = 6)

|  | $^a$ Size (nm), (±SD) | $^b$ PDI | $^c$ Zeta potential (mV), (±SD) | $^d$ % yield, (±SD) | $^e$ % Encapsulation efficiency KTZ (±SD) |
|---|---|---|---|---|---|
| GES-NP | 142.13 (2.07) | 0.109 | −58.43 (3.63) | 98.19 (1.81) | — |
| NPGES-KTZ1 | 217.98 (4.00)* | 0.211 | −51.31 (0.64) | 99.32 (2.13) | 96.13 (1.67) |
| NPGES-KTZ2 | 205.12 (3.11)* | 0.223 | −49.12 (1.85) | 99.32 (2.13) | 97.66 (2.03) |
| NPGES-KTZ3 | 234.03 (2.50)* | 0.190 | −50.99 (2.09) | 99.32 (2.13) | 98.29 (1.00) |

GES-NP: Gantrez ® ES 425 nanoparticles obtained from Gantrez ® ES 425.
NPGES-KTZ1: Ketoconazole-loaded Gantrez ® ES 425 nanoparticles (200 mg KTZ and 500 mg Gantrez ® ES 425).
NPGES-KTZ2: Ketoconazole-loaded Gantrez ® ES 425 nanoparticles (200 mg KTZ and 750 mg Gantrez ® ES 425).
NPGES-KTZ3: Ketoconazole-loaded Gantrez ® ES 425 nanoparticles (200 mg KTZ and 1000 mg Gantrez ® ES 425).
$^a$ Determination of the nanoparticles size (nm) by photon correlation spectroscopy.
$^b$ Polydispersity Index.
$^c$ Determination of the zeta potential by electrophoretic laser Doppler anemometry.
$^d$ The percentage of the nanoparticles formed from the initial amount of the polymer used.
$^e$ % Encapsulation efficiency: Percentage of the amount of encapsulated KTZ in Gantrez ® ES 425 nanoparticles in relation with the initial amount used.
*P < 0.05; Ketoconazole-loaded Gantrez ® ES nanoparticles versus control nanoparticles (GES-NP) (Student t-Test).

Example 7

Encapsulation of Triclosan (TRI) as Hydrophobic Antimicrobial Drug Model in GANTREZ® ES Nanoparticles for Mucosal and Topical Delivery 7.1 Production of Triclosan-Loaded GANTREZ® ES Nanoparticles In order to obtain Triclosan (TRI) loaded GANTREZ® ES nanoparticles, different amounts of Triclosan (TRI) were used. For that purpose, 12 and 20 mg of TRI were dissolved in 5 mL of GANTREZ® ES 425 ethanolic solution at 40 mg/mL. GANTREZ® ES 425 nanoparticles were produced by the addition of 10 mL of bidistilled water. After that, the organic solvent (ethanol) was evaporated under reduced pressure using a rotavapor (Büchi R-144, Switzerland), and the final total concentration of TRI in the nanoparticles was 0.12% or 2% (w/v). The aqueous suspensions of the GANTREZ® ES 425 nanoparticles containing TRI were collected for further characterization and drug content quantification.

On the other hand, the technique of in situ self-assembled was applied to obtain GANTREZ® ES 425 nanoparticles loaded with TRI in order to avoid the evaporation step of ethanol and get a final nanoparticles suspension with low ethanol content. For this purpose, a solution of the polymer (GANTREZ® ES 425) was prepared at a concentration of 5% (w/v) in propylene glycol (PG) (GES-PG solution). Then, a TRI solution was prepared by dissolving the corresponding amount of TRI in the propylene glycol polymer solution (TRI-PG solution). The GES-PG solution and the TRI-PG solution were mixed together (GES-TRI-PG solution). After that, the nanoparticles containing TRI were formed by the addition of the GES-TRI-PG solution to water (10 mL).

In parallel, the same concentration of TRI was used in both techniques (solvent displacement and in situ self-assembled technique), but without using GANTREZ® ES 425, for use as a control to check the adjuvant effect on solubility of GANTREZ ES® 425 nanoparticles on TRI.

7.2 Characterization of Triclosan-Loaded GANTREZ® ES Nanoparticles

The size, zeta potential and yield of the nanoparticles preparation process were determined as described in Example 1. Scanning electron microscopy (SEM) and fluorescence microscopy were used to investigate the presence of crystals in the resulting suspension of TRI-loaded GANTREZ® ES 425 nanoparticles and in the negative control formulations (i.e., without GANTREZ® ES 425). The amount of encapsulated drug in the nanoparticles was assayed UV spectrophotometry at 280 nm [9] (Shimadzu 1203 UV-VIS). In order to quantify the amount of TRI in the nanoparticles suspension, all samples of GANTREZ® ES 425 nanoparticles were evaporated under reduced pressure to eliminate ethanol or directly assayed in case of TRI-PG formulations. For that purpose, 1 mL of the samples (in triplicate) were centrifuged at 20000 rpm for 20 min. After that, 0.5 mL of the supernatants were diluted with methanol and assayed by UV spectrophotometry at 280 nm. The calibration curve points (10-40 μg/mL) were prepared from this standard solution.

7.3 Results

Figure 8:
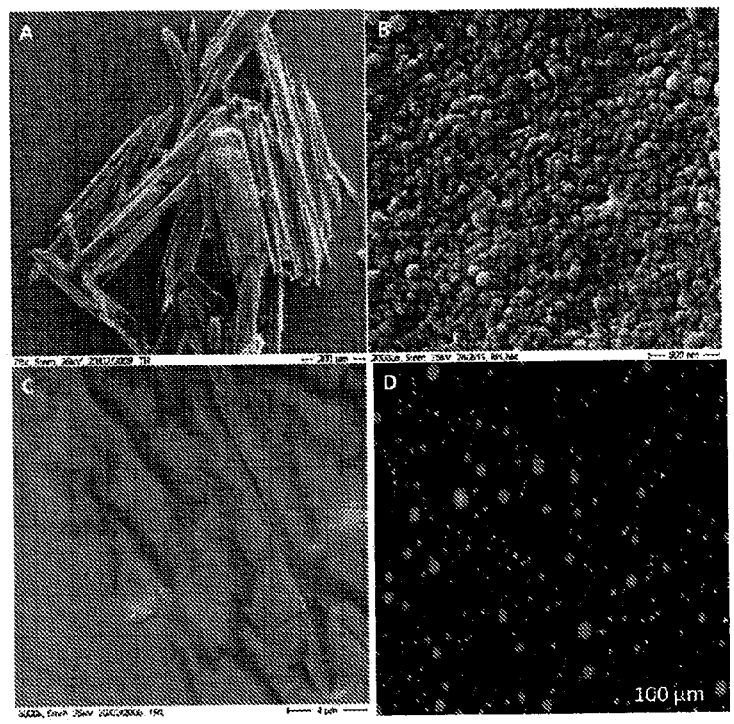
FIG. 8. Scanning electron microscopy (SEM) for (A) Triclosan (TRI) crystals, (B) Triclosan-loaded GANTREZ® ES 425 nanoparticles (TRI-GANTREZ® ES 425 nanoparticles), (C) TRI oil, and (D) fluorescence microscopy for the TRI emulsion stained with the lipophilic fluorescent probe 1,1'-dioctadecyl-3,3,3',3'-tetramethylindocarbocyanine perchlorate.

The results are shown in Table 7. In view of said results, it can be concluded that GANTREZ® ES 425 nanoparticles shown a high capacity to encapsulate a water insoluble drug molecule such as Triclosan (TRI). The encapsulation efficiency was approximately 97% of the initial amount of TRI added in the case of the nanoparticles obtained according to the solvent displacement method. However, the encapsulation efficiency was significantly decreased (82%) in the case of nanoparticles obtained by self-assembled technique. The sizes of the nanoparticles containing TRI at different concentrations were homogeneous (about 140 nm) what indicated the absence of drug crystals which were of around 50-200 μm (FIG. 8A). This feature was observed after the visualization of both TRI crystals (negative control formulations) and TRI-loaded GANTREZ® ES 425 nanoparticles by SEM (FIG. 8B). These results indicate that GANTREZ® ES 425 nanoparticles enhance the aqueous solubility of a hydrophobic drug such as TRI due to the absence of drug crystals in the nanoparticles formulation. Surprisingly, after the addition of a determined amount of water (which was higher than the amount needed to obtain the nanoparticles) to the alcoholic solution of TRI without GANTREZ® ES 425, TRI precipitated as a non-crystalline oily phase and formed an emulsion having big size oily particles. This oil could be visualized by both SEM (FIG. 8C) and by fluorescence microscopy for the TRI emulsion stained with lipophilic fluorescent probe 1,1'-dioctadecyl-3,3,3',3'-tetramethylindocarbocyanine perchlorate (FIG. 8D). The oily phase of TRI was of high density in water and precipitated as an oily layer after the coalescence of oil droplets.

In order to study the physical stability of the formulations, GANTREZ® ES 425 nanoparticles loaded with MXD were left under aggressive and high temperature conditions (37° C. for 1 month) to monitor crystal growth or precipitation phenomena in both polypropylene or glass containers. The size and the general aspect of the formulations were checked

TABLE 7

Physico-chemical characteristics of TRI-loaded Gantrez ® ES 425 nanoparticles. Data expressed as mean ± SD (n = 6)

|  | [a] Size (nm), (±SD) | [b] PDI | [c] Zeta potential (mV), (±SD) | [d] % yield, (±SD) | [e] % Encapsulation efficiency TRI (±SD) |
|---|---|---|---|---|---|
| GES-NP | 132.11 (1.09) | 0.119 | −57.11 (2.34) | 97.25 (2.71) | — |
| NPGES-TRI 0.12 | 142.21 (1.17)* | 0.211 | −59.21 (1.34) | 99.32 (2.63) | 96.13 (1.67) |
| NPGES-TRI 0.2 | 141.12 (2.50)* | 0.200 | −54.18 (1.23) | 97.12 (2.05) | 97.66 (2.03) |
| NPGES-TRI-PG 0.2 | 112.22 (3.07) | 0.190 | −56.99 (2.09) | 95.32 (3.16) | 82.29 (1.00)+ |

GES-NP: Gantrez ® ES 425 nanoparticles obtained from Gantrez ® ES 425.
NPGES-TRI 0.12: Triclosan-loaded Gantrez ® ES 425 nanoparticles (0.12% final drug concentration w/v in nanoparticles suspension).
NPGES-TRI 0.2: Triclosan-loaded Gantrez ® ES 425 nanoparticles (0.2% final drug concentration w/v in nanoparticles suspension).
NPGES-TRI-PG: Self-assembled Triclosan-loaded Gantrez ® ES 425 nanoparticles.
[a] Determination of the nanoparticles size (nm) by photon correlation spectroscopy.
[b] Polydispersity Index.
[c] Determination of the zeta potential by electrophoretic laser Doppler anemometry.
[d] The percentage of the nanoparticles formed from the initial amount of the polymer used.
[e] % Encapsulation efficiency: Percentage of the amount of TRI encapsulated in Gantrez ® ES 425 nanoparticles in relation with the initial amount used.
*P < 0.05; Triclosan-loaded Gantrez ® ES nanoparticles versus control nanoparticles (GES-NP) (Student t-Test).
+P < 0.05; NPGES-TRI-PG nanoparticles versus NPGES-TRI (Student t-Test).

Example 8

Encapsulation of Minoxidil (MXD) as Hydrophobic Drug Model in GANTREZ® ES Nanoparticles for Hair Loss Applications 8.1 Production of MXD Loaded GANTREZ® ES Nanoparticles GANTREZ ES® nanoparticles loaded with MXD were prepared as previously described for GANTREZ ES® nanoparticles loaded with KTZ (Example 6). For that purpose, 200 mg and 250 mg of MXD were dissolved in 5 mL of an ethanolic solution or in 5 mL of a GANTREZ® ES 425 ethanolic solution (50 mg/mL). Then GANTREZ® ES 425 nanoparticles loaded with MXD were produced by the addition of 10 mL of bidistilled water to 5 mL of the GANTREZ® ES 425 alcoholic solution under magnetic stirring. The resulting suspension of nanoparticles or the resulting hydroalcoholic solution containing MXD were evaporated under reduced pressure using a rotavapor (Büchi R-144, Switzerland) to eliminate ethanol. Finally, the aqueous suspensions of MXD containing GANTREZ® ES 425 nanoparticles were collected for further characterization and drug content quantification. Finally, different excipients used as compatible plasticizers with the polymer (GANTREZ® ES) were added including propylene glycol, PEG400 (polyethylene glycol with molecular weight (Mw) of 400 Da), and glycerol (10% (v/v)).

8.2 Characterization of MXD Nanoparticles

The size, zeta potential and yield of the nanoparticles production process were determined as described in Example 1. daily. In addition, macroscopical and microscopical characterization (optical and scanning electron microscopy) were used to investigate the appearance and physical properties of nanoparticulate polymer dry films containing MXD or commercial formulations. For this purpose, 200 μL of sample [2% (w/v) of MXD] were applied on a plastic surface and then the samples were dried at 37° C. to simulate the phenomena that occur after their application on the scalp. The formulations used were GANTREZ® ES 425 nanoparticles containing MXD with different excipients (propylene glycol, PEG 400 and glycerol), a commercial formulation of MDX containing ethanol, propylene glycol, EDTA (ethylenediaminetetraacetic acid) and water (LACOVIN® 2%), a commercial formulation containing gamma-cyclodextrins, propylene glycol, ethanol and water (ALOPEXY® 2%). These formulations were applied on a dry surface and their aspects were macroscopically and microscopically monitored. Finally, the amount of encapsulated drug in the nanoparticles was assayed by UV spectrophotometry at 286 nm (Shimadzu 1203 UV-VIS). For this purpose, 1 mL of samples (in triplicate) of GANTREZ® ES 425 nanoparticles were centrifuged at 20000 rpm for 25 min. After that, 0.5 mL of the supernatants were diluted with ethanol and assayed by UV spectrophotometry at 286 nm [16].

8.3 Results

Figure 9:
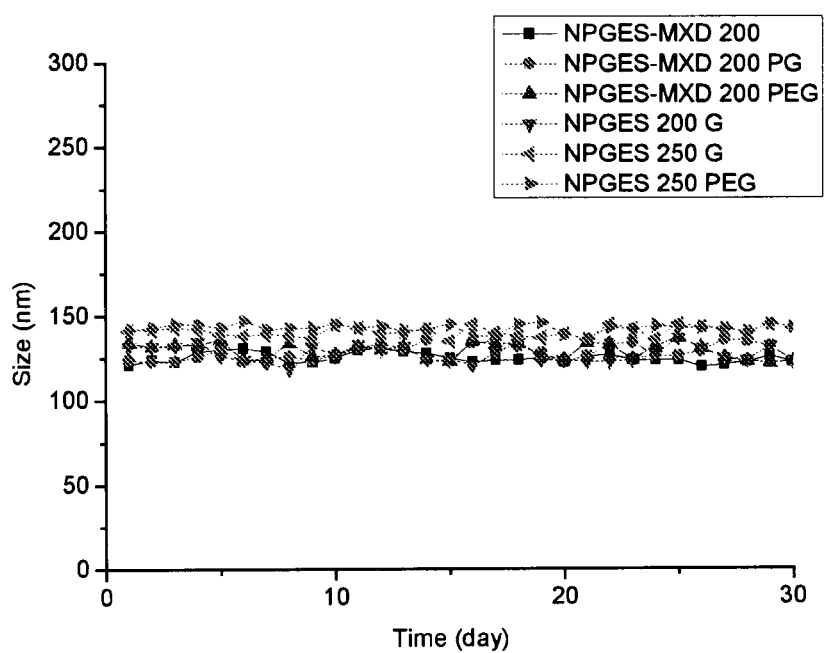
FIG. 9. Monitoring of the nanoparticles size of Minoxidil-loaded GANTREZ® ES 425 nanoparticles (MXD-GANTREZ® ES 425 nanoparticles). The formulations investigated were MXD-loaded GANTREZ® ES 425 nanoparticles with 200 and 250 mg MXD without excipients or with propylene glycol (PG), glycerol (G) or polyethylene glycol 400 (PEG).

Generally, GANTREZ® ES 425 nanoparticles loaded with MXD with or without excipients displayed a homogenous small size of about 130 nm (PDI 0.1) with negative charge zeta potential (−54 mV). The encapsulation efficiency was considerably high in both formulations, the one loaded with 200 mg of MXD and the other one loaded with 250 mg of MXD, and was about 70% of the initial amount of MXD added (Table 8). In the physical stability study of the formulations, the daily size monitoring and macroscopical visualization during 30 days under the aggressive physical conditions did not indicate any change in the size (FIG. 9) or precipitate in the polypropylene or glass containers. These results confirmed that the non-encapsulated MXD still remained dissolved in the aqueous suspension of the nanoparticles.

TABLE 8

Physico-chemical characteristics of MXD-loaded Gantrez ® ES 425 nanoparticles.
Data expressed as mean ± SD (n = 6)

|  | $a$ Size (nm), (±SD) | $b$ PDI | $c$ Zeta potential (mV), (±SD) | $d$ % yield, (±SD) | $e$ % Encapsulation efficiency of MXD (±SD) |
| --- | --- | --- | --- | --- | --- |
| NPGES-MXD 200 | 129.14 (1.00) | 0.100 | −54.67 (1.95) | 96.35 (3.91) | 72.57 (5.14) |
| NPGES-MXD 200 PG | 130.21 (1.17)* | 0.116 | −56.11 (2.54) | 95.32 (5.17) | 68.51 (7.67) |
| NPGES-MXD 200 G | 132 (3.60)* | 0.113 | −55.10 (3.24) | 98.82 (2.09) | 68.37 (8.93) |
| NPGES-MXD 200 PEG | 127 (2.60) | 0.136 | −55.99 (2.08) | 95.09 (4.16) | 63.92 (3.56) |
| NPGES-MXD 250 | 142.21 (1.17)* | 0.192 | −58.27 (2.94) | 96.62 (1.55) | 68.51 (5.57) |
| NPGES-MXD 250 G | 139 (2.74)* | 0.204 | −59.14 (1.29) | 98.18 (0.04) | 68.37 (1.55) |
| NPGES-MXD 250 PG | 145 (1.05)* | 0.190 | −57.99 (0.09) | 95.52 (2.95) | 63.92 (3.07) |

NPGES-MXD 200: Minoxidil-loaded Gantrez ® ES 425 nanoparticles with 200 mg MXD
NPGES-MXD 250: Minoxidil-loaded Gantrez ® ES 425 nanoparticles with 250 mg MXD
PG, G and PEG: Excipients added to the nanoparticles formulations, namely propylene glycol (PG), glycerol (G) or polyethylene glycol 400 (PEG).
$a$ Determination of the nanoparticles size (nm) by photon correlation spectroscopy.
$b$ Polydispersity Index.
$c$ Determination of the zeta potential by electrophoretic laser Doppler anemometry.
$d$ The percentage of the nanoparticles formed from the initial amount of the polymer used.
$e$ % Encapsulation efficiency: Percentage of the amount of encapsulated MXD in Gantrez ® ES 425 nanoparticles in relation with the initial amount used.
*$P < 0.05$; GES-MXD 200 versus GES-MXD 200 control nanoparticles [Gantrez ® ES nanoparticles obtained from Gantrez ® ES (GES-NP)] (Student t-Test).

Figure 10:
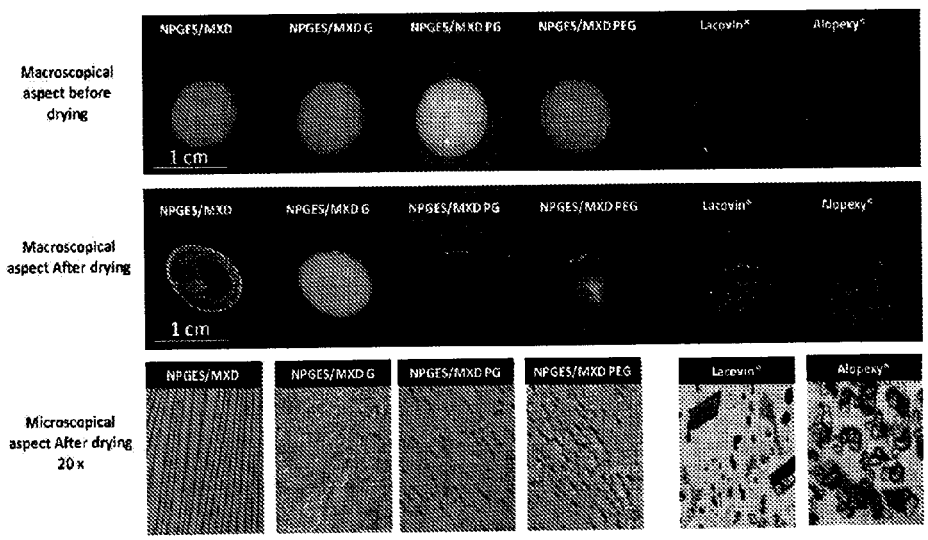
FIG. 10. Macroscopical and microscopical visualization for MXD-loaded GANTREZ® ES 425 nanoparticles formulation without excipients or with propylene glycol (NPGES/MXD PG), glycerol (NPGES/MXD G) or polyethylene glycol 400 (NPGES/MXD PEG) and for commercial products (LACOVIN® and ALOPEXY®) before and after drying. All formulations were used at similar MXD concentration (2% w/v).

On the other hand, a macroscopical and microscopical visualization assay was performed for GANTREZ® ES 425 nanoparticles containing MXD (2%) with different excipients, a commercial formulation of MDX containing ethanol, propylene glycol, and water (LACOVIN® 2%), and a commercial formulation containing gamma-cyclodextrins, propylene glycol, ethanol, and water (ALOPEXY® 2%). FIG. 10 describe both macroscopical and microscopically aspects of the formulations applied. In this figure, the aspect of the samples before drying was milky for the nanoparticles formulations and transparent for the commercial products. However, after 2 hours drying, a crystalline film was observed for commercial products with a visual big white crystal layer. On the other hand, samples of GANTREZ® ES 425 nanoparticles containing PEG 400 or propylene glycol showed a transparent adhesive film without any observation of big crystalline precipitate. The samples containing GANTREZ® ES 425 nanoparticles with glycerol had a slight milky elegant appearance without any crystalline precipitate. In addition, MXD-loaded GANTREZ® ES 425 nanoparticles without excipients showed an appearance of a dry crackly thin film but without any visual crystals (FIG. 10). Furthermore, MXD-loaded GANTREZ® ES 425 nanoparticles with different excipients (NPGES-MXD G, NPGES-MXD PEG and NPGES-MXD PG) did not form a dry film after 12 hours. However, dry precipitates were observed within 2 hours for commercial products and within 4 hours for MXD-loaded GANTREZ® ES 425 without excipients. Microscopical examination confirmed the macroscopical results, i.e., big crystals were observed for commercial products LACOVIN® and ALOPEXY® within the first 2 hours. There were significant differences between the aspects of the residual film for MXD nanoparticles formulations. In this context, MXD-loaded GANTREZ® ES 425 nanoparticles without excipients shown a striated easily break film (NPGES-MXD). This phenomena was not observed for dry films of MXD nanoparticles containing excipients such as propylene glycol, glycerol or PEG. In addition, no big crystals were observed for any of the dry films containing the MXD nanoparticles formulations.

Figure 11:
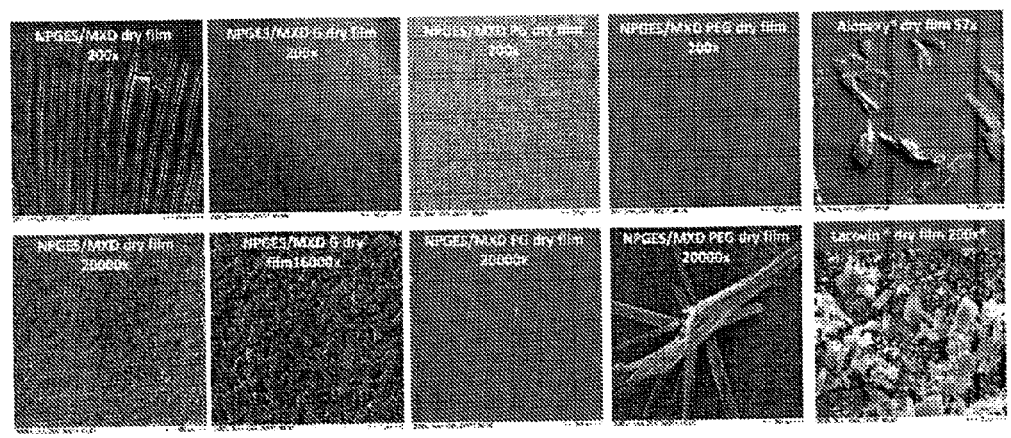
FIG. 11. Scanning electron microscopy (SEM) performed for MXD GANTREZ® ES 425 nanoparticles without excipients (NPGES/MXD) or with excipients glycerol (NPGES/MXD G), propylene glycol (NPGES/MXD PG) and PEG 400 (NPGES/MXD PEG) and for commercial products (LACOVIN® and ALOPEXY®).

FIG. 11 shows the SEM performed for the MXD-loaded GANTREZ® ES 425 nanoparticles formulations and MXD commercial formulations. The data obtained from this figure exactly correlated and confirmed the results shown in FIG. 10. For commercial products (LACOVIN® and ALOPEXY®), big crystals precipitates were observed. On the other hand, no big crystals were observed for the MXD nanoparticles formulations (NPGES/MXD, NPGES/MXD G, NPGES/MXD PG and NPGES/MXD PEG). Both MXD nanoparticles formulations without excipients (NPGES/MXD) and MXD nanoparticles with glycerol (NPGES/MXD G) shown the presence of a homogeneous film containing the nanoparticles with homogeneous size distribution. Surprisingly, no nanoparticles were detected in dry films containing MXD-loaded GANTREZ® ES 425 nanoparticles with PG or PEG, what may be due to the solubility of the polymers in these excipients after water evaporation. It is important to note that some big precipitates (polymeric film layers) were observed for the formulation containing PEG 400 what may be related to the interaction of some carboxylic groups of the polymer with PEG. Further investigations are needed to identify the type and nature of this precipitate. Finally, all films had an elegant appearance with light adhesive tacky texture.

Example 9

Bioadhesive Affinity of GANTREZ® ES Nanoparticles to Hair

The objective of this study was to investigate the adhesive capacity of GANTREZ® ES nanoparticles to hair. For this purpose, fluorescently labelled GANTREZ® ES 425 nanoparticles with Rhodamine B were used. Rhodamine B-loaded GANTREZ® ES 425 nanoparticles were prepared by the addition of the fluorescent hydrophilic molecule (200 μg) pre-dissolved in 200 μL of bidistilled water to 5 mL of a GANTREZ® ES 425 ethanolic solution (50 mg/mL). The solution was left under magnetic stirring for 5 min at room temperature, and then 9.3 mL of distilled water were added to form the nanoparticles. The resulting nanoparticles suspension was evaporated under reduced pressure using a rotavapor (Büchi R-144, Switzerland) to eliminate ethanol and the mount of Rhodamine B encapsulated in GANTREZ® ES 425 nanoparticles was assayed as described in Example 5. After Wood, 500 μL of glycerol were added to the aqueous suspension of the nanoparticles to achieve 10 mL final volume of the nanoparticles suspension with glycerol concentration at 5% (v/v). For the adhesion assay, normal black woman hair (100 cm long) was washed with soap and hot water (70° C.) during 5 minutes. Then, the hair was cut into 5 cm long portions and divided in two groups (M1 and M2). Hair samples were dried by hot air derived from a hair dryer during 5 min. After that, the dry hair was immersed in fluorescently labeled GANTREZ® ES 425 nanoparticles for 30 seconds, and then it was let to dry at room temperature. After drying, the hair of group M1 was visualized by fluorescence and scanning electron microscopy (SEM). Hair sample of group M2 were washed again with soap and hot water (70° C.) during 5 minutes and then visualized by fluorescence and SEM as described for group M1. In order to quantify the amount of the nanoparticles adhered to the hair in both groups (M1 and M2), hair was digested in NaOH 3 M to dissolve the polymeric nanoparticles that had adhered to the hair and to extract Rhodamine B. The amount of the fraction of the nanoparticles adhered to hair was assayed by spectrofluorimetry at 540 nm (excitation wavelength) and 580 nm (emission wavelength) (GENios, TECAN, Groedig, Austria) in order to estimate the fraction of nanoparticles adhered to hair. Data were represented by the adhered fraction for 1 mg of hair or for $cm^2$ of hair surface area.

Figure 12:
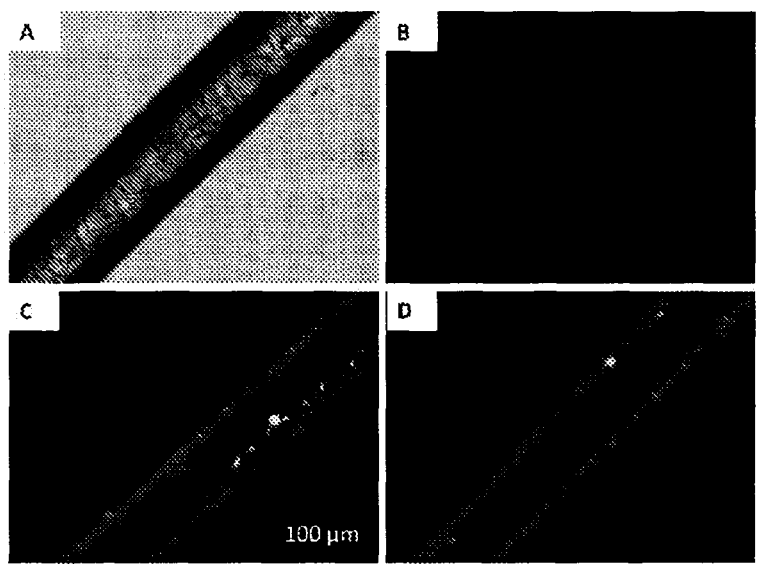
FIG. 12. Microscopical characterization for hair samples. Hair structure 20x, (A) fluorescence microscopy for normal hair without fluorescently labelled GANTREZ® ES 425 nanoparticles; and (B) fluorescence microscopy for normal hair of groups M1 (C) and group M2 (D).
Figure 13:
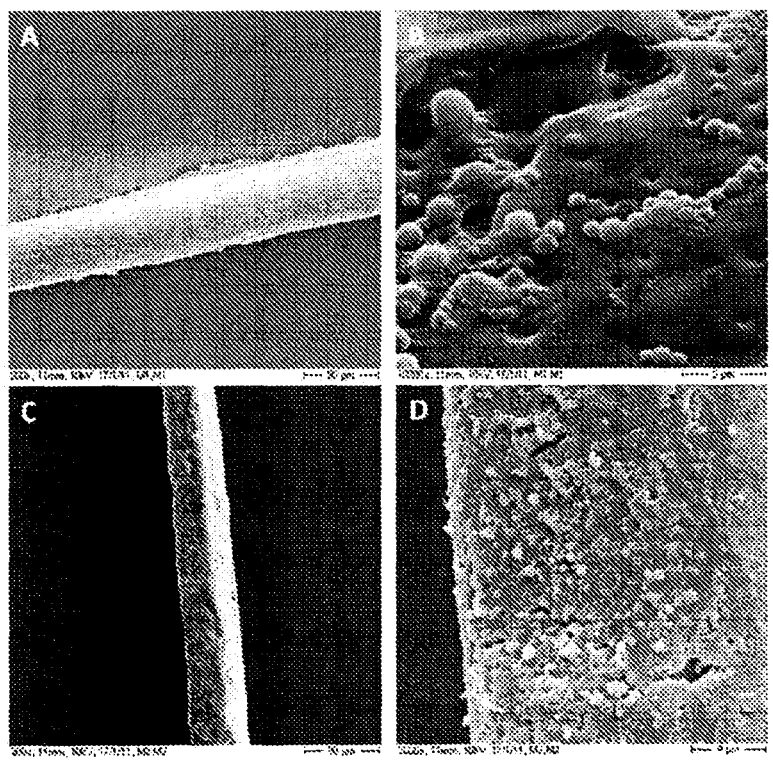
FIG. 13. Scanning electron microscopy (SEM) for normal hair with incubated with GANTREZ® ES 425 nanoparticles for hair group M1 (A, B) and hair group M2 (C, D).

It has been found that the amount of the adhered fraction on the hair samples was about 9.5 μg nanoparticles/$cm^2$ hair surface area for group M1. In the other group of hair samples (M2), although the amount of adhered fraction of the nanoparticles was reduced by hair washing, it was found that the nanoparticles still adhered to the hair surface (3.5 μg nanoparticles/$cm^2$ hair surface area). The fluorescence and SEM (FIGS. 12 and 13) confirmed the initial high adhesive affinity of GANTREZ® ES 425 nanoparticles to the hair surface. In addition, the dry film of the nanoparticles adhered on the hair surface in group M1 resisted the washing and high temperature conditions and nanoparticles were maintained adhered to the surface of hair as seen for group M2. Further, the aspect of the hair containing the GANTREZ® ES nanoparticles film was elegant, transparent, brilliant and did not show any black residues after drying.

Example 10

Ex Vivo Mucosal Affinity Study of GANTREZ® ES Nanoparticles in Porcine Buccal Mucosa

10.1 Quantitative Bioadhesion Assay

In order to study the bioadhesion capability (bioadhesivity) and mucosal affinity of GANTREZ® ES nanoparticles, freshly obtained porcine buccal mucosa and tongue dorsal surface were used. For this purpose, porcine heads were obtained from a local slaughterhouse and the buccal mucosa or tongue dorsal mucosa were surgically isolated. The epithelium cleaned from underlying connective tissues using surgical scissors and cut in 2 $cm^2$ circular areas. Then, tissue samples were stored in PBS at 4° C. and used within 2 hours. Tissue was clamped between tow flat flange of Franz cell compartments and different samples of nanoparticles formulations were deposited in the donor compartment. In this case, the nanoparticles formulations were 500 μL of:
  (i) an aqueous suspension of fluorescently labelled GANTREZ® ES 225 nanoparticles with Rhodamine B prepared as disclosed in Example 9, without the use of glycerol,
  (ii) an aqueous suspension of fluorescently labelled GANTREZ® AN nanoparticles with Rhodamine B,
  (iii) fluorescently labelled GANTREZ® ES 225 nanoparticles resuspended in sodium hyaluronate gel (0.75% w/v), and
  (iv) fluorescently labelled GANTREZ® AN nanoparticles resuspended in sodium hyaluronate gel (0.75% w/v).

For sample application to the mucosal surfaces, one side of the donor compartment (1 $cm^2$ of the tissue) was exposed to 500 μL aqueous nanoparticles suspension only for 30 seconds with turbulence agitation to simulate buccal mouth wash conditions. Then, samples were retired from the compartment and formulations were exposed to 75 mL simulated salivary fluids [19]-[20] at 37° C. for 6 hours. In case of sodium hyaluronate gel applications, equivalent amount of nanoparticles incorporated in hyaluronate gel was left in the compartment. Tissue samples were removed at different time intervals and 1 $cm^2$ area, which was exposed to the sample during the experiment, were cut and isolated. The amount of adhered nanoparticles was assayed as previously described [12]. Briefly, each mucosal segment was digested with 2 mL of NaOH 3M for 24 h. The samples were diluted to 3 mL by adding NaOH 3M, vortexed for 10 min and centrifuged at 2,000×g for 30 min. Finally, the amount of Rhodamine B was assayed by spectrofluorimetry at 540 nm (excitation wavelength) and 580 nm (emission wavelength) (GENios, TECAN, Groedig, Austria) in order to estimate the fraction of adhered nanoparticles to the mucosa. The standard curves of the bioadhesion study were prepared by addition of Rhodamine B solutions in NaOH 3M (0.05-1 μg/mL) with control tissue (r>0.996).

10.2 Fluorescence Microscopy Tissue Visualization

The distribution of Rhodamine B-loaded GANTREZ® ES 225 nanoparticles formulations in buccal and tongue mucosa was visualized by fluorescence microscopy. For that purpose, the mucosal surface samples exposed to different formulations were removed and washed with PBS at 2.5 h post exposure. Then, the mucosa were cut in small pieces by surgical scissors and treated with the tissue proceeding medium OCT (optimum cutting temperature) (Sakura, Netherlands) and frozen in liquid nitrogen. Tissue samples were cut into 5 μm longitudinal sections in a cryostat (2800 Frigocut E, Reichert-Jung, Germany), attached to poly-L-lysine pre-coated slides (Sigma, Spain) and stored at −20° C. before fluorescence microscopic visualization.

10.3 Results

Figure 14A:
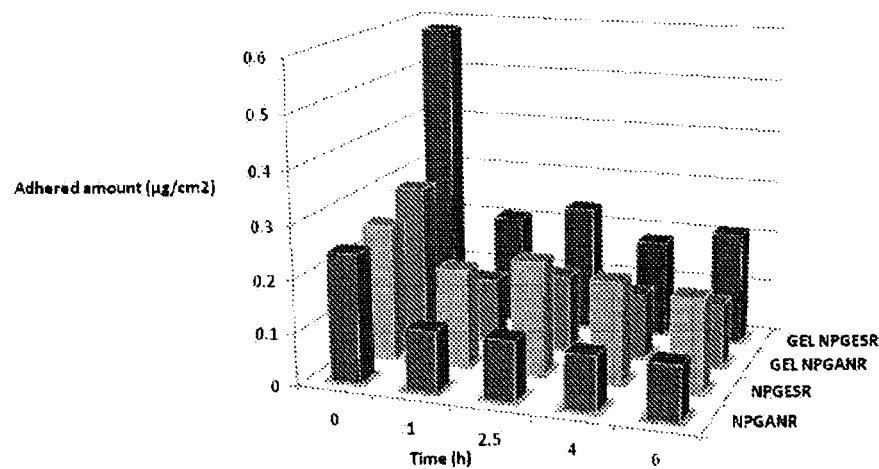
FIG. 14A. Assay of the accumulative adhered amount of nanoparticles formulations in porcine buccal mucosal tissue at different times. The formulations were: aqueous suspension of fluorescently labelled GANTREZ® ES 225 nanoparticles with Rhodamine B (NP GESR); aqueous suspension of fluorescently labelled GANTREZ® AN nanoparticles with Rhodamine B (NP GANR); fluorescently labelled GANTREZ® ES 225 (GEL NPGESR); or fluorescently labeled GANTREZ® AN nanoparticles (GEL NPGANR) resuspended in a sodium hyaluronate gel (0.75% w/v). Each value was represented by the mean (n=3; SD was less than 20% of the mean).
Figure 14B:
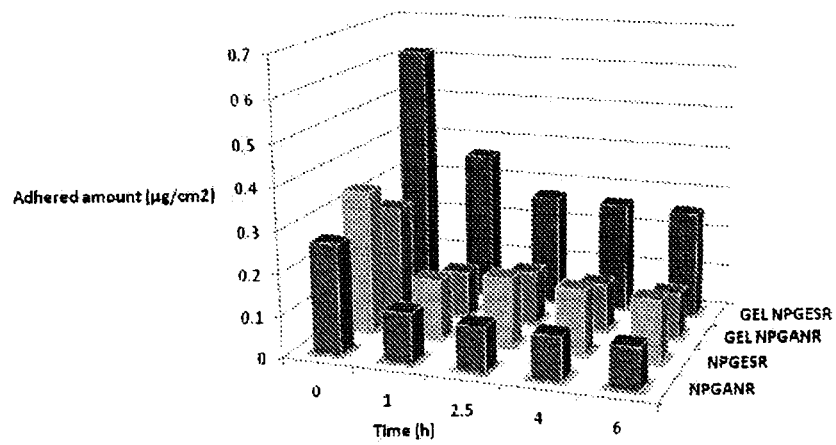
FIG. 14B. Assay of the accumulative adhered amount of nanoparticles formulations in porcine tongue mucosal tissue at different times. The formulations were: aqueous suspension of fluorescently labelled GANTREZ® ES 225 nanoparticles with Rhodamine B (NP GESR); aqueous suspension of fluorescently labelled GANTREZ® AN nanoparticles with Rhodamine B (NP GANR); fluorescently labelled GANTREZ® ES 225 (GEL NPGESR); or fluorescently labeled GANTREZ® AN nanoparticles (GEL NPGANR) resuspended in a sodium hyaluronate gel (0.75% w/v). Each value was represented by the mean (n=3; SD was less than 20% of the mean).

FIGS. 14A and 14B represents the accumulative quantity of adhered fraction of nanoparticles (NP) formulation per $cm^2$ of tissue (μg NP/$cm^2$ tissue) for GANTREZ® ES 225 and GANTREZ® AN copolymers in both porcine buccal and tongue dorsal mucosa, respectively. Generally, GANTREZ® ES 225 nanoparticles (NP GESR) shown a higher adhesive capacity than GANTREZ® AN nanoparticles (NP GANR). However, both types of nanoparticles displayed a similar initial adhesive force at time 0 (0 hour). At 1, 2.5, 4 and 6 hours, the accumulative adhered fractions of GANTREZ® ES 225 nanoparticles, in both types of porcine mucosa, were approximately 2-3 times higher than accumulative adhered fractions of GANTREZ® AN nanoparticles ($P<0.05$). In the case of gel formulations containing nanoparticles, it was observed that hyaluronate gel enhances the initial adhesive capacity of GANTREZ® ES 225 nanoparticles (GEL NPGESR) about 2-fold more than the GANTREZ® ES nanoparticles suspension at time 0. In addition, at 1, 2.5, 4 and 6 hours, a significant enhancement in the bioadhesive capacity was observed for the gel containing GANTREZ® ES 225 nanoparticles. Surprisingly, this phenomenon was not observed in the case of GANTREZ® AN gel formulations (GEL NPGANR), wherein no significant differences between aqueous suspensions (NP GANR) and gel containing GANTREZ® AN nanoparticles (GEL NPGANR) were observed.

Figure 15:
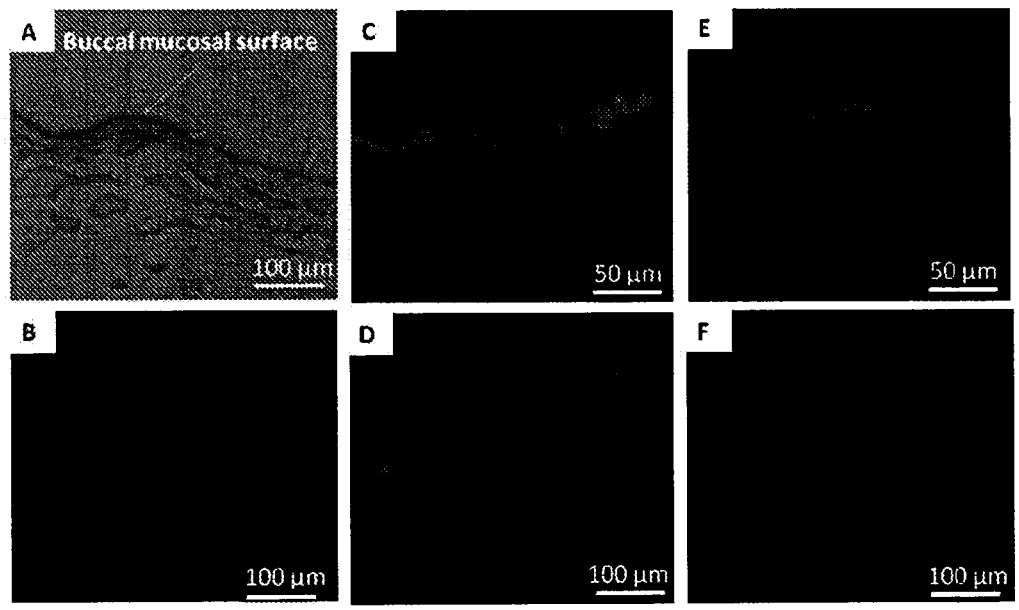
FIG. 15. Tissue visualization of buccal mucosa cross sections: (A) optical microscopy of buccal mucosa; (B) by fluorescence microscopy of buccal tissue without nanoparticles; (C) Rhodamine B-loaded GANTREZ® ES 225 nanoparticles at 0.5 h post administration; (D) Rhodamine B-loaded GANTREZ® AN nanoparticles at 0.5 post administration; (E) Rhodamine B-loaded GANTREZ® ES 225 nanoparticles at 2.5 h post administration; and (F) Rhodamine B-loaded GANTREZ® AN nanoparticles at 2.5 h post administration.

FIG. 15 shows the fluorescence microscopy images of both buccal mucosal tissues after 0.5 and 2.5 h of the administration of fluorescently labelled nanoparticles formulations. Control tissue (without nanoparticles formulation) shown low fluorescence intensity in the tissue (FIG. 15B). Rhodamine B-loaded GANTREZ® ES nanoparticles displayed a high fluorescence intensity at the mucosal layer of the buccal mucosa at 0.5 hour post tissue incubation with salivary fluid (FIG. 15C) which was similar at 2.5 h (FIG. 15E). On the other hand, the tissue fluorescence intensity of GANTREZ® AN nanoparticles was decreased from 0.5 to 2.5 h post incubation to be approximately similar to the control ones at 2.5 h post-administration (FIGS. 15 D and 15F). These data confirm that GANTREZ® ES 225 has a higher affinity and longer residence time in the buccal mucosa than GANTREZ® AN nanoparticles. In addition, it was observed that, in all the cases, the nanoparticles did not penetrate to the sub-mucosal tissue.

Figure 16:
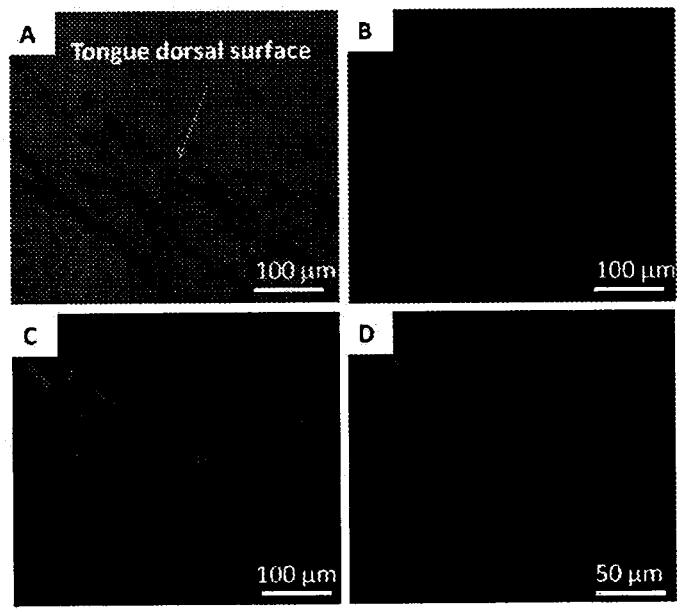
FIG. 16. Tissue visualization of porcine tongue dorsal surface cross sections with tiny hair-like projections called "filiform papillae". (A) optical microscopy tongue dorsal mucosal surface; (B) Rhodamine B-loaded GANTREZ® AN nanoparticles at 2.5 h post administration; (C, D) Rhodamine B-loaded GANTREZ® ES 225 nanoparticles at 2.5 h post.

FIG. 16 shows the fluorescence microscopy images in tongue dorsum mucosal surface at 2.5 h of the administration of fluorescently labelled nanoparticles formulations. In a tissue (dorsal mucosa of the porcine tongue) which is similar to the buccal mucosal tissue, GANTREZ® ES 225 nanoparticles (FIGS. 16C and 16D) shown a higher affinity and longer residence time than GANTREZ® AN nanoparticles (FIG. 16 B).

Overall Discussion of Examples 1-10

Inventors have optimized the solvent evaporation method and the in situ self-assembly technique for the production of bioadhesive nanoparticles (matrix nanospheres or shell nanocapsules) manufactured with a half ($C_1$-$C_4$) alkyl ester of a PVM/MA copolymer.

In this context, it has been surprisingly found that mixing a pharmaceutically or cosmetically acceptable solvent such as ethanol or a polyol (e.g., propylene glycol) containing said half ($C_1$-$C_4$) alkyl ester of a PVM/MA copolymer, with an aqueous solution, optionally containing one or more excipients, allowed the spontaneous formation of nanoparticles with a very homogeneous small size. In the case of the solvent evaporation method, the average size of the nanoparticles so obtained was about 125-145 nm, typically about 130-135 nm, with a high manufacture yield (around 98%).

In addition, it was possible to obtain in situ self-assembled nanoparticles (SANP) based on said half ($C_1$-$C_4$) alkyl esters of PVM/MA copolymers. This in situ self-assembly technique allows the in situ formation of the nanoparticles and the encapsulation of a product of interest (POI) in said nanoparticles at the time the half ($C_1$-$C_4$) alkyl ester of PVM/MA copolymer contacts with an aqueous medium, e.g., water or a body fluid such as the gastrointestinal tract fluid.

The simplicity of the process for the production of the nanoparticles of the invention (based on the use of a half ($C_1$-$C_4$) alkyl ester of a PVM/MA copolymer) reduces the industrial scale cost due to the simplicity for obtaining said nanosystems without the use of any special apparatus described for nanosystems based on other PVM/MA derivatives, e.g., poly (methyl vinyl ether-co-maleic anhydride) (PVM/MA) copolymers (GANTREZ® AN).

An important advantage of the nanoparticles of the invention consists in that the long-term stability (degradation rate) in aqueous medium of said nanoparticles of the invention is higher than that of the GANTREZ® AN nanosystems (FIG. 2), i.e., the nanoparticles of the invention show a lower degradation rate in a long-term stability study in aqueous medium than that of the GANTREZ® AN nanosystems.

Emulsion techniques have been applied to obtain GANTREZ® AN nanosytems which show stability in short-term stability studies of said nanosystems in aqueous media due to the hydrolysis of GANTREZ® AN to GANTREZ® S. Similarly, in an aqueous medium, these nanoparticles can be dissolved quite rapid. The stabilization of GANTREZ® AN nanosystems in aqueous media requires a chemical modification with polyamine compounds, toxic cross-linkers, such as 1,3-diaminopropane (DP), or immunogenic molecules such as bovine serum albumin (BSA). The addition of DP only weakly enhances the stability of GANTREZ® AN nanoparticles in PBS to achieve a hydrolysis rate of 20% within 2 hours vs 40% for non-cross-linked GANTREZ® AN nanoparticles. Other disadvantages of the cross-linking of PVM/MA nanoparticles include the significant increase of the nanoparticles average size and the dramatic decrease of the bioadhesive capacity of the nanosystems. However, the nanoparticles of the invention do not need to be cross-linked, and, consequently, said nanoparticles can be commercialized in the form of an aqueous suspension without the need to use toxic cross-linkers molecules, lyophilization or other drying techniques. In addition, they can be easily incorporated in many dosage forms (e.g., in liquid, semi solid or solid form) which are widely used in cosmetic and pharmaceutical industry.

The nanoparticles of the invention have shown a high capacity for encapsulating different types of molecules, such as large hydrophilic compounds, e.g., BSA (Example 4) and small hydrophilic compounds, e.g., Rhodamine B (Example 5). However, some difficulties have been reported in connection with the ability of GANTREZ® AN nanoparticles for incorporating hydrosoluble drugs in the organic phase of the polymer (a solution of GANTREZ® AN in acetone). As it is known, hydrosoluble drugs are not soluble in acetone and may form big size crystals that can interfere with the formation of nanoparticles once the hydroalcoholic solution added to precipitate GANTREZ® AN in the form of nanosystems. For that reason, hydrosoluble drug, 5-fluorouridine (FURD), could be loaded in GANTREZ® AN nanoparticles only by incubating the drug with the previously formed nanoparticles and, consequently, a very low encapsulation efficiency was obtained (about 13%).

On the other hand, the production of core-shell vesicular nanocapsules containing an oil has been optimized by the present invention. The lemon essential oil was efficiently encapsulated in the nanoparticles of the invention (about 82% of encapsulation efficiency) and the average size of the nanocapsules provided by the instant invention, based on a half $(C_1-C_4)$ alkyl ester of a PVM/MA copolymer, was homogenous (about 212 nm) [Example 2].

In connection with compounds which are poorly soluble in water, complexing agents such as cyclodextrins (CDs), or solubilizers including poly ethylene glycols and amino acids (Glycin), are requested for encapsulating hydrophobic drugs such as paclitaxel in GANTREZ® AN-based nanoparticles. In fact, if complexing agents or solubilizers are not used, the encapsulation efficiency of the hydrophobic (lipophilic) compound was less than 1% of the initial amount added. Other types of PVM/MA derivatives copolymers, for example, GANTREZ® MS-based microspheres prepared by double emulsion techniques shown a low encapsulation efficiency of hydrophobic compounds (about 30% for Triclosan).

However, according to this invention, it is possible to encapsulate compounds which are poorly or scarcely soluble in water, e.g., hydrophobic or lipophilic compounds, in nanoparticles based on a half $(C_1-C_4)$ alkyl ester of a PVM/MA copolymer (invention), with high encapsulation efficiencies. Examples 6, 7 and 8 illustrate the incorporation of hydrophobic drugs, such as Ketoconazole (KTZ), Triclosan (TRI) and Minoxidil (MXD) in nanoparticles based on half $(C_1-C_4)$ alkyl esters of PVM/MA copolymers (invention). As it is shown in said Examples 6-8, the encapsulation efficiency of KTZ in said nanoparticles was about 97% of the initial amount added (Table 6), the encapsulation efficiency of TRI was about 97% (Table 7), and the encapsulation efficiency of MXD was about 72% (Table 8). Further, the in situ self-assemby technique for producing in situ self-assembled nanoparticles (SANP) was applied to encapsulate Triclosan; a high encapsulation efficiency of Triclosan in SANP based on a half $(C_1-C_4)$ alkyl ester of a PVM/MA copolymer (invention) was obtained (around 82%—Table 7). The association of said drugs (KTZ, TRI and MXD) to nanoparticles based on a half $(C_1-C_4)$ alkyl ester of a PVM/MA copolymer (invention) did not affect the percentage of nanoparticles formed from the initial amound of the copolymer used, which were maintained in the range of 95% or higher (Tables 6-8). On the other hand, it has been observed that the use of nanoparticles based on a half $(C_1-C_4)$ alkyl ester of a PVM/MA copolymer (invention) enhanced the solubility of scarcely or poorly water soluble compounds resulting in an effective inhibition of crystal formation of the corresponding drug in aqueous media.

Example 6 discloses the production of Ketoconazole-loaded nanoparticles based on a half $(C_1-C_4)$ alkyl ester of a PVM/MA copolymer (invention); said nanosystem can be applied as a drug delivery system for the controlled release of scarcely or poorly water soluble antifungal agents. Solid lipid nanoparticles (SLN) and nanostructured lipid carriers (NLC) carrying Ketoconazol (KTZ) were obtained by the hot high pressure homogenization technique, but lipid formulations of KTZ showed some physical and chemical instability. However, the KTZ-loaded nanoparticles based on a half $(C_1-C_4)$ alkyl ester of a PVM/MA copolymer provided by this invention, containing KTZ at different polymer concentrations, were homogeneous (about 200-235 nm of average size) which indicated the absence of drug crystals whose size is around 2-10 μm. These drug crystals were observed only after the treatment of KTZ alcoholic solutions by the same way as the half $(C_1-C_4)$ alkyl ester of a PVM/MA copolymer alcoholic solutions containing KTZ used to form the nanoparticles. This fact was observed after visualization of both KTZ crystals and KTZ-loaded nanoparticles based on half $(C_1-C_4)$ alkyl esters of PVM/MA copolymers by scanning electron microscopy (SEM) (FIGS. 7B and 7A, respectively). Similar results from SEM were obtained for nanoparticles left at room temperature for at least 2 months wherein no crystal growth or formation was observed (FIG. 7C). These results indicate that KTZ-loaded nanoparticles based on half $(C_1-C_4)$ alkyl esters of PVM/MA copolymers enhance the aqueous solubility of hydrophobic drugs such as KTZ and inhibit the crystallization or precipitation of KTZ in the final aqueous suspension of said nanoparticles.

Similarly, the encapsulation efficiency of Triclosan (TRI) was approximately 97% of the initial amount added in the TRI-loaded nanoparticles based on half $(C_1-C_4)$ alkyl esters of PVM/MA copolymers (invention) obtained according to the solvent displacement method and about 80% for TRI-loaded nanoparticles of the invention obtained by the in situ self-assembly technique. The sizes of the TRI-loaded nanoparticles provided by the present invention containing TRI at different concentrations (0.12% and 0.2% (w/v)) in the aqueous suspension of TRI-loaded nanoparticles based on half $(C_1-C_4)$ alkyl esters of PVM/MA copolymers were homogeneous (about 140 nm) which indicated the absence of drug crystals whose size is around 50-200 μm (FIG. 8A). These drug crystals were observed only after the treatment of TRI alcoholic solutions by the same way as the half $(C_1-C_4)$ alkyl ester of a PVM/MA copolymer alcoholic solutions containing TRI used to form the nanoparticles. This fact was observed after visualization of both TRI crystals and TRI-loaded nanoparticles based on half $(C_1-C_4)$ alkyl esters of PVM/MA copolymers by SEM (FIG. 8B). These results indicate that TRI-loaded nanoparticles based on half $(C_1-C_4)$ alkyl esters of PVM/MA copolymers enhance the aqueous solubility of hydrophobic drugs such as TRI due to the absence of drug crystals in the nanoparticles formulation. Further, it appears that the inclusion of TRI in said nanoparticles provided by the present invention inhibits the crystals formation (crystallization) and precipitation of TRI in the final aqueous suspension of said nanoparticles.

Different studies describe the inclusion of TRI en polymeric microparticles and nanoparticles through the use of complex emulsification techniques and toxic organic solvents. In this context, TRI-loaded EUDRAGIT® nanoparticles for the treatment of acne were prepared by the emulsification-diffusion by solvent displacement method, using EUDRAGIT® E 100 as polymer. Although a high encapsulation efficiency was obtained (95.5%), the production of the nanoparticles requires complex techniques including an emulsification process using a toxic organic solvent (methyl ethyl ketone) [17]. Similarly, TRI-loaded nanoparticles were prepared by using poly(D,L-lactide-co-glycolide) (PLGA), poly(D,L-lactide) (PLA) and cellulose acetate phthalate (CAP) and poly(vinyl alcohol) (PVA) as stabilizer. These TRI-loaded nanoparticles were designed for periodontal treatment based on non-bioadhesive polymers such as PLGA. The encapsulation efficiency was about 63% and complex emulsification-diffusion process was applied to obtain the nanoparticles. Further, chitosan/gelatin microcapsules containing TRI were prepared by a spray drying method. Mucoadhesive, TRI-loaded polymer microspheres for application to the oral cavity were prepared by double-emulsion solvent evaporation technique, where TRI was incorporated into microspheres prepared from GANTREZ® MS-955, CARBOPOLE® 974P, polycarbophil or chitosan. Generally, the drug loading efficiency of TRI was about 30% for all polymers used except for chitosan (about 70%); however, some difficulties to encapsulate TRI with this technique were reported because the lipophilic TRI tends to migrate into the outer oil phase.

Minoxidil (MXD) is being used topically in treating alopecia androgenetica. Minoxidil was commonly incorporated in a mixture of solvents, mainly propylene glycol:ethanol:water. The typical side effects of this topical treatment include irritative dermatitis going along with pruritus, erythema, scaling and dryness, which occur especially at the onset of the therapy. In some cases, allergic contact dermatitis or exacerbation of seborrheic dermatitis has been reported. Propylene glycol (PG) may cause some patients a pruritus and scaling of the scalp which may be the common causes of these symptoms includes irritant contact dermatitis, allergic contact dermatitis, or an exacerbation of seborrheic dermatitis.

On the other hand, published works describe experiments related to the evaporation of solvents from the PG:ethanol: water (20:60:20, v/v) mixture. One of the main problems of formulations containing this solvent mixture is the evaporation post-application on the scalp. The evaporation of ethanol post-application can form concentrated PG and thus to achieve supersaturation leading to drug precipitation. The amount of formulation applied influences the rate of concentration and, thus, the time at which MXD precipitates. The precipitation limits the amount of MXD that can be absorbed and leads to poor percutaneous absorption of the drug. Similarly, other study discusses the evaporation time and its relation to MXD concentration, wherein ethanol may have been evaporated after the first half-hour and after 2 h, the only vehicle component remaining was PG. For the 3% MXD solution, MXD remained in the vehicle for the entire 2 h observation period, but seeding immediately produced a copious precipitate confirming the presence of a supersaturated solution. To some extent, the crystal formation of MXD on the scalp may cause the formation of dandruff like aspect with is not elegant for hair appearance.

These results were in accordance to the results obtained in this invention, wherein a macroscopical and microscopical gross assay was performed for (i) MXD-loaded nanoparticles based on half ($C_1$-$C_4$) alkyl esters of PVM/MA copolymers containing MXD (2%) with different excipients (invention), (ii) a commercial formulation of MDX containing ethanol, PG, and water (LACOVIN® 2%), and (iii) a commercial formulation containing gamma-cyclodextrins, PG, ethanol and water (ALOPEX® 2%). In this context, data obtained from FIG. 10 indicate that the aspect of the samples before drying was milky for the nanoparticles formulation (i) and transparent for the commercial products (ii) and (iii). However, after 2 hours drying, a crystalline film started to be observed for the commercial products with a visual big white crystal layer. The sample containing the MXD-loaded nanoparticles provided by the invention with glycerol had a slight milky elegant appearance without any crystalline precipitate. Furthermore, MXD-loaded nanoparticles provided by the present invention with different excipients (NPGES-MXDG, NPGES-MXD PEG and NPGES-MXD PG) did not form a dry film after 12 hours. However, dry precipitates were observed within 2 hours for the commercial products and within 4 hours for the MXD-loaded nanoparticles of the invention without excipients. Microscopical examination confirmed the macroscopical results, where big crystals were observed for the commercial products LACOVIN® 2% and ALOPEX® 2% within the first 2 hours. There were significant differences between the aspect of the residual film for the MXD-loaded nanoparticles formulations. In this context, MXD-loaded nanoparticles of the invention without excipients shown a striated easily break film (NPGES-MXD). This phenomena was not observed for dry films of MXD-loaded nanoparticles of the invention containing excipients such as propylene glycol (PG), glycerol (G) or polyethylene glycol 400 (PEG). In addition, no big crystals were detected for all the dry films containing the MXD-loaded nanoparticles of the invention formulations. In a similar way, FIG. 11 shows the SEM performed for the formulation of the MXD-loaded nanoparticles of the invention and for the commercial products. The data obtained from said FIG. 11 exactly correlate and confirmed the results obtained in FIG. 10. For commercial products (LACOVIN® 2% and ALOPEX® 2%), big crystals precipitates were observed. On the other hand, no big crystals were observed for the formulation of the MXD-loaded nanoparticles of the invention (NPGES/MXD, NPGES/MXD G, NPGES/MXD PG and NPGES/MXD PEG) [Example 8]. Both MXD-loaded nanoparticles of the invention without excipients (NPGES/MXD) and MXD-loaded nanoparticles of the invention with glycerol (NPGES/MXD G) shown the presence of an homogeneous film containing the nanoparticles with an homogeneous average size distribution. Surprisingly, no nanoparticles were detected in the dry films containing MXD-loaded nanoparticles of the invention with PG or with PEG, what may be due to the solubility of the polymers in said excipients after water evaporation. It is important to note that some big precipitates (polymeric film layers) were observed for the formulation containing PEG 400 which may be related to the interaction of some carboxylic groups of the polymer with PEG. All the films were elegant with a light adhesive tacky texture.

On the other hand, cyclodextrins (CD) have been used to prepare an inclusion complex with MXD in order to investigate both MXD solubility and skin permeability [21]. Monoolein (MO) cubic phases entrapping hydroxypropyl beta-cyclodextrin (HPbetaCD)/minoxidil (MXD) complex were prepared by hydrating molten MO with the complex solution. The nanoparticles of the cubic phase were prepared by a bath type sonication using a PLURONIC® F127 as a dispersant. In vitro skin permeation of MXD loaded in the cubic phase were higher than that of MXD dissolved in PG/water/ethanol (20/30/50, v/v/v), but the amount of MXD remained within skin was higher with the MXD solution than with the MXD-loaded nanoparticles. These data indicated that although CD-MXD complexes were applied, remaining residues of the scalp with crystalline aspect was detracted in lesser degree than MXD solution.

In summary, according to this invention, MXD-loaded nanoparticles based on half ($C_1$-$C_4$) alkyl esters of PVM/MA copolymers have been designed with the aim to develop drug delivery systems for the treatment of alopecia androgenetica. The most important advantage of MXD-loaded nanoparticles based on half ($C_1$-$C_4$) alkyl esters of PVM/MA copolymers (invention) as drug delivery systems, compared to the common commercial formulations assayed, relate to the facility of fabrication, the avoidance of PG as an allergic vehicle and the absence of crystals formation phenomena on the scalp.

A further objective of the present invention was related to the development of bioadhesive nanoparticles based on half ($C_1$-$C_4$) alkyl esters of PVM/MA copolymers that are able to be maintained adhered to hair, for long time, at different conditions. The applications of said nanosystems in cosmetical products may be beneficial to deliver molecules to hair shaft or to offer protection against external aggressive factors and could enhance hair volume. The results indicate that the amount of the adhered fraction on hair samples was about 9.5 µg of nanoparticles per cm$^2$ hair surface area for group 1 (M1). In the other group of hair samples (M2), although the amount of the adhered fraction of the nanoparticles was reduced by hair washing, it was found that the nanoparticles still adhered to the hair surface (3.5 µg of nanoparticles per cm$^2$ hair surface area). The fluorescence and SEM (FIGS. 12 and 13) confirmed the initial high adhesive affinity of the suspension of the MXD-loaded nanoparticles provided by the present invention to the hair surface. In addition, the dry film of the nanoparticles adhered on the hair surface in group 1 resisted the washing and high temperature conditions and the nanoparticles were maintained adhered to the surface of hair as seen for group 2 (M2). In addition, the aspect of the hair containing the film of the MXD-loaded nanoparticles of the invention was elegant, transparent, brilliant and did not show any black residues after drying (Example 9).

Finally, an ex vivo bioadhesive study for MXD-loaded nanoparticles based on half ($C_1$-$C_4$) alkyl esters of PVM/MA copolymers (invention) was performed in buccal and tongue mucosa of a porcine animal model (Example 10). The objective of that work was focused on measuring the adhered fraction of the nanoparticles to the mucosal surface and the permanence time of these adhesive systems compared with reference GANTREZ® AN nanoparticles. FIGS. 14A and 14B represents the accumulative quantity of the adhered fraction of the nanoparticles formulation (µg NP/cm$^2$ tissue) for half ($C_1$-$C_4$) alkyl esters of PVM/MA copolymers (invention) and for GANTREZ® AN copolymers in both buccal and tongue porcine dorsal mucosa, respectively. Generally, MXD-loaded nanoparticles based on half ($C_1$-$C_4$) alkyl esters of PVM/MA copolymers (invention) (NP GESR) shown a higher adhesive capacity than MXD-loaded nanoparticles based on GANTREZ® ANs (NP GANR). However, both types of nanoparticles displayed a similar initial adhesive force at time 0. Nevertheless, at 1, 2.5, 4 and 6 hours, the accumulative adhered fractions of the MXD-loaded nanoparticles based on half ($C_1$-$C_4$) alkyl esters of PVM/MA copolymers (invention), in both types of porcine mucosa, were approximately 2-3 times higher than for the MXD-loaded nanoparticles based on GANTREZ® AN. In case of gel formulations containing nanoparticles, it has been observed that the hyaluronate gel enhances the initial adhesive capacity of the MXD-loaded nanoparticles based on half ($C_1$-$C_4$) alkyl esters of PVM/MA copolymers (GELNP GES) was 2-times higher than for the nanoparticles suspension. In addition, at 1, 2.5, 4 and 6 hours, a significant enhancement in the bioadhesive capacity was observed for the gel containing MXD-loaded nanoparticles based on half ($C_1$-$C_4$) alkyl esters of PVM/MA copolymers. Surprisingly, this phenomenon was not observed with the GANTREZ® AN-based nanoparticles gel formulations, wherein no significant differences between aqueous suspensions (NP GANR) and gel containing GANTREZ® AN nanoparticles (GEL NP GAN) were observed.

FIG. 15 shows the fluorescence microscopy images of both buccal mucosal tissues after 0.5 and 2.5 h of the administration of some fluorescently labelled nanoparticles formulations. Control tissue (without nanoparticles formulation) shown low fluorescence intensity in the tissue (FIG. 15B). Rhodamine B-loaded nanoparticles based on half ($C_1$-$C_4$) alkyl esters of PVM/MA copolymers displayed a high fluorescence intensity at the mucosal layer of the buccal mucosa at 0.5 hour post tissue incubation with salivary fluid (FIG. 15C) which was similar at 2.5 h (FIG. 15E). On the other hand, the tissue fluorescence intensity of GANTREZ® AN nanoparticles decreased from 0.5 to 2.5 h post incubation to be approximately similar to the control ones at 2.5 post administration (FIGS. 15 D and 15F). These data confirm that the nanoparticles of the invention, based on half ($C_1$-$C_4$) alkyl esters of PVM/MA copolymers, have a higher affinity and longer residence time in the buccal mucosa than GANTREZ® AN-based nanoparticles. In addition, it was observed that the nanoparticles did not penetrate to the sub-mucosal tissue in all the cases.

FIG. 16 shows the fluorescence microscopy images in tongue dorsum mucosal surface at 2.5 h after administration of the fluorescently labelled nanoparticles formulations. In a tissue similar to the buccal mucosal tissue, the nanoparticles of the invention, based on half ($C_1$-$C_4$) alkyl esters of PVM/MA copolymers, show a higher affinity and longer residence time in dorsal mucosa of porcine tongue (FIGS. 16C and 16D) than GANTREZ® AN-based nanoparticles (FIG. 16B).

According to the polymer characterization, the nanoparticles based on half ($C_1$-$C_4$) alkyl esters of PVM/MA copolymers (e.g., GANTREZ® ES) display a higher adhesive affinity to porcine buccal and tongue mucosa model surfaces than nanoparticles based on other GANTREZ® polymers, which guarantees an effective enhancement of the controlled release of many compounds. Surprisingly, half ($C_1$-$C_4$) alkyl esters of PVM/MA copolymers as well as nanoparticles based on said copolymers have a co-solvent effect for scarcely or poorly water soluble compounds leading to the enhancement of encapsulation efficiency of hydrophobic drugs, e.g., KTZ, TRI or MXD. Thus, said half ($C_1$-$C_4$) alkyl esters of PVM/MA copolymers appear to guarantee high encapsulation efficiencies for incorporating hydrophilic and, specially, hydrophobic compounds without the need of using co-solvents or complexing agents. The adhesive properties and the aqueous stability of the nanoparticles based on half ($C_1$-$C_4$) alkyl esters of PVM/MA copolymers, among other properties, make said nanoparticles to be potentially applied in a lot of industries, for example, pharmaceutical, cosmetic, agricultural or food industries, as controlled release products of interest delivery systems to different surfaces including hair, skin, buccal, oral, nasal, vaginal and rectal routs, among others.

BIBLIOGRAPHY

1. Illum, L., et al., *Chitosan as a novel nasal delivery system for vaccines*. Adv Drug Deliv Rev, 2001. 51(1-3): p. 81-96.
2. Read, R. C., et al., *Effective nasal influenza vaccine delivery using chitosan*. Vaccine, 2005. 23(35): p. 4367-74.
3. Mills, K. H., et al., *Protective levels of diphtheria-neutralizing antibody induced in healthy volunteers by unilateral priming-boosting intranasal immunization associated with restricted ipsilateral mucosal secretory immunoglobulin a*. Infect Immun, 2003. 71(2): p. 726-32.
4. Finne, U., K. Ronkko, and A. Urtti, *Timolol release from matrices of monoesters of poly(vinyl methyl ether-maleic anhydride): effects of polymer molecular weight and a basic additive*. J Pharm Sci, 1991. 80(7): p. 670-3.
5. Finne, U., V. Vaisanen, and A. Urtti, *Modification of ocular and systemic absorption of timolol from ocular inserts by a buffering agent and a vasoconstrictor*. Int J Pharm, 1990. 65: p. 19-27.
6. EP Publication No. 451390.
7. Arbos, P., et al. J Control Release, 2003. 89(1):19-30.

8. Arbos, P., et al., *Nanoparticles with specific bioadhesive properties to circumvent the pre-systemic degradation of fluorinated pyrimidines.* J Control Release, 2004. 96(1): p. 55-65.
9. Kockisch, S., et al., *Mucoadhesive, triclosan-loaded polymer microspheres for application to the oral cavity: preparation and controlled release characteristics.* Eur J Pharm Biopharm, 2005. 59(1): p. 207-16.
10. Kockisch et al. J Pharm Sci, 2003. 92(8):1614-23.
11. Marchais, H., et al., *Entrapment efficiency and initial release of phenylbutazone from nanocapsules prepared from different polyesters.* Drug Dev Ind Pharm, 1998. 24(9): p. 883-8.
12. Arbos, P., et al., Quantification of the bioadhesive properties of protein-coated PVM/MA nanoparticles. Int J Pharm, 2002. 242(1-2):129-36
13. Salman, H. H., et al., *Bioadhesive mannosylated nanoparticles for oral drug delivery.* J Nanosci Nanotechnol, 2006. 6(9-10):3203-9.
14. Erika Rosa Maria Kedor-Hackmann, et al., First-derivative ultraviolet spectrophotometric and high performance liquid chromatographic determination of ketoconazole in pharmaceutical emulsions. Brazilian Journal of Pharmaceutical Sciences, 2006. 42(1):91-98].
15. Gehan Balata, M. M., Rania Abu Bakera, *Improvement of solubility and dissolution properties of ketoconazole by solid dispersions and inclusion complexes.* Asian Journal of Pharmaceutical Sciences, 2010. 5(1): p. 1-12.
16. Kwon & Kim, In vitro skin permeation of monoolein nanoparticles containing hydroxypropyl beta-cyclodextrin/minoxidil complex. Int J Pharm, 2010. 392(1-2):268-73.
17. Dominguez-Delgado, C. L., et al., Eur J Pharm Biopharm, 2011[Epub ahead of print].
18. Takeuchi, H. H., et al., *Mucoadhesive nanoparticulate systems for peptide drug delivery.* Adv. Drug Deiv. Rev., 2001, 47(1):39-54.
19. Peh & Wong, *Polymeric films as vehicle for buccal delivery: swelling, mechanical, and bioadhesive properties.* J Pharm Pharm Sci, 1999. 2(2):53-61.
20. Perioli, L., et al., *Novel mucoadhesive buccal formulation containing metronidazole for the treatment of periodontal disease.* J Control Release, 2004. 95(3):521-33.
21. Kim, J. C. and M. D. Kim, J Microbiol Biotechnol, 2007. 17(12):1965-9.

The invention claimed is:

1. A nanoparticle selected from the group consisting of:
a) a matrix nanosphere, wherein said matrix nanosphere comprises a matrix, said matrix comprising a half ($C_1$-$C_4$) alkyl ester of a poly (methyl vinyl ether-co-maleic anhydride) (PVM/MA) copolymer; and
b) a core-shell vesicular nanocapsule, wherein said core-shell vesicular nanocapsule comprises a core and a shell, said shell comprising a half ($C_1$-$C_4$) alkyl ester of a PVM/MA copolymer,
wherein the nanoparticle has long-term stability in aqueous media.

2. The nanoparticle according to claim 1, wherein ($C_1$-$C_4$) alkyl is ethyl, isopropyl or n-butyl.

3. The nanoparticle according to claim 1, wherein the average size of the nanoparticle is comprised between 50 and 300 nm.

4. The nanoparticle according to claim 1, further comprising a product of interest.

5. A composition comprising at least one nanoparticle according to claim 1, and a carrier.

6. The nanoparticle according to claim 5, wherein said nanoparticle comprises a product of interest.

7. The nanoparticle according to claim 6, wherein said product of interest is an herbicide, an insecticide, a fungicide, an anti-aging product, an anti-acne product, a facial care product, a pigmented cosmetic, a cosmetical, a personal care product, a product for sunscreen/suncare, a product for toothcleaners, toothpastes, or rinses, a product for shampoos, a perfume, a hair products, folic acid, 4-aminobenzoic acid, niacin or vitamin B3, pantothenic acid or vitamin B5, thiamine monophosphate, thiamine pyrophosphate, thiamine triphosphate, ascorbic acid, pteroylpolyglutamic acids, folinic acid, nicotinic acid, hyaluronic acid, thioctic acid, p-coumaric acid, caffeic acid, a vitamin of the A, D, E, K families and derivatives thereof, a phospholipid, a carotenoid, a fatty acid, an omega-3 fatty acid, an amino acid, a phytostanol, a phytosterol, a polyphenol, an analgesic agent, an antialopecia agent, an antianginal agent, an antibacterial agent, an antidepressant agent, an antifungal agent, an antihypertensive agent, an antiinflammatory agent, an antineoplastic agent, an antipyretic agent, an antipsychotic agent, an anxiolytic agent, a bronchodilator agent, a glucocorticoid, an immunosuppressant agent, or any combination thereof.

8. A composition comprising:
a) a component selected from the group consisting of:
i) at least one nanoparticle according to claim 1 further comprising a product of interest; and
ii) a solution or suspension containing a half ($C_1$-$C_4$) alkyl ester of a poly (methyl vinyl ether-co-maleic anhydride) (PVM/MA) copolymer and a product of interest in a medium, said medium comprising a volatile water miscible alcohol and an aqueous medium, wherein the amount of aqueous medium is lower than the necessary amount of aqueous medium to form nanoparticles; and
b) a carrier,
wherein said product of interest is selected from the group consisting of acetylsalicylic acid, alpha-atrial natriuretic peptide, arginine vasopressin, atropine, augmerosen, atorvastatin, bevacizumab, calcitonins, chorionic gonadotropins, corticotropin, desmopressin, epibatidine, cetuximab, exenatide, trastuzumab, adalimumab, human insulin, ketoconazole, lanreotide, lutropin alpha, metoprolol, minoxidil, nesiritide, octreotide, paclitaxel, paracetamol, pegaptanib, recombinant follicle stimulating hormone, recombinant growth factors, infliximab, rituximab, sermorelin, somatotropin, a taxane derivative, taxol, teriparatide acetate, thyrotropin, triclosan, urofollitropin, omalizumab, actinomycin D, albendazole, aldosterone, alprazolam, amiodarone, amitriptyline, amprenavir, asimadoline, atorvastatin, bunitrolol, buspirone, camptothecin, carbamazepine, carvedilol, celiprolol, cyclosporine A, cimetidine, clotrimazole, colchicine, cortisone, daunorubicin, debrisoquine, dexamethasone, diazepam, digitoxin, digoxin, diltiazem, docetaxel, domperidone, doxorubicin, efavirenz, epirubicin, erythromycin, ergotamine, estradiol, estradiol glucuronide, erlotinib, etoposide, phenytoin, fentanyl, felodipine, phenothiazines, fexofenadine, fluoroquinolones, fluorouracil, FK-506, gentamicin, griseofulvin, hydrocortisone, imatinib, indinavir, itraconazole, ivermectin, ketoconazole, kaempferol, levofloxacin, lidocaine, loperamide, losartan, lovastatin, mebendazole, methylprednisolone, methotrexate, mibefradil, midazolam, nisoldipine, morphine, nelfinavir, nicardipine, nitrendipine, nifedipine, ondansetron, paclitaxel, pentazocine, praziquantel, prednisolone, prednisone, quercetin, quinidine, ranitidine, rapamycin, rifabutin, rifampicin, ritonavir, saquinavir, sirolimus, sulfamethizole, tacrolimus, tamoxifen, talinolol, teniposide, terfenadine, tetracycline, topotecan, triamcinolone, valspodar, verapamil, vinblastine, vincristine, vindesine, zopiclone, and mixtures thereof.

9. The nanoparticle according to claim 5, wherein said composition is in the form of a dry powder.

10. The nanoparticle according to claim 5, wherein said carrier comprises a pharmaceutically acceptable excipient for the administration thereof by the buccal, dental, nasal, ocular, oral, parenteral, rectal, topical, or vaginal routes, or a cosmetically acceptable excipient for the administration thereof by topical route.

11. A foodstuff comprising a nanoparticle according to claim 1.

12. A method of treatment of hair loss in a subject comprising the administration to said subject of a nanoparticle according to claim 4 loaded with minoxidil.

13. A method of treatment of a buccal infection in a subject comprising the administration to said subject of a nanoparticle according to claim 4 loaded with triclosan or ketoconazole.

14. A process for producing the matrix nanosphere of claim 1, wherein the matrix nanosphere comprises a matrix, said matrix comprising a half ($C_1$-$C_4$) alkyl ester of a poly (methyl vinyl ether-co-maleic anhydride) (PVM/MA) copolymer, said process comprising contacting an organic solution or suspension containing a half ($C_1$-$C_4$) alkyl ester of a PVM/MA copolymer with an aqueous medium in order to form said matrix nanosphere.

15. A process for producing the matrix nanosphere of claim 1, wherein the matrix nanosphere comprises a product of interest, wherein said matrix nanosphere comprises a matrix, said matrix comprising a half ($C_1$-$C_4$) alkyl ester of a poly (methyl vinyl ether-co-maleic anhydride) (PVM/MA) copolymer, said process comprising:
 a) contacting an alcoholic or hydroalcoholic solution or suspension comprising said product of interest and said half ($C_1$-$C_4$) alkyl ester of the PVM/MA copolymer with an aqueous medium; or, alternatively,
 b) contacting an alcoholic solution or suspension comprising said product of interest and said half ($C_1$-$C_4$) alkyl ester of the PVM/MA copolymer with an aqueous medium; or, alternatively,
 c) contacting an organic solution or suspension comprising said product of interest and said half ($C_1$-$C_4$) alkyl ester of the PVM/MA copolymer with an aqueous medium, wherein said organic solution or suspension comprises a non-volatile water miscible solvent.

16. A process for producing the core-shell vesicular nanocapsule of claim 1, wherein the core-shell vesicular nanocapsule comprises a product of interest, wherein said core-shell vesicular nanocapsule comprises a core and a shell, said shell comprising a half ($C_1$-$C_4$) alkyl ester of a PVM/MA copolymer, said process comprising contacting a solution or suspension comprising said product of interest and said half ($C_1$-$C_4$) alkyl ester of a PVM/MA copolymer with an aqueous medium.

17. A process for producing a nanoparticle of claim 1, said process comprising removing a solvent in an hydroalcoholic solution or suspension containing a half ($C_1$-$C_4$) alkyl ester of a PVM/MA copolymer and a water miscible alcohol, wherein the amount of water is lower than the necessary amount of water to form the nanoparticles.

18. The process according to claim 17 further comprising a product of interest.

19. An in situ process for producing a nanoparticle of claim 1 on a skin surface, said process comprising removing a solvent in an hydroalcoholic solution or suspension containing a half ($C_1$-$C_4$) alkyl ester of a PVM/MA copolymer, a water miscible alcohol and a product of interest, wherein the amount of water is lower than the necessary amount of water to form the nanoparticles.

20. The composition according to claim 8, wherein said composition is in the form of a dry powder.

21. The nanoparticle according to claim 1, wherein said nanoparticle has long-term stability in aqueous media for at least three months.

22. The nanoparticle according to claim 1, wherein said nanoparticle does not include cross-linking agents.

* * * * *